Figure 1A:
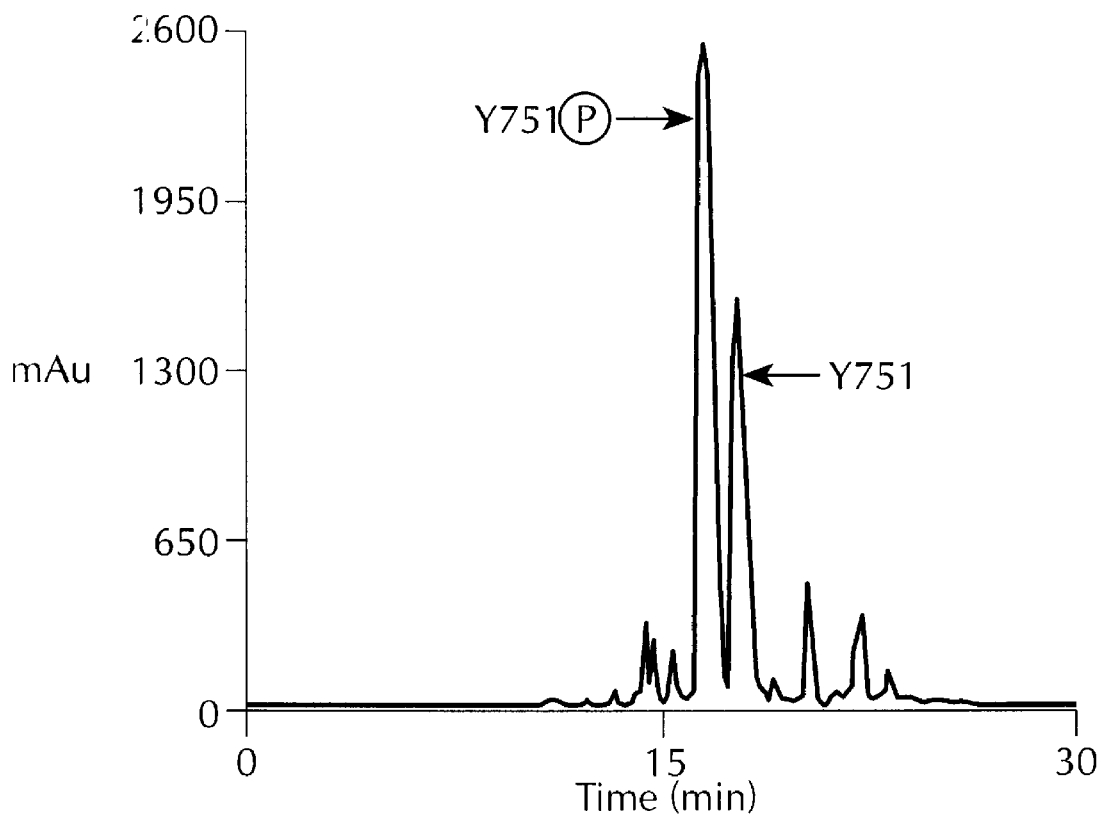
Figure 1B:
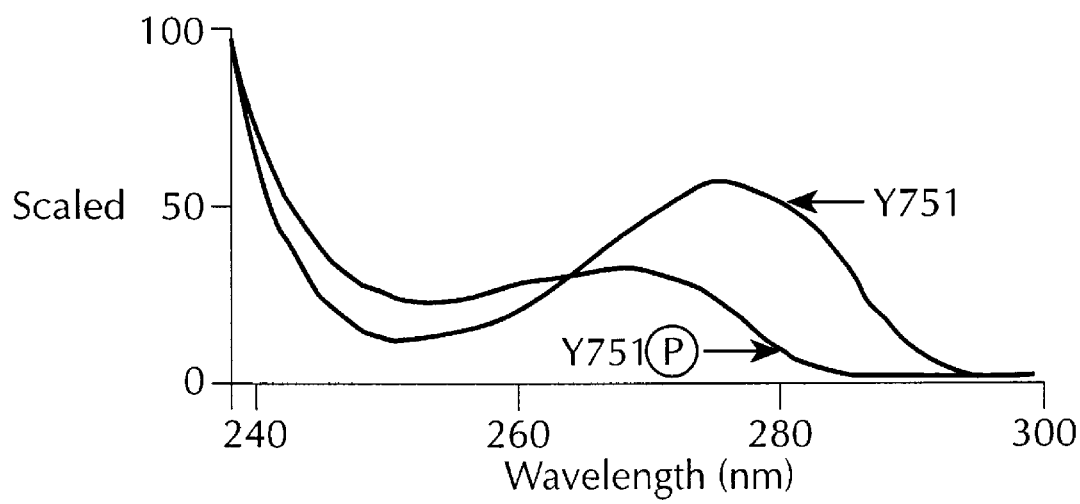
Figure 1C:
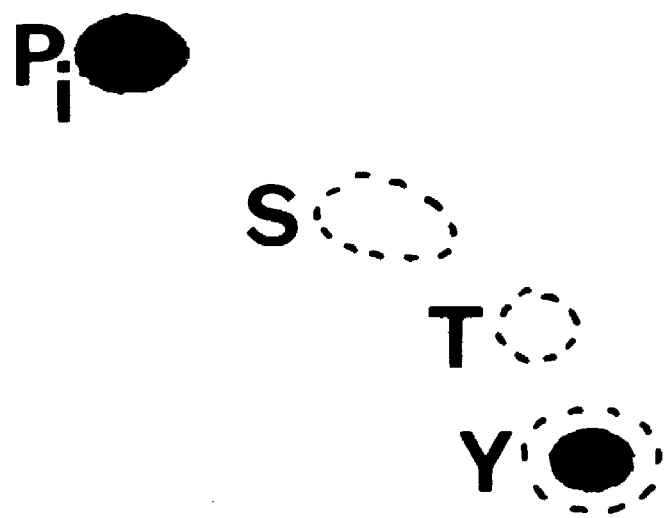
Figure 1D:
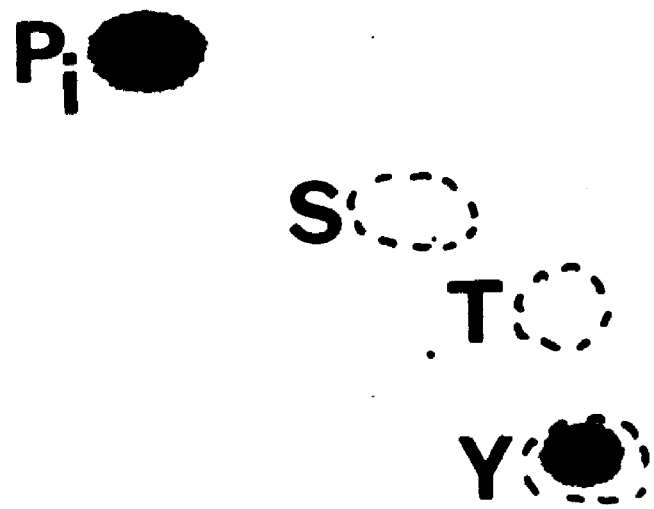

United States Patent
Hiles et al.

[11] Patent Number: 5,824,492
[45] Date of Patent: Oct. 20, 1998

[54] POLYPEPTIDES HAVING KINASE ACTIVITY, THEIR PREPARATION AND USE

[75] Inventors: Ian D. Hiles; Michael J. Fry; Ritu Dhand; Michael D. Waterfield; Peter J. Parker; Masayuki Otsu; George Panayoutou; Stefano Volinia; Ivan Gout, all of London, England

[73] Assignee: Ludwig Institute for Cancer Research, New York, N.Y.

[21] Appl. No.: 162,081

[22] PCT Filed: Apr. 13, 1993

[86] PCT No.: PCT/GB93/00761

§ 371 Date: Feb. 7, 1994

§ 102(e) Date: Feb. 7, 1994

[87] PCT Pub. No.: WO93/21328

PCT Pub. Date: Oct. 28, 1995

[30] Foreign Application Priority Data

Apr. 13, 1992 [GB] United Kingdom ............... 9208135

[51] Int. Cl.$^6$ ................ C12N 9/12; C12Q 1/48

[52] U.S. Cl. ................. 435/15; 435/29; 435/794

[58] Field of Search .............. 435/15, 194, 94.5

[56] References Cited

PUBLICATIONS

Hiles et al., Cell 70:419–429 (1992).
Hu et al., Mol. Cell. Biol. 13:7677–7688 (1993).
Carpenter et al., J. Biol. Chem. 265:19704–19711 (1990).
Shibasaki et al., J. Biol. Chem. 266:8108–8114 (1991).
Cantley et al., Cell 64: 281–302 (1991).
Savitsky et al., Science 268: 1749–1753 (1995).

*Primary Examiner*—Robert A. Wax
*Assistant Examiner*—Eric Grimes
*Attorney, Agent, or Firm*—Felfe & Lynch

[57] ABSTRACT

This invention relates to new polypeptides which exhibit kinase activity or, more specifically, which show phosphoinositide (PI) 3-kinase activity. Such polypeptides are involved in pathways responsible for cellular growth and differentiation. An isolated polypeptide which possesses PI3-kinase activity when produced by recombinant production in insect cells is disclosed.

7 Claims, 76 Drawing Sheets

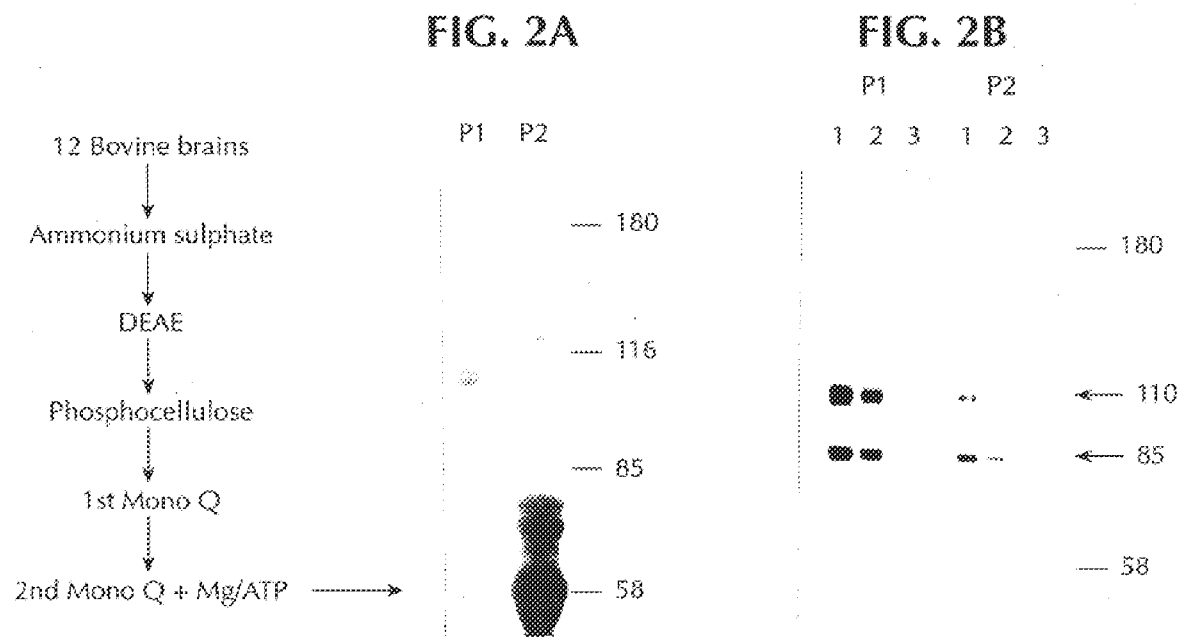

FIG. 4A

1 2 3 4 5 6 7

—180

—116

—84

—58 anti-ALPHA

FIG. 4B

1 2 3 4 5 6 7

—180

—116

—84

—58 anti-BETA

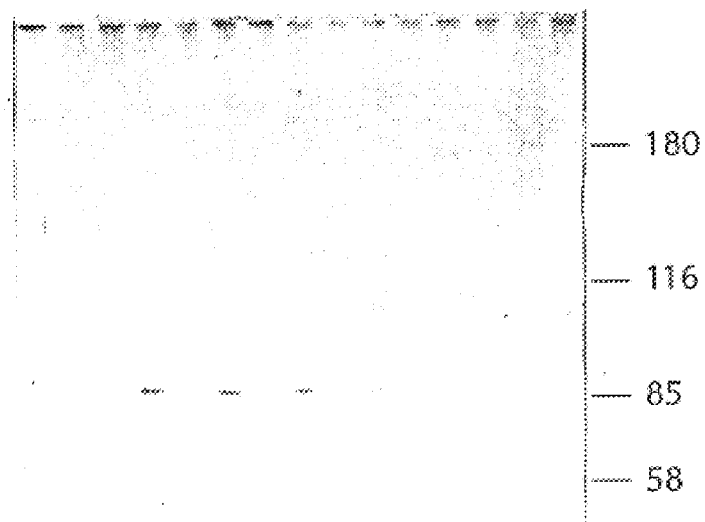
FIG. 6A
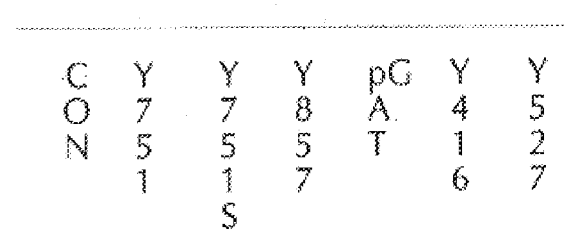
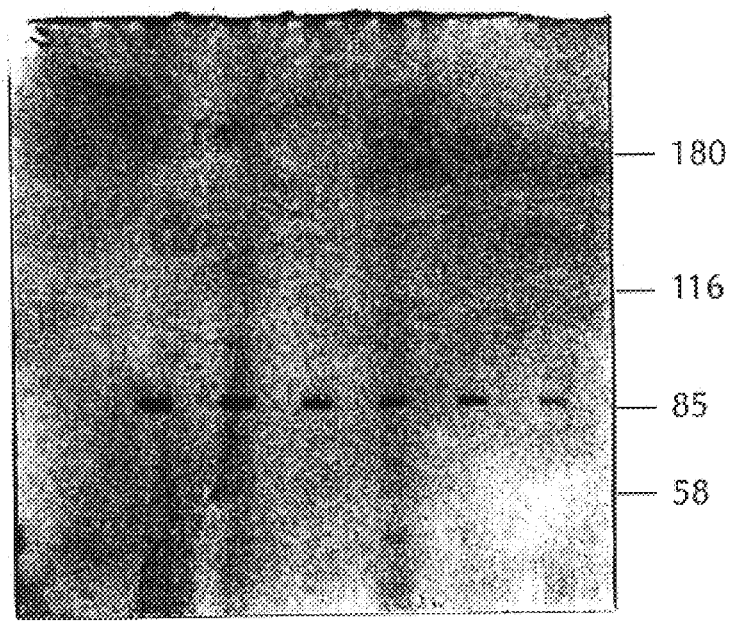
FIG. 6B
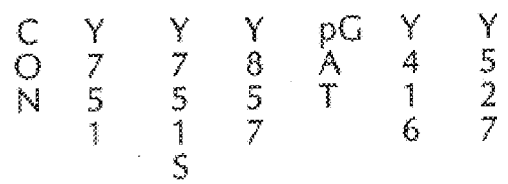

```
751          D M S K D E S V D Y V P M L D M K
751.S              C D E S V D Y V P M L
740                G E S D G G Y M D M S K
1313               E F C P D P L Y E V M L K

Consensus          E E E E E Y M P M X X
                   D D D D D   V
```

FIG. 9A

| | | |
|---|---|---|
| M P P R P S S G E L W G I H L M | | 16 |
| ATGCCTCCAAGACCATCATCAGGTGAACTGTGGGGCATCCACTTGATG | | 48 |
| | | |
| P P R I L V E C L L P N G M I V | | 32 |
| CCCCCAAGAATCCTAGTAGAATGTTTACTACCAAATGGATGATAGTG | | 96 |
| | | |
| T L E C L R E A T L I T K H E | | 48 |
| ACTTTAGAATGCCTCCGTGAGGCTACGTTAATAACGATAAAGCATGAA | | 144 |
| | | |
| L F K E A R K Y P L H Q L L Q D | | 64 |
| CTATTTAAAGAAGCAAGAAAATACCCTCTCCATCAACTTCTTCAAGAT | | 192 |
| | | |
| E S S Y I F V S V T Q E A E R E | | 80 |
| GAATCTTCTTACATTTTCGTAAGTGTTACCCAAGAAGCAGAAAGGGAA | | 240 |
| | | |
| E F F D E T R R L C D L R L F Q | | 96 |
| GAATTTTTTGATGAAACAAGACGACTTTGTGACCTTCGGCTTTTTCAA | | 288 |
| | | |
| P F L K V I E P V G N R E E K I | | 112 |
| CCCTTTTTAAAAGTAATTGAACCAGTAGGCAACCGTGAAGAAAAGATC | | 336 |
| | | |
| L N R E I G F A I G M P V C E F | | 128 |
| CTCAATCGAGAAATTGGTTTTGCTATCGGCATGCCAGTGTGTGAATTC | | 384 |
| | | |
| D M V K D P E V Q D F R R N I L | | 144 |
| GATATGGTTAAAGATCCAGAAGTACAGGACTTCCGAAGAAATATTCTC | | 432 |

FIG. 9B

```
  N   V   C   K   E   A   V   D   L   R   D   L   N   S   P   H      160
AATGTTTGTAAAGAAGCTGTGGATCTTAGGGATCTTAATTCACCTCAT                     480
                       A
  S   R   A   M   Y   V   Y   P   P   N   V   E   S   S   P   E      176
AGTAGAGCAATGTATGTTTATCCTCCAAATGTAGAATCTTCACCAGAA                     528

L   P   K   H   I   Y   N   K   L   D   K   G   Q   I   I   V      192
CTGCCAAAGCACATATATAATAAATTGGATAAAGGGCAAATAATAGTG                     576

V   I   W   V   I   V   S   P   N   N   D   K   Q   K   Y   T      208
GTGATTTGGGTAATAGTTTCTCCAAATAATGACAAACAGAAGTATACT                     624

L   K   I   N   H   D   C   V   P   E   Q   V   I   A   E   A      224
CTGAAAATCAACCATGACTGTGTGCCAGAACAAGTAATTGCTGAAGCA                     672

I   R   K   K   T   R   S   M   L   L   S   S   E   Q   L   K      240
ATCAGGAAAAAAACTCGAAGTATGTTGCTATCATCTGAACAACTAAAA                     720

L   C   V   L   E   Y   Q   G   K   Y   I   L   K   V   C   G      256
CTCTGTGTTTTAGAATATCAGGGCAAGTATATTTTAAAAGTGTGTGGA                     768

C   D   E   Y   F   L   E   K   Y   P   L   S   Q   Y   K   Y      272
TGTGATGAATACTTCCTAGAAAAATATCCTCTGAGTCAGTATAAGTAT                     816

I   R   S   C   I   M   L   G   R   M   P   N   L   M   L   M      288
ATAAGAAGCTGTATAATGCTTGGGAGGATGCCCAATTTGATGCTGATG                     864
```

FIG. 9C

```
  A   K   E   S   L   Y   S   Q   L   P   M   D   C   F   T   M      304
GCTAAAGAAAGCCTCTATTCTCAACTGCCAATGGACTGTTTTACAATG                    912

P   S   Y   S   R   R   I   S   T   A   T   P   Y   M   N   G    320
CCATCATATTCCAGACGCATCTCCACAGCTACGCCATATATGAATGGA                    960
                          B
  E   T   S   T   K   S   L   W   V   I   N   S   A   L   R   I    336
GAAACATCTACAAAATCCCTTTGGGTTATAAATAGTGCACTCAGAATA                    1008

K   I   L   C   A   T   Y   V   N   V   N   I   R   D   I   D    352
AAAATTCTTTGTGCAACCTATGTGAATGTAAATATTCGAGACATTGAC                    1056

K   I   Y   V   R   T   G   I   Y   H   G   G   E   P   L   C    368
AAGATTTATGTTCGAACAGGTATCTACCATGGAGGAGAACCCTTATGT                    1104

D   N   V   N   T   Q   R   V   P   C   S   N   P   R   W   N    384
GATAATGTGAACACTCAAAGAGTACCTTGTTCCAATCCCAGGTGGAAT                    1152

E   W   L   N   Y   D   I   Y   I   P   D   L   P   R   A   A    400
GAATGGCTGAATTACGATATATACATTCCTGATCTTCCTCGTGCTGCT                    1200

R   L   C   L   S   I   C   S   V   K   G   R   K   G   A   K    416
CGACTTTGCCTTTCCATTTGTTCTGTTAAAGGCCGAAAGGGTGCTAAA                    1248

E   E   H   C   P   L   A   W   G   N   I   N   L   F   D   Y    432
GAGGAACACTGTCCATTGGCCTGGGGAAATATAAACTTGTTTGATTAC                    1296
```

FIG. 9D

```
      T  D  T  L  V  S  G  K  M  A  L  N  L  W  P  V       448
      ACAGATACTCTAGTATCTGGAAAAATGGCTTTGAATCTTTGGCCAGTA      1344
                              C
      P  H  G  L  E  D  L  L  N  P  I  G  V  T  G  S       464
      CCTCATGGACTAGAAGATTTGCTGAACCCTATTGGTGTTACTGGATCA      1392

N  P  N  K  E  T  P  C  L  E  L  E  F  D  W  F       480
      AATCCAAATAAAGAAACTCCATGTTTAGAGTTGGAGTTTGACTGGTTC      1440

S  S  V  V  K  F  P  D  M  S  V  I  E  E  H  A       496
      AGCAGTGTGGTAAAGTTTCCAGATATGTCAGTGATTGAAGAGCATGCC      1488

N  W  S  V  S  R  E  A  G  F  S  Y  S  H  A  G       512
      AATTGGTCTGTATCCCGTGAAGCAGGATTTAGTTATTCCCATGCAGGA      1536

L  S  N  R  L  A  R  D  N  E  L  R  E  N  D  K       528
      CTGAGTAACAGACTAGCTAGAGACAATGAATTAAGAGAAAATGATAAA      1584

E  Q  L  R  A  I  C  T  R  D  P  L  S  E  I  T       544
      GAACAGCTCCGAGCAATTTGTACACGAGATCCTCTATCTGAAATCACT      1632

E  Q  E  K  D  F  L  W  S  H  R  H  Y  C  V  T       560
      GAGCAAGAGAAAGATTTTCTGTGGAGCCACAGACACTATTGTGTAACT      1680

I  P  E  I  L  P  K  L  L  S  V  K  W  N  S          576
      ATCCCCGAAATTCTACCCAAATTGCTTCTGTCTGTTAAATGGAACTCT      1728
```

FIG. 9E

```
      R   D   E   V   A   Q   M   Y   C   L   V   K   D   W   P   P        592
      AGAGATGAAGTAGCTCAGATGTACTGCTTGGTAAAAGATTGGCCTCCA                      1776

I   K   P   E   Q   A   M   E   L   L   D   C   N   Y   P   D        608
      ATCAAGCCTGAACAGGCTATGGAGCTTCTGGACTGCAATTACCCAGAT                      1824

P   M   V   R   G   F   A   V   R   C   L   E   K   Y   L   T        624
      CCTATGGTTCGAGGTTTTGCTGTTCGGTGCTTAGAAAAATATTTAACA                      1872
                                                  D
      D   D   K   L   S   Q   Y   L   I   Q   L   V   Q   V   L   K        640
      GATGACAAACTTTCTCAGTACCTAATTCAGCTAGTACAGGTACTAAAA                      1920

Y   E   Q   Y   L   D   N   L   L   V   R   F   L   L   K   K        656
      TATGAACAGTATTTGGATAACCTGCTTGTGAGATTTTTACTCAAAAAA                      1968
                                  E
      A   L   T   N   Q   R   I   G   H   F   F   F   W   H   L   K        672
      GCGTTAACTAATCAAAGGATCGGTCACTTTTTCTTTTGGCATTTAAAA                      2016
                                              F
      S   E   M   H   N   K   T   V   S   Q   R   F   G   L   L   L        688
      TCTGAGATGCACAATAAAACAGTTAGTCAGAGGTTTGGCCTGCTTTTG                      2064

E   S   Y   C   R   A   C   G   M   Y   L   K   H   L   N   R        704
      GAGTCCTATTGCCGTGCATGTGGATGTATCTGAAGCACCTTAATAGG                       2112
                                              G
      Q   V   E   A   M   E   K   L   I   N   L   T   D   I   L   K        720
      CAAGTTGAGGCTATGGAAAAGCTCATTAACTTGACTGACATTCTCAAA                      2160
```

FIG. 9F

```
      Q   E   F   K   D   E   T   Q   K   V   Q   M   K   F   L   V     736
     CAAGAGAAGAAGGATGAAACACAAAAGGTACAGATGAAGTTTTTAGTT                    2208

E   Q   M   R   R   P   D   F   M   D   A   L   Q   G   F   L     752
     GAGCAAATGCGGCGACCAGATTTCATGGATGCTCTCCAGGGCTTTCTG                    2256

S   P   L   N   P   A   H   Q   L   G   N   L   R   L   E   E     768
     TCTCCTCTAAACCCTGCTCATCAGCTGGGAAATCTCAGGCTTGAAGAG                    2304

C   R   I   M   S   S   A   K   R   P   L   W   L   N   W   E     784
     TGTCGAATTATGTCTTCTGCAAAAAGGCCACTGTGGTTGAATTGGGAG                    2352

N   P   D   I   M   S   E   L   L   F   Q   N   N   E   I   I     800
     AACCCAGACATCATGTCAGAATTACTCTTTCAGAACAATGAGATCATC                    2400

F   K   N   G   D   D   L   R   Q   D   M   L   T   L   Q   I     816
     TTTAAAAATGGGGATGATTTACGGCAAGATATGCTAACCCTTCAGATT                    2448

I   R   I   M   E   N   I   W   Q   N   Q   G   L   D   L   R     832
     ATTCGCATTATGGAAAATATCTGGCAAAATCAAGGTCTTGATCTTCGA                    2496

M   L   P   Y   G   C   L   S   I   G   D   C   V   G   L   I     848
     ATGTTACCTTATGGATGTCTGTCAATCGGTGACTGTGTGGGACTTATC                    2544

E   V   V   R   N   S   H   T   I   M   Q   I   Q   C   K   G     864
     GAGGTGGTGAGAAATTCTCACACTATAATGCAGATTCAGTGTAAAGGA                    2592
```

FIG. 9G

```
                                H
    G   L   K   G   A   L   Q   F   N   S   H   T   L   H   Q   W      880
    GGCCTGAAAGGTGCACTGCAGTTTAACAGCCACACACTCCATCAGTGG                    2640

L   K   D   K   N   K   G   E   I   Y   D   A   A   I   D   L      896
    CTCAAAGACAAGAACAAGGGGGAAATATATGATGCGGCCATCGATTTG                    2688
                I
    F   T   R   S   C   A   G   Y   C   V   A   T   F   I   L   G      912
    TTTACACGATCATGTGCTGGATATTGTGTTGCCACCTTCATTTTGGGA                    2736

I   G   D   R   H   N   S   N   I   M   V   K   D   D   G   Q      928
    ATTGGAGATCGTCACAATAGTAATATCATGGTTAAAGATGATGGACAA                    2784
                        J
    L   F   H   I   D   F   G   H   F   L   D   H   K   K   K   K      944
    CTGTTTCATATAGATTTTGGACACTTTTTGGATCACAAGAAGAAAAAA                    2832
                                                K
    F   G   Y   K   R   E   R   V   P   F   V   L   T   Q   D   F      960
    TTTGGTTATAAACGAGAGCGCGTGCCGTTTGTTTTGACACAAGATTTC                    2880

L   I   V   I   S   K   G   A   Q   E   C   T   K   T   R   E      976
    TTAATAGTGATTAGTAAAGGAGCCCAAGAATGCACAAAGACAAGAGAA                    2928

F   E   R   F   Q   E   M   C   Y   K   A   Y   L   A   I   R      992
    TTTGAGAGGTTTCAGGAGATGTGTTACAAGGCTTATCTAGCTATTCGG                    2976
```

FIG. 9H

```
           L
 Q  H  A  N  L  F  I  N  L  F  S  M  M  L  G  S            1008
CAGCATGCCAATCTCTTCATAAATCTTTTCTCAATGATGCTTGGCTCT           3024

G  M  P  E  L  Q  S  F  D  D  I  A  Y  I  R  K            1024
GGAATGCCAGAACTGCAATCTTTTGATGATATTGCATACATTCGAAAG           3072
                            M
 T  L  A  L  D  K  T  E  Q  E  A  L  E  Y  F  M            1040
ACCCTAGCTTTAGATAAAACTGAGCAAGAGGCTTTGGAGTATTTCATG           3120

K  Q  M  N  D  A  H  H  G  G  W  T  T  K  M  D            1056
AAACAAATGAATGATGCACACCATGGTGGCTGGACAACAAAAATGGAT           3168
        N
 W  I  F  H  T  I  K  Q  H  A  L  N  *                     1069
TGGATCTTCCACACAATTAAGCAGCATGCTTTGAACTGA                    3207
```

FIG. 10B

```
P110       VCEFDMVKDPEVQDFRRNILNVCKEAVDLRDLNSPHSRAMYVYPPN 170
            ..|  :  .|  ::  .|  ..:  .. |:..  ...: :...|
VPS34      NITFCVSQDLDVP.LKVKIKSLEGHKPLLKPSQKILNPELMLIGSN 49

171     VESSPEL..PKHIYNKLDKGQIIVVIWVIVSPNNDKQKYTLKINHDCVPE 218
            | .|.:|  . ::::|  . .:.:.|:.  |  .:......:
    50     VFPSSDLIVSLQVFDKERNRNLTLPIYTPYIPFRNSRTWDYWL....... 92

219     QVIAEAIRKKTRSMLLSSEQLKLCVLEYQGKYILKVCGCDEYFLEKYPLS 268
             .:. :.: : :|| :|::.::||.|
    93     .....TLPIRIKQLTFSS.HLRIILWEYNG.................... 116

269     QYKYIRSCIMLGRMPNLMLMAKESLYSQLPMDCFTMPSYSRRISTATPYM 318
                                                    |...|::
   117     ..........................................SKQIPFF 123

319     NGETSTKSLWVINSALRIKILCATYVNVNIRDIDKIYVRTGIYHGGEPLC 368
            | |||. : : ::.|:          |::..: .| ::.. .|.:.
   124     NLETSI..FNLKDCTLK............RGFESLKFRYDVIDHCEVVT 158

369     DNVNTQRVPCSNPRWNEWLNYDIYIPDLPRAARLC.LSICSVKGRKGAKE 417
            || :          .| ||  ..: .:::.| ::|  :.|:..: ..:.:
   159     DNKD..........QENLN.KYFQGEFTRLPWLDEITISKLRKQRENRT 196
```

FIG. 10C

```
418 .EHCPLAWG.NINLFDYTDTLVSGKMALNLWPVPHGLEDLLNPIGVTGS. 464
    .:...:.. :: :::.. .::.. .:  .   :|    .| |  |:...
197 WPQGTFVLNLEFPMLELPVVFIEREIMNTQMNIP....TLKNNPGLSTDL 242

465 .NPNKETPCLELEF.DWFSSVVKFPDMSVIEEHANWSVSREAGFSYSHAG 512
    :||::.|  :.:.: |.: |.:|| |    .:::|  ..  |   ...:|:
243 REPNRNDPQIKISLGDKYHSTLKFYD....PDQPNNDPIEEKYRRLERAS 288

513 LSNRLARDNELRENDKEQLRAICTRDPLSEITEQEKDFLWSHRHYCVTIP 562
    ...|.::  .   ..:: |. |.. .|  ..:|.:||: :|..|.| :. .
289 KNANLDKQVKPDIKKRDYLNKIINYPPGTKLTAHEKGSIWKYRYYLMNNK 338

563 EILPKLLLSVKWNSRDEVAQMYCLVKDWPPIKPEQAMELLDCNYPDPMVR 612
    . |.||| |..:..  .|  .:::. |:..|:.|. ::|:|||::.:.:  ||
339 KALTKLLQSTNLREESERVEVLELMDSWAEIDIDDALELLGSTFKNLSVR 388

613 GFAVRCLEKYLTDDKLSQYLIQLVQVLKYEQY.................. 644
    ::||. |.|  .|..|. ||:|||:.: :|..
389 SYAVNRLKK.ASDKELELYLLQLVEAVCFENLSTFSDKSNSEFTIVDAVS 437

645 ...........................LDNLLVRFLLKK 656
                                : . |. ||:::
438 SQKLSGDSMLLSTSHANQKLLKSISSESETSGTESLPIVISPLAEFLIRR 487
```

FIG. 10D

```
 657 ALTNQRIGHFFFWHLKSEMHNKTVSQRFGLLLESY.CRACGMYLKHLNRQ  705
     ||.|.|:| ||:|.||||  .:|.    ::  :|.|:  :|   .  || |
 488 ALVNPRLGSFFYWYLKSESEDKPY...LDQILSSFWSRLDKKSRNILNDQ  534

706 VEAMEKLINLTDILKQEKKDETQKVQMKF.LVEQMRRPDFMDALQGFLSP  754
     |  ::  |  : .:.:|.  |.....|:::  .  |:| .  ||  :  :..:  |
 535 VRLINVLRECCETIKRLKDTTAKKMELLVHLLETKVRP..LVKVRPIALP  582

755 LNPAHQLGNLRLEECRIMSSAKRPLWLNWENPDIMSELLFQNNEIIFKNG  804
     |:|.   :.::   |.:::::.|. .||.:.:...    || .::|| |
 583 LDPDVLICDVCPETSKVFKSSLSPLKITFKTT......LNQPYHLMFKVG  626
                                             *.
 805 DDLRQDMLTLQIIRIMENIWQNQGLDLRMLPYGCLSIGDCVGLIEVVRNS  854
     ||||||  |.:|||.:|:::::.|:.:||::  ||  .|..|.   |  ||.:.|
 627 DDLRQDQLVVQIISLMNELLKNENVDLKLTPYKILATGPQEGAIEFIPN.  675
       *.
 855 HTIMQIQCK.GGLKGALQFNSHTLHQWLKDKNKGEIYDAAIDLFTRSCAG  903
     .|:   |  :|   |:  |  |.:      ::  .:...  ::   :  .:|  |.:||||
 676 DTLASILSKYHGILGYLKL......HYPDENATLGVQGWVLDNFVKSCAG  719
              .*    *   .        ***    .
 904 YCVATFILGIGDRHNSNIMVKDDGQLFHIDFGHFLDHKKKKFGYKRERVP  953
     |||  |:|||:||||  .|::|..||::||  |||.:|:...|.|         |
 720 YCVITYILGVGDRHLDNLLVTPDGHFFHADFGYILGQDPKPF.......P  762

954 FVLTQDFLIVISKGAQECTKTREFERFQEMCYKAYLAIRQHANLFINLFS  1003
     :::.  .  |: . |:.|:.   ::::|..  |:  ||   :|.:|.|::|||.
 763 PLMKLPPQIIEAFGGAESS...NYDKFRSYCFVAYSILRRNAGLIINLFE  809

1004 MMLGSGMPE..LQSFDDIAYIRKTLALDKTEQEALEYFMKQMNDAHHGGW  1051
     :| .|.:|:   ::. :.|   :|.  :.|:..|::|   .|  .:||.  ::  :
 810 IMKTSNIPDIRIDPNGAILRVRERFNLNMSEEDATVHFQNLINDSVNALL  859

1052 TTKMDWIFHTIKQH  1065
     ..  :|   :|.:  |.
 860 PIVIDH.LHNLAQY  872
```

FIG. 15A
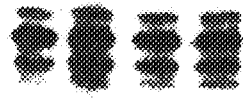
FIG. 15B
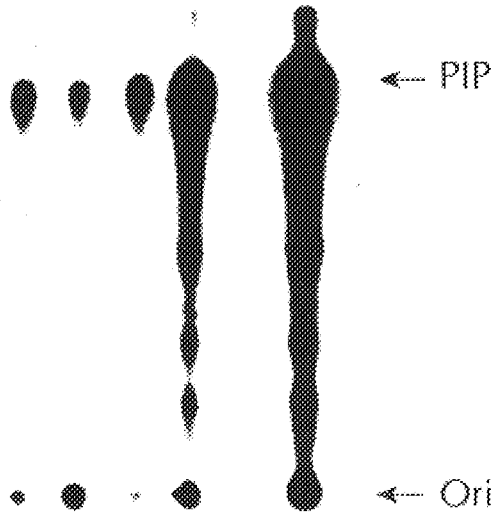
FIG. 15C
FIG. 15D
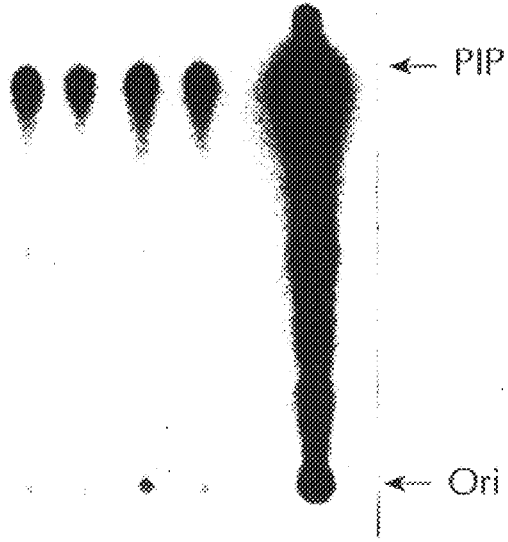

FIG. 16A

```
1    ATGCCTCCAAGACCATCATCAGGTGAACTGTGGGGCATCCACTTGATG     48
     ----+----+----+----+----+----+----+----+----+----
     TACGGAGGTTCTGGTAGTAGTCCACTTGACACCCCGTAGGTGAACTAC
     M  P  P  R  P  S  S  G  E  L  W  G  I  H  L  M

49   CCCCCAAGAATCCTAGTGGAATGTTACTACCAAATGGAATGATAGTG     96
     ----+----+----+----+----+----+----+----+----+----
     GGGGGTTCTTAGGATCACCTTACAAATGATGGTTTACCTTACTATCAC
     P  P  R  I  L  V  E  C  L  L  P  N  G  M  I  V

97   ACTTTAGAATGCCTCCCGTGAGGCTACATTAGTAACTATAAAGCATGAA    144
     ----+----+----+----+----+----+----+----+----+----
     TGAAATCTTACGGAGGGCACTCCGATGTAATCATTGATATTTCGTACTT
     T  L  E  C  L  R  E  A  T  L  V  T  I  K  H  E

145  CTATTTAAAGAAGCAAGAAAAATACCCTCTCCATCAACTTCTTCAAGAT    192
     ----+----+----+----+----+----+----+----+----+----
     GATAAATTTCTTCGTTCTTTTATGGGAGAGGTAGTTGAAGAAGTTCTA
     L  F  K  E  A  R  K  Y  P  L  H  Q  L  L  Q  D
```

FIG. 16B

```
193  GAATCTTCTTACATTTTCGTAAGTGTTACCCAAGAAGCAGAAAGGGAA  240
     ----+----+----+----+----+----+----+----+----+----
     CTTAGAAGAATGTAAAAGCATTCACAATGGGTTCTTCGTCTTTCCCTT
      E  S  S  Y  I  F  V  S  V  T  Q  E  A  E  R  E

241  GAATTTTTTGATGAAAACAAGACGACTTTGTGATCTTCGGCTTTTCAA  288
     ----+----+----+----+----+----+----+----+----+----
     CTTAAAAAACTACTTTTGTTCTGCTGAAACACTAGAAGCCGAAAAGTT
      E  F  F  D  E  T  R  R  L  C  D  L  R  L  F  Q

289  CCATTTTTAAAAGTAATTGAACCAGTAGGCAACCCGTGAAGAAAAGATC  336
     ----+----+----+----+----+----+----+----+----+----
     GGTAAAAATTTTCATTAACTTGGTCATCCGTTGGGCACTTCTTTTCTAG
      P  F  L  K  V  I  E  P  V  G  N  R  E  E  K  I

337  CTCAATCGAGAAATTGGTTTTGCTATCGGCATGCCAGTGTGCGAATTT  384
     ----+----+----+----+----+----+----+----+----+----
     GAGTTAGCTCTTTAACCAAAACGATAGCCGTACGGTCACACGCTTAAA
      L  N  R  E  I  G  F  A  I  G  M  P  V  C  E  F
```

FIG. 16C

```
      GATATGGTTAAAGATCCCTGAAGTACAGGACTTCCGAAGAAATATTCTT      432
385   ----+----+----+----+----+----+----+----+----+----
      CTATACCAATTTCTAGGGACTTCATGTCCTGAAGGCTTCTTTATAAGAA
       D  M  V  K  D  P  E  V  Q  D  F  R  R  N  I  L

AATGTTTGTAAAGAAGCTGTGGATCTTAGGGATCTTAATTCACCTCAT      480
433   ----+----+----+----+----+----+----+----+----+----
      TTACAAACATTTCTTCGACACCTAGAATCCCTAGAATTAAGTGGAGTA
       N  V  C  K  E  A  V  D  L  R  D  L  N  S  P  H

AGTAGAGCAATGTATGTCTATCCGCCCACATGTAGAATCTTCACCAGAG      528
481   ----+----+----+----+----+----+----+----+----+----
      TCATCTCGTTACATACAGATAGGCGGGTGTACATCTTAGAAGTGGTCTC
       S  R  A  M  Y  V  Y  P  P  H  V  E  S  S  P  E

CTGCCCAAAGCACACATATAATAAATTGGATAGAGGCCAAATAATAGTG     576
529   ----+----+----+----+----+----+----+----+----+----
      GACGGTTCGTGTGTATATATTATTTAACCTATCTCCGGTTTATTATCAC
       L  P  K  H  I  Y  N  K  L  D  R  G  Q  I  I  V
```

FIG. 16D

```
577  GTGATTGGGTAATAGTTTCTCCAAATAATGACAAGCAGAAGTATACT
     ---+---------+---------+---------+---------+-  624
     CACTAAACCCATTATCAAAGAGGTTTATTACTGTTCGTCTTCATATGA
      V  I  W  V  I  V  S  P  N  N  D  K  Q  K  Y  T

625  CTGAAAATCAACCATGACTGTGTGCCAGAACAAGTAATTGCTGAAGCA
     ---+---------+---------+---------+---------+-  672
     GACTTTTAGTTGGTACTGACACACGGTCTTGTTCATTAACGACTTCGT
      L  K  I  N  H  D  C  V  P  E  Q  V  I  A  E  A

673  ATCAGGAAAAAAACTAGAAGTATGTTGCTATCATCTGAACAATTAAAA
     ---+---------+---------+---------+---------+-  720
     TAGTCCTTTTTTTGATCTTCATACAACGATAGTAGACTTGTTAATTTT
      I  R  K  K  T  R  S  M  L  L  S  S  E  Q  L  K

721  CTCTGTGTTTTAGAATATCAGGGCAAGTACATTTAAAAGTGTGTGGA
     ---+---------+---------+---------+---------+-  768
     GAGACACAAAATCTTATAGTCCCGTTCATGTAAATTTCACACACCT
      L  C  V  L  E  Y  Q  G  K  Y  I  L  K  V  C  G
```

FIG. 16E

```
769  TGTGATGAATACTTCCTAGAAAAATATCCTCTCTGAGTCAGTATAAGTAT  816
     ---------+---------+---------+---------+---------+
     ACACTACTTATGAAGGATCTTTTTATAGGAGACTCAGTCATATTCATA
      C   D   E   Y   F   L   E   K   Y   P   L   S   Q   Y   K   Y

817  ATAAGAAGCTGTATAATGCTTGGGAGGATGCCCAATTTGAAGATGATG  864
     ---------+---------+---------+---------+---------+
     TATTCTTCGACATATTACGAACCCTCCTACGGGTTAAACTTCTACTAC
      I   R   S   C   I   M   L   G   R   M   P   N   L   K   M   M

865  GCTAAAGAAAAGCCTTTATTCTCAACTGCCAATGGACTGTTTTACAATG  912
     ---------+---------+---------+---------+---------+
     CGATTTCTTTTCGGAAATAAGAGTTGACGGTTACCTGACAAAATGTTAC
      A   K   E   S   L   Y   S   Q   L   P   M   D   C   F   T   M

913  CCATCTTATTCCAGACGCATTCCACAGCTACACCATATATGAATGGA  960
     ---------+---------+---------+---------+---------+
     GGTAGAATAAGGTCTGCGTAAGGTGTCGATGTGGTATATACTTACCT
      P   S   Y   S   R   R   I   S   T   A   T   P   Y   M   N   G
```

FIG. 16F

```
      GAAACATCTACAAAATCCCTTTGGGTTATAAATAGAGCACTCAGAATA
961   ---------+---------+---------+---------+--------  1008
      CTTTGTAGATGTTTTAGGGAAACCCAATATTTATCTCGTGAGTCTTAT
       E  T  S  T  K  S  L  W  V  I  N  R  A  L  R  I

AAAATTCTTTGTGCAACCTACGTGAATCTAAATATTCGAGACATTGAC
1009  ---------+---------+---------+---------+--------  1056
      TTTTAAGAAACACGTTGGATGCACTTAGATTTATAAGCTCTGTAACTG
       K  I  L  C  A  T  Y  V  N  L  N  I  R  D  I  D

AAGATTATGTTCGAACAGGTATCTACCATGGAGGAGAACCCTTATGT
1057  ---------+---------+---------+---------+--------  1104
      TTCTAAATACAAGCTTGTCCATAGATGGTACCTCCTCTTGGGAATACA
       K  I  Y  V  R  T  G  I  Y  H  G  G  E  P  L  C

GACAATGTGAACACTCAAAGAGTACCTTGTTCCAATCCCAGGTGGAAT
1105  ---------+---------+---------+---------+--------  1152
      CTGTTACACTTGTGAGTTTCTCATGGAACAAGGTTAGGGTCCACCTTA
       D  N  V  N  T  Q  R  V  P  C  S  N  P  R  W  N
```

FIG. 16G

```
      GAATGGCTGAATTATGATATATACATTCCCTGATCTCTTCCCTCGTGCTGCT
1153  ----+----+----+----+----+----+----+----+----+----+  1200
      CTTACCGACTTAATACTATATATGTAAGGACTAGAAGGAGCACGACGA
       E  W  L  N  Y  D  I  Y  I  P  D  L  P  R  A  A

CGACTTTGCCTTTCCATTTGCTCTCTGTTAAAGGCCGAAAGGGTGCTAAA
1201  ----+----+----+----+----+----+----+----+----+----+  1248
      GCTGAAACGGAAAGGTAAACGAGACAATTCCGGCTTTCCCACGATTT
       R  L  C  L  S  I  C  S  V  K  G  R  K  G  A  K

GAGGAACACTGTCCATTGGCATGGGGGAAATATAAACTTGTTTGATTAC
1249  ----+----+----+----+----+----+----+----+----+--+  1296
      CTCCTTGTGACAGGTAACCGTACCCCCTTTATATTTGAACAAACTAATG
       E  E  H  C  P  L  A  W  G  N  I  N  L  F  D  Y

ACAGACACTCTAGTATCTGGGAAAAATGGCTTTGAATCTTTGGCCAGTA
1297  ----+----+----+----+----+----+----+----+----+----+  1344
      TGTCTGTGAGATCATAGACCTTTTTACCGAAACTTAGAAACCGGTCAT
       T  D  T  L  V  S  G  K  M  A  L  N  L  W  P  V
```

FIG. 16H

```
1345  CCTCATGGATTAGAAGATTGCTGAACCCTATTGGTGTGTTACTGGATCA  1392
      ---------+---------+---------+---------+---------+
      GGAGTACCTAATCTTCTAAACGACTTGGGATAACCACAATGACCTAGT
       P  H  G  L  E  D  L  L  N  P  I  G  V  T  G  S

1393  AATCCAAATAAAGAAACTCCATGCTTAGAGTTGGAGTTTGACTGGTTC  1440
      ---------+---------+---------+---------+---------+
      TTAGGTTTATTTCTTTGAGGTACGAATCTCAACCTCAAACTGACCAAG
       N  P  N  K  E  T  P  C  L  E  L  E  F  D  W  F

1441  AGCAGTGTGGTAAAGTTCCCAGATATGTCAGTGATTGAAGAGCATGCC  1488
      ---------+---------+---------+---------+---------+
      TCGTCACACCATTTCAAGGGTCTATACAGTCACTAACTTCTCGTACGG
       S  S  V  V  K  F  P  D  M  S  V  I  E  E  H  A

1489  AATTGGTCTGTATCCCGAGAAGCAGGATTTAGCTATTCCCACGCAGGA  1536
      ---------+---------+---------+---------+---------+
      TTAACCAGACATAGGGCTCTTCGTCCTAAATCGATAAGGGTGCGTCCT
       N  W  S  V  S  R  E  A  G  F  S  Y  S  H  A  G
```

FIG. 16I

```
       CTGAGTAACAGACTAGCTAGAGACAATGAATTAAGGGAAAATGACAAA
1537   ---+---------+---------+---------+---------+---    1584
       GACTCATTGTCTGATCGATCTCTGTTACTTAATTCCCTTTTACTGTTT
        L  S  N  R  L  A  R  D  N  E  L  R  E  N  D  K

GAACAGCTCAAAGCAATTTCTACACGAGATCCCTCTCTCTGAAATCACT
1585   ---+---------+---------+---------+---------+----   1632
       CTTGTCGAGTTTCGTTAAAGATGTGCTCTAGGAGAGAGACTTTAGTGA
        E  Q  L  K  A  I  S  T  R  D  P  L  S  E  I  T

GAGCAGGAGAAAGATTTTCTATGGAGTCACAGACACTATTGTAACT
1633   ---+---------+---------+---------+---------+--     1680
       CTCGTCCTCTTTCTAAAAGATACCTCAGTGTCTGTGATAACACATTGA
        E  Q  E  K  D  F  L  W  S  H  R  H  Y  C  V  T

ATCCCCGAAATTCTACCCAAATTGCTTCTGTCTGTTAAATGGAATTCT
1681   ---+---------+---------+---------+---------+---    1728
       TAGGGGCTTTAAGATGGGTTTAACGAAGACAATTTACCTTAAGA
        I  P  E  I  L  P  K  L  L  L  S  V  K  W  N  S
```

FIG. 16J

```
1729  AGAGATGAAGTAGCCCAGATGTATTGCTTGGTAAAAGATTGGCCTCCA  1776
      ----+----+----+----+----+----+----+----+----+----
      TCTCTACTTCATCGGGTCTACATAACGAACCATTTCTAACCGGAGGT
       R  D  E  V  A  Q  M  Y  C  L  V  K  D  W  P  P

1777  ATCAAACCTGAACAGGCTATGGAACTTCTGGACTGTAATTACCCAGAT  1824
      ----+----+----+----+----+----+----+----+----+----
      TAGTTTGGACTTGTCCGATACCTTGAAGACCTGACATTAATGGGTCTA
       I  K  P  E  Q  A  M  E  L  L  D  C  N  Y  P  D

1825  CCTATGGTTCGAGGTTTTTGCTGTCGGTTCGGTTGCTTGGAAAATATTTAACA  1872
      ----+----+----+----+----+----+----+----+----+----
      GGATACCAAGCTCCAAAACGACAAGCCACGAACCTTTTTATAAATTGT
       P  M  V  R  G  F  A  V  R  C  L  E  K  Y  L  T

1873  GATGACAAACTTTCTCAGTATTTAATTCAGCTAGTACAGGTCCTAAAA  1920
      ----+----+----+----+----+----+----+----+----+----
      CTACTGTTTGAAAGAGTCATAAATTAAGTCGATCATGTCCAGGATTTT
       D  D  K  L  S  Q  Y  L  I  Q  L  V  Q  V  L  K
```

FIG. 16K

```
1921 TATGAACAATATTTGGATAACCTTGCTTGTGAGATTTTACTGAAGAAA
     ----+----+----+----+----+----+----+----+----+----+
     ATACTTGTTATAAACCTATTGAACGAACACTCTAAAAATGACTTCTTT  1968
      Y  E  Q  Y  L  D  N  L  L  V  R  F  L  L  K  K

1969 GCATTGACTAATCAAAGGATTGGGCACTTTTTCTTTTGGCATTTAAAA
     ----+----+----+----+----+----+----+----+----+----+
     CGTAACTGATTAGTTTCCTAACCCGTGAAAAGAAAACCGTAAATTTT  2016
      A  L  T  N  Q  R  I  G  H  F  F  F  W  H  L  K

2017 TCTGAGATGCACAATAAAAACAGTTAGCCAGAGGTTTGGCCTGCTTTTG
     ----+----+----+----+----+----+----+----+----+----+
     AGACTCTACGTGTTATTTTGTCAATCGGTCTCCAAACCGGACGAAAAC  2064
      S  E  M  H  N  K  T  V  S  Q  R  F  G  L  L  L

2065 GAGTCCTATTGTCGTGCATGTGGATGTATTTGAAGCACCTGAATAGG
     ----+----+----+----+----+----+----+----+----+----+
     CTCAGGATAACAGCACGTACACCTACATAAACTTCGTGGACTTATCC  2112
      E  S  Y  C  R  A  C  G  M  Y  L  K  H  L  N  R
```

FIG. 16L

```
           2113                                            2160
           CAAGTCGAGGCAATGGAAAAAGCTCATTAACTTAACTGACATTCTCAAA
                -----+----+----+----+----+----+----+----+-----
           GTTCAGCTCCGTTACCTTTTTCGAGTAATTGACTGTAAGAGTTT
             Q  V  E  A  M  E  K  L  I  N  L  T  D  I  L  K 2161                                            2208
           CAGGAGGAGGAAGGATGAAACAAAGGTACAGATGAAGTTTTTAGTT
                -----+----+----+----+----+----+----+----+-----
           GTCCTCCTCCTTCCTACTTTGTGTTTCCATGTCTACTTCAAAAATCAA
             Q  E  R  K  D  E  T  Q  K  V  Q  M  K  F  L  V 2209                                            2256
           GAGCAAATGAGGCGACCAGATTTCATGGATGCCCTACAGGGCTTGCTG
                -----+----+----+----+----+----+----+----+-----
           CTCGTTTACTCCGCTGGTCTAAAGTACCTACGGGATGTCCCGAACGAC
             E  Q  M  R  R  P  D  F  M  D  A  L  Q  G  L  L 2257                                            2304
           TCTCCTCTAAACCCTGCTCATCAACTAGGAAACCTCAGGCTTAAAGAG
                -----+----+----+----+----+----+----+----+-----
           AGAGGAGATTTGGGACGAGTAGTTGATCCTTTGGAGTCCGAATTCTC
             S  P  L  N  P  A  H  Q  L  G  N  L  R  L  K  E
```

FIG. 16M

```
2305  TGTCGAATTATGTCTTCTCTGCAAAAGGCCACTGTGGTTGAATTGGGAG   2352
      ----+----+----+----+----+----+----+----+----+----
      ACAGCTTAATACAGAAGAGACGTTTTCCGGTGACACCAACTTAACCCTC
        C  R  I  M  S  S  A  K  R  P  L  W  L  N  W  E

2353  AACCCAGACACATCATGTCAGAGTTACTGTTTCAGAACAATGAGATCATC  2400
      ----+----+----+----+----+----+----+----+----+----
      TTGGGTCTGTGTAGTACAGTCTCAATGACAAAGTCTTGTTACTCTAGTAG
        N  P  D  I  M  S  E  L  L  F  Q  N  N  E  I  I

2401  TTTAAAAATGGGGATGATTTACGGCAAGATATGCTAACACTTCAAATT    2448
      ----+----+----+----+----+----+----+----+----+----
      AAATTTTTACCCCTACTAAATGCCGTTCTATACGATTGTGAAGTTTAA
        F  K  N  G  D  D  L  R  Q  D  M  L  T  L  Q  I

2449  ATTCGTATTATGGAAAATATCTGGCAAATCAAGGTCTTGATCTTCGA     2496
      ----+----+----+----+----+----+----+----+----+----
      TAAGCATAATACCTTTTATAGACCGTTTAGTTCCAGAACTAGAAGCT
        I  R  I  M  E  N  I  W  Q  N  Q  G  L  D  L  R
```

FIG. 16N

```
2497  ATGTTACCTTATGGTTGTCTGTCAATCGGTGACTGTGTGGGACTTATT   2544
      ----+----+----+----+----+----+----+----+----+----
      TACAATGGAATACCAACAGACAGTTAGCCACTGACACACCCTGAATAA
       M  L  P  Y  G  C  L  S  I  G  D  C  V  G  L  I

2545  GAGGTGGTGCGAAATTCTCACACTATTATGCAAATTCAGTGCAAAGGC   2592
      ----+----+----+----+----+----+----+----+----+----
      CTCCCACCACGCTTTAAGAGTGTGATAATACGTTTAAGTCACGTTTCCG
       E  V  V  R  N  S  H  T  I  M  Q  I  Q  C  K  G

2593  GGCTTGAAAGGTGCACTGCAGTTCAACAGCCACACTACATCAGTGG    2640
      ----+----+----+----+----+----+----+----+----+----
      CCGAACTTTCCACGTGACGTCAAGTTGTCGGTGTGATGTAGTCACC
       G  L  K  G  A  L  Q  F  N  S  H  T  L  H  Q  W

2641  CTCAAAGACAACAAGAACAAAGGAGAAATATATGATGCAGCCATTGACCTG   2688
      ----+----+----+----+----+----+----+----+----+----
      GAGTTTCTGTTGTTCTTGTTTCCTCTCTTTATATACTACGTCGGTAACTGGAC
       L  K  D  K  N  K  G  E  I  Y  D  A  A  I  D  L
```

FIG. 16O

```
2689  TTTACACGTTCATGTGCTGGATACTGTGTAGCTACCTTCATTTTGGGA  2736
      ----+----+----+----+----+----+----+----+----+----
      AAATGTGCAAGTACACGACCTATGACACATCGATGGAAGTAAAACCCT
       F  T  R  S  C  A  G  Y  C  V  A  T  F  I  L  G

2737  ATTGGAGATCGTCACAATAGTAACATCATGGTGAAAGACGATGGACAA  2784
      ----+----+----+----+----+----+----+----+----+----
      TAACCTCTAGCAGTGTTATCATTGTAGTACCACTTTCTGCTACCTGTT
       I  G  D  R  H  N  S  N  I  M  V  K  D  D  G  Q

2785  CTGTTTCATATAGATTTTGGACACTTTTTTGGATCACAAGAAAAAAAA  2832
      ----+----+----+----+----+----+----+----+----+----
      GACAAAGTATATCTAAAACCTGTGAAAAACCTAGTGTTCTTTTTTTTT
       L  F  H  I  D  F  G  H  F  L  D  H  H  K  K  K

2833  TTTGGTTATAAACGAGAACGTGTGCCATTTGTTTTGACACAGGATTTC  2880
      ----+----+----+----+----+----+----+----+----+----
      AAACCAATATTTGCTCTTGCACACGGTAAACAAAACTGTGTCCTAAAG
       F  G  Y  K  R  E  R  V  P  F  V  L  T  Q  D  F
```

FIG. 16P

```
       TTAATAGTGATTAGTAATAAAGGAGCCCAAGAATGCACAAAGACAAGAGAA
2881   --------+---------+---------+---------+---------+   2928
       AATTATCACTAATCATTTCCTCGGGTTCTTACGTGTTTCTGTTCTCTT
        L  I  V  I  S  K  G  A  Q  E  C  T  K  T  R  E

TTTGAGAGGTTTCAGGAGATGTGTTACAAGGCTTATCTAGCTATTCGA
2929   --------+---------+---------+---------+---------+   2976
       AAACTCTCCAAAGTCCTCTACACAATGTTCCGAATAGATCGATAAGCT
        F  E  R  F  Q  E  M  C  Y  K  A  Y  L  A  I  R

CAGCATGCCAATCTCTTCATAAATCTTTTCTTCAATGATGCTTGGCTCT
2977   --------+---------+---------+---------+---------+   3024
       GTCGTACGGTTAGAGAAGTATTTAGAAAAGAGTTACTACGAACCGAGA
        Q  H  A  N  L  F  I  N  L  F  S  M  M  L  G  S

GGAATGCCAGAACTACAATCTTTGATGACATTGCATACGTATGTAAGCTTTC
3025   --------+---------+---------+---------+---------+   3072
       CCTTACGGTCTTGATGTTAGAAACTACTGTAACGTATGTAAGCTTTC
        G  M  P  E  L  Q  S  F  D  D  I  A  Y  I  R  K
```

FIG. 16Q

```
3073  ACCCTAGCCTTAGATAAAACTGAGCAAGAGGCTTTGGAGTATTCATG
      ---------+---------+---------+---------+-----  3120
      TGGGATCGGAATCTATTTGACTCGTTCTCCGAAACCTCATAAAGTAC
       T  L  A  L  D  K  T  E  Q  E  A  L  E  Y  F  M

3121  AAACAAAATGAATGATGCACATCATGGTGGCTGGACAACAAAATGGAT
      ---------+---------+---------+---------+-----  3168
      TTTGTTTTACTTACTACGTGTAGTACCACCGACCTGTTGTTTTACCTA
       K  Q  M  N  D  A  H  H  G  G  W  T  T  K  M  D

3169  TGGATCTTCCACACAATTAAAACAGCATGCATTGAACTGAAAGATAACT
      ---------+---------+---------+---------+-----  3216
      ACCTAGAAGGTGTGTTAATTTGTCGTACGTAACTTGACTTTCTATTGA
       W  I  F  H  T  I  K  Q  H  A  L  N  *

3217  GAGAAAATGAAAGCTCACTCTGGATTCCACACTGCACTGTTAATAACT
      ---------+---------+---------+---------+-----  3264
      CTCTTTTACTTTCGAGTGAGACCTAAGGTGTGACGTGACAATTATTGA
```

FIG. 16R

```
     CTCAGCAGGCAAAGACCGATTGCATAGGAATTGCACAATCCATGAACA
3265 ---------+---------+---------+---------+--------  3312
     GAGTCGTCCGTTTCTGGCTAACGTATCCTTAACGTGTTAGGTACTTGT

GCATTAGATTTACAGCAAGAACAGAAAATAAAATACTATATAATTTAAA
3313 ---------+---------+---------+---------+--------  3360
     CGTAATCTAAATGTCGTTCTTGTCTTTTATTTTATGATATATTAAATTT

TAATGTAAACGCAAAACAGGGTTTGATAGCACTTAAACTAGTTCATTTC
3361 ---------+---------+---------+---------+--------  3408
     ATTACATTTGCGTTTGTCCCAAACTATCGTGAATTTGATCAAGTAAAG

AAAA
3409 -+--  3412
     TTTT
```

FIG. 17A

```
hum110    1 ATGCCTCCAAGACCATCATCAGGTGAACTGTGGGGCATCCACTTGATGCC   50
            ||||||||||||||||||||||||||||||||||||||||||||||||||
bov110    1 ATGCCTCCAAGACCATCATCAGGTGAACTGTGGGGCATCCACTTGATGCC   50

51 CCCAAGAATCCTAGTGTGGAATGTTTACTACCAAATGGAATGATAGTGACTT  100
            ||||||||||||||||||||| ||||||||||||| ||||||||||||||
         51 CCCAAGAATCCTAGTAGAATGTTTACTACCAAATGGGATGATAGTGACTT  100

101 TAGAATGCCTCCGTGAGGCTACACATTAGTAGTAACTATAAAGCATGAACTATTT  150
            ||||||||||||||||||||||||| ||| ||| ||||||||||||||||
        101 TAGAATGCCTCCGTGAGGCTACGTTAATAACGATAAAGCATGAACTATTT  150

151 AAAGAAGCAAGAAAATACCCTCTCCATCAACTTCTTCAAGATGAATCTTC  200
            ||||||||||||||||||||||||||||||||||||||||||||||||||
        151 AAAGAAGCAAGAAAATACCCTCTCCATCAACTTCTTCAAGATGAATCTTC  200
```

FIG. 17B

```
201 TTACATTTCGTAAGTGTTACCCAAGAAGCAGAAGGGAAGAATTTTTG 250
    ||||||||||||||||||||||||||||||||||||||||||||||
201 TTACATTTCGTAAGTGTTACCCAAGAAGCAGAAGGGAAGAATTTTTG 250

251 ATGAAACAAGACGACTTTGTGATCTTCGGCTTTTTCAACCATTTTAAAA 300
    ||||||||||||||||||||||||| |||||||||||| ||||||||
251 ATGAAACAAGACGACTTTGTGACCTTCGGCTTTTTCAACCCTTTTAAAA 300

301 GTAATTGAACCAGTAGGCAACCGTGAAGAAAAGATCCTCAATCGAGAAAT 350
    |||||||||||||||||||||||||||||||||||||||||||||||||
301 GTAATTGAACCAGTAGGCAACCGTGAAGAAAAGATCCTCAATCGAGAAAT 350

351 TGGTTTTGCTATCGGCATGCCAGTGTGCGAATTTGATATGGTTAAAGATC 400
    |||||||||||||||||||||||||| |||| ||||||||||||||||
351 TGGTTTTGCTATCGGCATGCCAGTGTGTGAATTCGATATGGTTAAAGATC 400

401 CTGAAGTACAGGACTTCCGAAGAAATATTCTTAATGTTTGTAAAGAAGCT 450
    | ||||||||||||||||||||||||||||||  ||||||||||||||
401 CAGAAGTACAGGACTTCCGAAGAAATATTCTCAATGTTTGTAAAGAAGCT 450
```

FIG. 17C

```
451 GTGGGATCTTAGGGATCTTAATTCACCTCATAGTAGAGCAATGTATGTCTA 500
    ||||||||||||||||||||||||||||||||||||||||||||||| ||
451 GTGGGATCTTAGGGATCTTAATTCACCTCATAGTAGAGCAATGTATGTTTA 500

501 TCCGCCACATGTAGAATCTTCACCAGAGCTGCCAAAGCACACATATAAATA 550
    |||  ||| ||||||||||||||||||||||||||||||||||||||||
501 TCCTCCAAATGTAGAATCTTCACCAGAACTGCCAAAGCACACATATAAATA 550

551 AATTGGATAGAGAGGCCAAATAATAGTGGTGATTTGGGTAATAGTTTCTCCA 600
    |||||||||||  ||| ||| |||||||||||||||||||||||||||||
551 AATTGGATAAAGGGGCAAAACAGAAGTAGTGGTGATTTGGGTAATAGTTTCTCCA 600

601 AATAATGACAAGCAGAAGTATACTCTGAAAATCAACCATGACTGTGTGCC 650
    ||||||||||||||||||||||||||||||||||||||||||||||||||
601 AATAATGACAAACAGAAGTATACTCTGAAAATCAACCATGACTGTGTGCC 650

651 AGAACAAGTAATTGCTGAAGCAATCAGGAGAAAAAACTAGAAGTATGTTGC 700
    ||||||||||||||||||||||||||||||||||||||||||||||||||
651 AGAACAAGTAATTGCTGAAGCAATCAGGAGAAAAAACTCGAAGTATGTTGC 700
```

FIG. 17D

```
701  TATCATCTGAACAATTAAAACTCTGTGTTTTAGAATATCAGGGCAAGTAC  750
     ||||||||||||||||  ||||||||||||||||||||||||||||||||
701  TATCATCTGAACAACTAAAACTCTGTGTTTTAGAATATCAGGGCAAGTAT  750

751  ATTTAAAAGTGTGTGGATGTGATGAATACTTCCTAGAAAAATATCCTCT  800
     |||||||||||||||||||||||||||||||||||||||||||||||||
751  ATTTAAAAGTGTGTGGATGTGATGAATACTTCCTAGAAAAATATCCTCT  800

801  GAGTCAGTATAAGTATATAAGAAGCTGTATAATGCTTGGGAGGATGCCCA  850
     |||||||||||||||||||||||||||||||||||||||||||||||||
801  GAGTCAGTATAAGTATATAAGAAGCTGTATAATGCTTGGGAGGATGCCCA  850

851  ATTTGAAGATGATGGCTAAAGAAAAGCCCTTTATTCTCAACTGCCAATGGAC  900
     |||| |||| ||||||||||||||||||||| ||||||||||||||||||
851  ATTTGATGCTGATGGCTAAAGAAAAGCCCTCTATTCTCAACTGCCAATGGAC  900

901  TGTTTTACAATGCCATCTTATTCCAGACGCATTCCACACCATA  950
     |||||||||||||||||||  ||||||||||| |||| |||||
901  TGTTTTACAATGCCATCATATTCCAGACGCATCTCCAGCTACGCCATA  950
```

FIG. 17E

```
 951 TATGAATGGAGAAACATCTACAAAATCCCTTTGGGTTATAAATAGAGCAC 1000
     ||||||||||||||||||||||||||||||||||||||||| ||||||||
 951 TATGAATGGAGAAACATCTACAAAATCCCTTTGGGTTATAAATAGTGCAC 1000

1001 TCAGAATAAAAATTCTTTGTGCAACCTACGTGAATCTAAATATTCGAGAC 1050
     |||||||||| ||||||||||||||||| |||| ||||||||||||||||
1001 TCAGAATAAAAATTCTTTGTGCAACCTATGTGAATGTAAATATTCGAGAC 1050

1051 ATTGACAAGATTTATGTTCGAACAGGTATCTACCATGGAGGAGAACCCTT 1100
     ||||||||||||||||||||||||||||||||||||||||||||||||||
1051 ATTGACAAGATTTATGTTCGAACAGGTATCTACCATGGAGGAGAACCCTT 1100

1101 ATGTGACAATGTGAACACTCAAAGAGTACCTTGTTCCAATCCCAGGTGGA 1150
     |||| |||| |||||||||||||||||||||||||||||||||||||||
1101 ATGTGATAATGTGAACACTCAAAGAGTACCTTGTTCCAATCCCAGGTGGA 1150

1151 ATGAATGGCTGAATTATGATATATACATTCCTGATCTTCCTCGTGCTGCT 1200
     |||||||||||||||| |||||||||||||||||||| ||||||||||||
1151 ATGAATGGCTGAATTACGATATATACATTCCTGATCTTCCTCGTGCTGCT 1200
```

FIG. 17F

```
1201  CGACTTTGCCTTTCCATTTGCTCTGTGTTAAAGGCCCGAAAGGGTGCTAAAGA  1250
      ||||||||||||||||||||| ||||||||||||||||||||||||||||||
1201  CGACTTTGCCTTTCCATTTGTTCTGTGTTAAAGGCCCGAAAGGGTGCTAAAGA  1250

1251  GGAACACTGTCCATTGGCATGGGGGAAATAAACTTGTTTGATTACACAG  1300
      |||||||||||||||||||| ||||||||||||||||||||||||||||
1251  GGAACACTGTCCATTGGCCTGGGGGAAATAAACTTGTTTGATTACACAG  1300

1301  ACACTCTAGTATCTGGAAAAATGGCTTTGAATCTTTGGCCAGTACCTCAT  1350
      | |||||||||||||||||||||||||||||||||||||||||||||||
1301  ATACTCTAGTATCTGGAAAAATGGCTTTGAATCTTTGGCCAGTACCTCAT  1350

1351  GGATTAGAAGATTGCTGAACCCTATTGGTGTTACTGGATCAAATCCAAA  1400
      ||  |||||||||||||||||||||||||||||||||||||||||||||
1351  GGACTAGAAGATTGCTGAACCCTATTGGTGTTACTGGATCAAATCCAAA  1400

1401  TAAAGAAACTCCATGCTTAGAGTTGGAGTTTGACTGGTTCAGCAGTGTGG  1450
      |||||||||||||||| ||| |||||||||||||||||||||||||||||
1401  TAAAGAAACTCCATGTTTAGAGTTGGAGTTTGACTGGTTCAGCAGTGTGG  1450
```

FIG. 17G

```
1451  TAAAGTTCCCAGATATGTCAGTGATTGAAGAGCATGCCAATTGGTCTGTA  1500
      |||||  ||||||||||||||||||||||||||||||||||||||||||||
1451  TAAAGTTTCCAGATATGTCAGTGATTGAAGAGCATGCCAATTGGTCTGTA  1500

1501  TCCCGAGAAGCAGGATTTAGCTATTCCCACGCAGGACTGAGTAACAGACT  1550
      ||||  ||||||||||||| | ||||||||  ||||||||||||||||||
1501  TCCCGTGAAGCAGGATTTAGTTATTCCCATGCAGGACTGAGTAACAGACT  1550

1551  AGCTAGAGACAATGAATTAAGGAAAATGACAAAGAACAGCTCAAAGCAA   1600
      |||||||||||||||||||| |||| ||||||||||||||| |||||||
1551  AGCTAGAGACAATGAATTAAGAGAAAATGATAAAGAACAGCTCCGAGCAA  1600

1601  TTTCTACGAGATCCCTCTCTGAAATCACTGAGCAGGAGAAAGATTT      1650
      || ||||||||||||| |||||||||||||||||||||||||||||
1601  TTTGTACGAGATCCCTCTATCTGAAATCACTGAGCAAGAGAAAGATTTT  1650

1651  CTATGGAGTCACAGACACTATTGTGTAACTATCCCCGAAATTCTACCCAA  1700
      || |||||||||||||||||||||||||||||||||||||||||||||||
1651  CTGTGGAGCCACAGACACTATTGTGTAACTATCCCCGAAATTCTACCCAA  1700
```

FIG. 17H

```
1701 ATTGCTTCTGTCTGTTAAATGGAATTCTAGAGATGAAGTAGCCCAGATGT 1750
     ||||||||||||||||||||||||||||||||||||||||||||||||||
1701 ATTGCTTCTGTCTGTTAAATGGAACTCTAGAGATGAAGTAGCTCAGATGT 1750

1751 ATTGCTTGGTAAAAGATTGGCCCTCCAATCAAACCTGAACAGGCTATGGAA 1800
     |||||||| ||||||||||||||||||||||||||||||||||||||||
1751 ACTGCTTGGTAAAAGATTGGCCCTCCAATCAAGCCTGAACAGGCTATGGAG 1800

1801 CTTCTGGACTGTGTAATTACCCAGATCCTATGGTTCGAGGTTTTGCTGTTCG 1850
     |||||||||||| ||||| ||||||||||||||||||||||||||||||
1801 CTTCTGGACTGTTACAATTACCCAGATCCTATGGTTCGAGGTTTTGCTGTTCG 1850

1851 GTGCTTGGAAAAATATTTAACAGATGACAAACTTTCTCAGTATTTAATTC 1900
     |||||| ||||  |||||||||||||||||||||||| |||||| |||||
1851 GTGCTTAGAAAAATATTTAACAGATGACAAACTTTCTCAGTACCTAATTC 1900

1901 AGCTAGTACAGGTCCTAAAAATGAACAATATATTTGGATAACTTGCTTGTG 1950
     |||||||||||| |||||||||||||||| ||| |||||||||||||||
1901 AGCTAGTACAGGTACTAAAAATGAACAGTATTTGGATAACCTGCTTGTG 1950
```

FIG. 17I

```
1951  AGATTTTTACTGAAGAAAGCATTGACTAATCAAAGGATTGGGCACTTTTT  2000
      |||||||||||||||||  ||  ||||  ||  ||||||||  ||||||||
1951  AGATTTTTACTGAAGAAAAAGCGTTAACTAATCAAAGGATCGGTCACTTTTT 2000

2001  CTTTTGGCATTTAAAATCTGAGATGCACAATAAAAACAGTTAGCCAGAGGT  2050
      ||||||||||||||||||||||||||||||||||||||||| ||||||||
2001  CTTTTGGCATTTAAAATCTGAGATGCACAATAAAAACAGTTAGTCAGAGGT  2050

2051  TTGGCCTGCTTTTGGAGTCCCTATTGTCGTGCATGTGGGATGTATTTGAAG  2100
      |||||||||||||||||||||||||| |||||||||||||||| ||||||
2051  TTGGCCTGCTTTTGGAGTCCCTATTGCCGTGCATGTGGGATGTATCTGAAG  2100

2101  CACCTGAATAGGCAAGTCGAGGCAATGGAAAAGCTCATTAACTTAACTGA  2150
      ||||| |||||||||||| |||  |||| |||||||||||||||| ||||
2101  CACCTTAATAGGCAAGTTGAGGCTATGGAAGAAGCTCATTAACTTGACTGA  2150

2151  CATTCTCAAACAGGAGAAGGAAGGATGAAACACAAAAGGTACAGATGAAGT  2200
      ||||||||||| || ||| |||||||||||  ||||||||||||||||||
2151  CATTCTCAAACAAGAGAAGAAGGATGAAACACAAAAGGTACAGATGAAGT  2200
```

FIG. 17J

```
2201  TTTTAGTTGAGCAAATGAGGCGACCAGATTTCATGGATGCCCTACAGGGC  2250
      |||||||||||||||||||| ||||||||||||||||||||| |||||||
2201  TTTTAGTTGAGCAAATGCGGCGACCAGATTTCATGGATGCTCTCCAGGGC  2250

2251  TTGCTGTCTCCTCTAAACCCTGCTCATCAACTAGGAAACCTCAGGCTTAA  2300
      || ||||||||||||||||||||||||||| || |||||| |||||| |
2251  TTTCTGTCTCCTCTAAACCCTGCTCATCAGCTGGGAAATCTCAGGCTTGA  2300

2301  AGAGTGTCGAATTATGTCTTCTGCAAAAAGGCCACTGTGGTTGAATTGGG  2350
      |||||||||||||||||||||||||||||||||||||||||||||||||
2301  AGAGTGTCGAATTATGTCTTCTGCAAAAAGGCCACTGTGGTTGAATTGGG  2350

2351  AGAACCCCAGACATCATGTCAGAGTTACTGTTTCAGAACAATGAGATCATC  2400
      |||||||||||||||||||||||||| ||||||||||||||||||||||
2351  AGAACCCCAGACATCATGTCAGAATTACTCTTTCAGAACAATGAGATCATC  2400

2401  TTTAAAAATGGGGATGATTTACGGCAAGATATGCTAACACTTCAAATTAT  2450
      |||||||||||||||||||||||||||||||||||||| |||||| |||
2401  TTTAAAAATGGGGATGATTTACGGCAAGATATGCTAACCCTTCAGATTAT  2450
```

FIG. 17K

```
2451  TCGTATTATGGAAAATATCTGGCAAAATCAAGGTCTCTTGATCTTCGAATGT  2500
      ||| ||||||||||||||||||||||||||||||||||||||||||||||
2451  TCGCATTATGGAAAATATCTGGCAAAATCAAGGTCTCTTGATCTTCGAATGT  2500

2501  TACCTTATGGTTGTCTGTCAATCGGTGACTGTGTGGGACTTATTGAGGTG   2550
      ||||||||| ||| ||||||||||||||||||||||||||| ||||||
2501  TACCTTATGGATGTCTGTCAATCGGTGACTGTGTGGGACTTATCGAGGTG   2550

2551  GTGCGAAATTCTCACACTATTATGCAAATTCAGTGCAAAGGGCGGCTTGAA  2600
      || ||||||||||||||| |||| |||||||||| ||| ||||||||||
2551  GTGAGAAATTCTCACACTATAATGCAGATTCAGTGTAAAGGAGGCCTGAA   2600

2601  AGGTGCACTGCAGTTCAACAGCCACACTACATCAGTGGCTCAAAGACA    2650
      |||||||||||||||| |||| ||||| |||||||||||||||||||
2601  AGGTGCACTGCAGTTTAACAGCCACACACTCCATCAGTGGCTCAAAGACA   2650

2651  AGAACAAAGGAGAAATATGATGCAGCCATTGACCTGTTTACACGTTCA    2700
      ||||||||| ||| ||||||||||| |||||||||||||||| || ||
2651  AGAACAAGGGGAAATATATGATGCGGCCATCGATTTGTTTACACGATCA   2700
```

FIG. 17L

```
2701  TGTGCTGGATACTGTGTAGCTACCTTCATTTTGGGAATTGGAGATCGTCA  2750
      ||||||||||||||||||| |||||| |||||||||||||||||||||||
2701  TGTGCTGGATATTGTGTTGCCACCTTCATTTTGGGAATTGGAGATCGTCA  2750

2751  CAATAGTAACATCATGGTTGAAAGACGATGGACAACTGTTTCATATAGATT  2800
      |||||||| |||||||||||||| |||||||||||||||||||||||||
2751  CAATAGTAATATCATGGTTAAAGATGATGGACAACTGTTTCATATAGATT  2800

2801  TTGGACACTTTTTTGGATCACAAGAAGAAAAAATTGGTTATAAACGAGAA  2850
      |||||||||||| |||||||||||||||||||||||||||||||||||
2801  TTGGACACTTTTTTGGATCACAAGAAGAAAAAATTGGTTATAAACGAGAG  2850

2851  CGTGTGCCATTTGTTTTGACACAGGATTCTTAATAGTGATTAGTAAAGG  2900
      || ||||||||||| ||||||||| |||||||||||||||||||||||||
2851  CGCGTGCCGTTTGTTTTGACACAAGATTTCTTAATAGTGATTAGTAAAGG  2900

2901  AGCCCAAGAATGCACAAAGACAAGAGAATTTGAGAGGTTTCAGGAGATGT  2950
      ||||||||||||||||||||||||||||||||||||||||||||||||||
2901  AGCCCAAGAATGCACAAAGACAAGAGAATTTGAGAGGTTTCAGGAGATGT  2950
```

FIG. 17M

```
2951 GTTACAAGGCTTATCTAGCTATTCGACAGCATGCCAATCTCTTCATAAAT 3000
     ||||||||||||||||||||||||||||||||||||||||||||||||||
2951 GTTACAAGGCTTATCTAGCTATTCGGCAGCATGCCAATCTCTTCATAAAT 3000

3001 CTTTTCTCAATGATGCTTGGCTCTGGAATGCCAGAACTACAATCTTTTGA 3050
     ||||||||||||||||||||||||||||||||||||||||||||||||||
3001 CTTTTCTCAATGATGCTTGGCTCTGGAATGCCAGAACTGCAATCTTTTGA 3050

3051 TGACATTGCATACATTCGAAAGACCCCTAGCCTTTAGATAAAACTGAGCAAG 3100
     ||||||||||||||||||||||||||||||||||||||||||||||||||
3051 TGATATTGCATACATTCGAAAGACCCCTAGCTTTTAGATAAAACTGAGCAAG 3100

3101 AGGCTTTGGAGTATTTCATGAAACAAATGAATGATGCACATCATGGTGGC 3150
     ||||||||||||||||||||||||||||||||||||||||||||||||||
3101 AGGCTTTGGAGTATTTCATGAAACAAATGAATGATGCACACCATGGTGGC 3150

3151 TGGACAACAAAAATGGATTGGATCTTCCACACAATTAAACAGCATGCATT 3200
     ||||||||||||||||||||||||||||||||||||||||||||||||||
3151 TGGACAACAAAAAATGGATTGGATCTTCCACACAATTAAGCAGCATGCTTT 3200

3201 GAACTGAAAGATAACTGAGAAAATGAAAGCTCACTCTGGA
     ||||||||
3201 GAACTGA..
```

FIG. 18A

```
              10        20        30        40        50        60
h  MPPRPSSGELWGIHLMPPRILVECLLPNGMIVTLECLREATLVTIKHELFKEARKYPLHQ
   ||||||||||||||||||||||||||||||||||||||:|||||||||||||||||||
b  MPPRPSSGELWGIHLMPPRILVECLLPNGMIVTLECLREATLITIKHELFKEARKYPLHQ
              10        20        30        40        50        60

70        80        90       100       110       120
h  LLQDESSYIFVSVTQEAEREEFFDETRRLCDLRLFQPFLKVIEPVGNREEKILNREIGFA
   ||||||||||||||||||||||||||||||||||||||||||||||||||||||||||
b  LLQDESSYIFVSVTQEAEREEFFDETRRLCDLRLFQPFLKVIEPVGNREEKILNREIGFA
              70        80        90       100       110       120

130       140       150       160       170       180
h  IGMPVCEFDMVKDPEVQDFRRNILNVCKEAVDLRDLNSPHSRAMYVYPPHVESSPELPKH
   |||||||||||||||||||||||||||||||||||||||||||||||:|||||||||||
b  IGMPVCEFDMVKDPEVQDFRRNILNVCKEAVDLRDLNSPHSRAMYVYPPNVESSPELPKH
             130       140       150       160       170       180
```

FIG. 18B

```
          190        200        210        220        230        240
h  IYNKLDRGQIIVVIWVIVSPNNDKQYTLKINHDCVPEQVIAEAIRKKTRSMLLSSEQLK
   ||||||:|||||||||||||||||||||||||||||||||||||||||||||||||||
b  IYNKLDKGQIIVVIWVIVSPNNDKQYTLKINHDCVPEQVIAEAIRKKTRSMLLSSEQLK
          190        200        210        220        230        240

250        260        270        280        290        300
h  LCVLEYQGKYILKVCGCDEYFLEKYPLSQYKYIRSCIMLGRMPNLKMMAKESLYSQLPMD
   |||||||||||||||||||||||||||||||||||||||||::|||||||||||||||
b  LCVLEYQGKYILKVCGCDEYFLEKYPLSQYKYIRSCIMLGRMPNLMLMAKESLYSQLPMD
          250        260        270        280        290        300

310        320        330        340        350        360
h  CFTMPSYSRRISTATPYMNGETSTKSLWVINRALRIKILCATYVNLNIRDIDKIYVRTGI
   |||||||||||||||||||||||||||||||||:|||||||||::|||||||||||||
b  CFTMPSYSRRISTATPYMNGETSTKSLWVINSALRIKILCATYVNVNIRDIDKIYVRTGI
          310        320        330        340        350        360
```

FIG. 18C

```
              370        380        390        400        410        420
h  YHGGEPLCDNVNTQRVPCSNPRWNEWLNYDIYIPDLPRAARLCLSICSVKGRKGAKEEHC
   ||||||||||||||||||||||||||||||||||||||||||||||||||||||||||||
b  YHGGEPLCDNVNTQRVPCSNPRWNEWLNYDIYIPDLPRAARLCLSICSVKGRKGAKEEHC
              370        380        390        400        410        420

430        440        450        460        470        480
h  PLAWGNINLFDYTDTLVSGKMALNLWPVPHGLEDLLNPIGVTGSNPNKETPCLELEFDWF
   ||||||||||||||||||||||||||||||||||||||||||||||||||||||||||||
b  PLAWGNINLFDYTDTLVSGKMALNLWPVPHGLEDLLNPIGVTGSNPNKETPCLELEFDWF
              430        440        450        460        470        480

490        500        510        520        530        540
h  SSVVKFPDMSVIEEHANWSVSREAGFSYSHAGLSNRLARDNELRENDKEQLKAISTRDPL
   |||||||||||||||||||||||||||||||||||||||||||||||| :||||||||||
b  SSVVKFPDMSVIEEHANWSVSREAGFSYSHAGLSNRLARDNELRENDKEQLRAICTRDPL
              490        500        510        520        530        540
```

FIG. 18D

```
           550              560              570              580              590              600
h  SEITEQEKDFLWSHRHYCVTIPEILPKLLLSVKWNSRDEVAQMYCLVKDWPPIKPEQAME
   |||||||||||||||||||||||||||||||||||||||||||||||||||||||||||
b  SEITEQEKDFLWSHRHYCVTIPEILPKLLLSVKWNSRDEVAQMYCLVKDWPPIKPEQAME
           550              560              570              580              590              600

610              620              630              640              650              660
h  LLDCNYPDPMVRGFAVRCLEKYLTDDKLSQYLIQLVQVLKYEQYLDNLLVRFLLKKALTN
   |||||||||||||||||||||||||||||||||||||||||||||||||||||||||||
b  LLDCNYPDPMVRGFAVRCLEKYLTDDKLSQYLIQLVQVLKYEQYLDNLLVRFLLKKALTN
           610              620              630              640              650              660

670              680              690              700              710              720
h  QRIGHFFWHLKSEMHNKTVSQRFGLLLESYCRACGMYLKHLNRQVEAMEKLINLTDILK
   ||||||||||||||||||||||||||||||||||||||||||||||||||||||||||
b  QRIGHFFWHLKSEMHNKTVSQRFGLLLESYCRACGMYLKHLNRQVEAMEKLINLTDILK
           670              680              690              700              710              720
```

FIG. 18E

```
           730                740               750                760               770                780
    h  QERKDETQKVQMKFLVEQMRRPDFMDALQGLLSPLNPAHQLGNLRLKECRIMSSAKRPLW
       |||:|||||||||||||||||||||||||||||||||||:||||||||:|||||||||||
    b  QEKKDETQKVQMKFLVEQMRRPDFMDALQGFLSPLNPAHQLGNLRLEECRIMSSAKRPLW
           730                740               750                760               770                780

790                800               810                820               830                840
    h  LNWENPDIMSELLFQNNEIIFKNGDDLRQDMLTLQIIRIMENIWQNQGLDLRMLPYGCLS
       ||||||||||||||||||||||||||||||||||||||||||||||||||||||||||||
    b  LNWENPDIMSELLFQNNEIIFKNGDDLRQDMLTLQIIRIMENIWQNQGLDLRMLPYGCLS
           790                800               810                820               830                840

850                860               870                880               890                900
    h  IGDCVGLIEVVRNSHTIMQIQCKGGLKGALQFNSHTLHQWLKDKNKGEIYDAAIDLFTRS
       ||||||||||||||||||||||||||||||||||||||||||||||||||||||||||||
    b  IGDCVGLIEVVRNSHTIMQIQCKGGLKGALQFNSHTLHQWLKDKNKGEIYDAAIDLFTRS
           850                860               870                880               890                900
```

FIG. 18F

```
            910       920       930       940       950       960
h  CAGYCVATFILGIGDRHNSNIMVKDDGQLFHIDFGHFLDHKKKFGYKRERVPFVLTQDF
   ||||||||||||||||||||||||||||||||||||||||||||||||||||||||||
b  CAGYCVATFILGIGDRHNSNIMVKDDGQLFHIDFGHFLDHKKKFGYKRERVPFVLTQDF
            910       920       930       940       950       960

970       980       990       1000      1010      1020
h  LIVISKGAQECTKTREFERFQEMCYKAYLAIRQHANLFINLFSMMLGSGMPELQSFDDIA
   ||||||||||||||||||||||||||||||||||||||||||||||||||||||||||
b  LIVISKGAQECTKTREFERFQEMCYKAYLAIRQHANLFINLFSMMLGSGMPELQSFDDIA
            970       980       990       1000      1010      1020

1030      1040      1050      1060      1070      1080
h  YIRKTLALDKTEQEALEYFMKQMNDAHHGGWTTKMDWIFHTIKQHALNXKITEKMKAHSG
   |||||||||||||||||||||||||||||||||||||||||||||||||
b  YIRKTLALDKTEQEALEYFMKQMNDAHHGGWTTKMDWIFHTIKQHALNX
            1030      1040      1050      1060
```

FIG. 19A

```
1    MPPRPSSGEL WGIHLMPPRI LVECLLPNGM IVTLECLRFA TLVTIKHELF
51   KEARKYPLHQ LLQDESSYIF VSVTQEAERE EFFDETRRLC DLRLFQPFLK
101  VIEPVGNREE KILNREIGFA IGMPVCEEFDM VKDPEVQDFR RNILNVCKEA
151  VDLRDLNSPH SRAMYVYPPH VESSPELPKH IYNKLDRGQI IVVIWIVSP
201  NNDKQKYTLK INHDCVPEQV IAEAIRKKTR SMLLSSEQLK LCVLEYQGKY
251  ILKVCGCDEY FLEKYPLSQY KYIRSCIMLG RMPNLKMMAK ESLYSQLPMD
301  CFTMPSYSRR ISTATPYMNG ETSTKSLWVI NRALRIKILC ATYVNLNIRD
351  IDKIYVRTGI YHGGEPLCDN VNTQRVPCSN PRWNEWLNYD IYIPDLPRAA
401  RLCLSICSVK GRKGAKEEHC PLAWGNINLF DYTDTLVSGK MALNLWPVPH
451  GLEDLLNPIG VTGSNPNKET PCLELEFDWE SSVVKFPDMS VIEEHANWSV
```

FIG. 19B

```
 501  SREAGFSYSH AGLSNRLARD NELRENDKEQ LKAISTRDPL SEITEQEKDF
 551  LWSHRHYCVT IPEILPKLLL SVKWNSRDEV AQMYCLVKDW PPIKPEQAME
 601  LLDCNYPDPM VRGFAVRCLE KYLTDDKLSQ YLIQLVQVLK YEQYLDNLLV
 651  RFLLKKALTN QRIGHFFFWH LKSEMHNKTV SQRFGLLLES YCRACGMYLK
 701  HLNRQVEAME KLINLTDILK QERKDETQKV QMKFLVEQMR RPDFMDALQG
 751  LLSPLNPAHQ LGNLRLKECR IMSSAKRPLW LNWENPDIMS ELLFQNNEII
 801  FKNGDDLRQD MLTLQIIRIM ENIWQNQGLD LRMLPYGCLS IGDCVGLIEV
 851  VRNSHTIMQI QCKGGLKGAL QFNSHTLHQW LKDKNKGEIY DAAIDLFTRS
 901  CAGYCVATFI LGIGDRHNSN IMVKDDGQLF HIDFGHFLDH KKKKFGYKRE
 951  RVPFVLTQDF LIVISKGAQE CTKTREFERF QEMCYKAYLA IRQHANLFIN
1001  LFSMMLGSGM PELQSFDDIA YIRKTLALDK TEQEALEYFM KQMNDAHHGG
1051  WTTKMDWIFH TIKQHALN*
```

FIG. 20

```
  1   GGAGACGACTTGCGACAGGATCAACTTATTCTTCAAATCATTTCACTC
      GlyAspAspLeuArgGlnAspGlnLeuIleLeuGlnIleIleSerLeu

49   ATGGACAAGCTGTTACGGAAAGAAAATCTGGACTTGAAATTGACACCT
      MetAspLysLeuLeuArgLysGluAsnLeuAspLeuLysLeuThrPro

97   TATAAGGTGTTAGCCACCAGTACAAAACATGGCTTCATGCAGtTTATC
      TyrLysValLeuAlaThrSerThrLysHisGlyPheMetGlnPheIle

145   CAGTCAGTCCCTGTGGCTGAaGTTCTTGATACAGAGGAAGCATTCAG
      GlnSerValProValAlaGluValLeuAspThrGluGluSerIleGln

193   AACTTTTTAGAAAATATGCACCAAGTGAGAATGGGCCAAATGGGATT
      AsnPhePheArgLysTyrAlaProSerGluAsnGlyProAsnGlyIle

241   AGTGCTGAGGTCATGGACACTtACGTTAAAAGCTGTGCTGGATATTGC
      SerAlaGluValMetAspThrTyrValLysSerCysAlaGlyTyrCys

289   GTGATCACCTATATACTTGGAGTTGGAGACAGGCACCTGGATAACCTT
      ValIleThrTyrIleLeuGlyValGlyAspArgHisLeuAspAsnLeu

337   TTGCTAACCAAAACAGGCAAACTCTTCCACATGATTTCGGCCAC
      LeuLeuThrLysThrGlyLysLeuPheHisIleAspPheGlyHis
```

FIG. 21

```
  1  GGGGATGACTTACGGCAGGACATGCTAACGCTGCAGATGATTCGCATC
     GlyAspAspLeuArgGlnAspMetLeuThrLeuGlnMetIleArgIle

49  ATGAGCAAGATCTGGGTCCAGGAGGGCTGGACATGCCATGGTCATC
     MetSerLysIleTrpValGlnGluGlyLeuAspMetArgMetValIle

97  TTCCGCTGCTTCTCCACCGGCCGGGGCAGAGGGATGGTGGAGATGATC
     PheArgCysPheSerThrGlyArgGlyArgGlyMetValGluMetIle

145  CCTAATGCTGAGACCCTGCTAAGATCCAGGTGGAGCATGGGGTGACC
     ProAsnAlaGluThrLeuArgLysIleGlnValGluHisGlyValThr

193  GGCTCGTTCAAGGACCGGCCCCTGGCAGACCGGCTGCAGAAACACAAC
     GlySerPheLysAspArgProLeuAlaAspArgLeuGlnLysHisAsn

241  CCTGGGGAGGACGAGTATGAGAAGGCTGTGGCAGAACTTTATCTACTCC
     ProGlyGluAspGluTyrGluLysAlaValAlaGluAsnPheIleTyrSer

289  TGCGCTGGCTGCTGCGTGGCCACGTACGTCTTGGCCATCTGTGACCga
     CysAlaGlyCysCysValAlaThrTyrValLeuGlyIleCysAspArg

337  CATAATGACAACATCATGCTGAAGACCACTGGTCACATGTTCCACATC
     HisAsnAspAsnIleMetLeuLysThrThrGlyHisMetPheHisIle

385  GACTTCGGC
     AspPheGly
```

FIG. 22

```
            1                                                    50
vps34       GDDLRQDqLvvQIislMnellknEnvDLkLtPYkiLaTGpqeGaIEfIpN
PITR-c      GDDLRQDqLiLQIIslMdkIlrkEnLDLkLtPYkvLaTstkhGFmqfIqs
hump110     GDDLRQDmLtLQIIriMeniwqnggLDLrMlPYgcLsiGdcvGLIEvVrN
PITR-f      GDDLRQDmLtLQmIriMskiwvqEgLDMrMviFrcFsTGrgrGMVEmIpN
Consensus   GDDLRQD-L-LQII-----M------E-LDL---PY--L-TG---G--IE-I-N 51                                                   100
vps34       dtlasilskyhGIlGy.........LklhypdeNatlgVqgwvlDnFVkSCA
PITR-c      vpvaevldtegsIqnf.........FrkYapseNgpngIsaevmDtYVkSCA
hump110     shtimqiqckgGlkGalqfnshtLhqWlkdkNkge.IydaaiDlFtrSCA
PITR-f      aetlrkiqvehgVtGs..fkdrpLadrlqkhNpgedeyekavEnFIySCA
Consensus   ---------GI-G-----------N-----I-----D-FV-SCA 101                                             133
vps34       GYCViTYILGVGDRHlDNlLvtpdGhFFHaDEG
PITR-c      GYCViTYILGVGDRHlDNlLltktGKlFHIDFG
hump110     GYCVaTFILGIGDRHnsNiMvkddGqLFHIDFG
PITR-f      GCCVaTYVLGIcDRHnDNiMlkttGhMFHIDFG
Consensus   GYCV-TYILG-GDRH-DN------G--LFHIDFG
```

5,824,492

POLYPEPTIDES HAVING KINASE ACTIVITY, THEIR PREPARATION AND USE

This invention relates to new polypeptides which exhibit kinase activity. More specifically, the invention is concerned with polypeptides which show phosphoinositide (hereinafter "PI") 3-kinase activity, particularly molecules involved in pathways responsible for cellular growth and differentiation.

Major advances have taken place in our knowledge of the structure and function of the signal transducing molecules and second messenger systems coupled to cell surface receptors. Thus, a subset of polypeptide growth factor receptors belong to the family of protein-tyrosine kinases (hereinafter "PTK" and activation of these receptors following ligand binding involves autophosphorylation of the receptor as well as phosphorylation of a number of intracellular substrate proteins (reviewed in Ullrich, A et al., 1990). The importance of receptor autophosphorylation had been unclear until recently, when evidence from several laboratories has suggested that this event may mediate the formation of complexes between receptor proteins and putative growth regulatory proteins such as phospholipase Cγ(PLCγ) (Meisenhelder et al, 1989), phosphatidylinositol PI3-kinase (Coughlin, S R et al, 1989), GTPase-activating protein (GAP) (Kaplan et al, 1990), the serine/theonine kinase Raf (Morrison et al, 1989), and members of the src-family of protein-tyrosine kinases (Kypta, R M et al., 1990) (reviewed in Cantley, L C et al., 1991).

The association of PI kinase activity with activated receptors is of particular interest since increased turnover of PI and its phosphorylated derivatives has been implicated in the action of hormones, growth factors and transformation of cells by DNA and RNA viruses (reviewed in Whitman, M et al., 1988; Cantley et al., 1991). Several species of PI kinase are known to exist, but up to now none of these enzymes have been characterised by cloning and expression and the demonstration of PI kinase activity. Fibroblasts contain at least two PI kinase activities which are distinguishable on the basis of their detergent sensitivity and kinetic properties (Whitman, M et al., 1987). These two activities were classified as Type I (inhibited by non-ionic detergents) and Type II (stimulated by non-ionic detergents and inhibited by adenosine). A third distinct species (Type III) has been identified in bovine brain but remains poorly characterised (Enderman, G et al., 1987). One species of PI kinase activity in particular has become of major interest in the search for second messenger systems linked to protein-tyrosine kinases because this activity was shown to co-immunoprecipitate with activated platelet-derived growth factor (PDGF) receptors (Kaplan, D R et al., 1987; Coughlin, S R et al., 1989) and with the polyoma middle T antigen/pp60$^{c\text{-}scr}$ (mT:pp60$^{c\text{-}src}$) complex (Whitman, M et al., 1985). This activity has been shown to be due to a Type I PI kinase which produces novel inositol lipids phosphorylated at the D-3 position of the inositol ring (Whitman, M et al., 1988). More recently this enzyme has also been shown to associate with the CSF-1 receptor (Varticovski, L et al., 1989) kit (Lev et al, 1991), the epidermal growth factor (EGF) receptor (Bjorge et al, 1990), the PDGF α-receptor (Yu et al, 1991), the insulin receptor (Ruderman et al, 1990), the hepatocyte growth factor receptor, Met (Graziani et al, 1991), and with activated non-receptor protein-tyrosine kinases (Fukui & Hanafusa, 1989; Chan et al, 1990; Varticovski et al, 1991).

PI3 kinase activity has been closely linked to the presence of 81/85 kD proteins in these immunoprecipitates which can be phosphorylated on tyrosine residues by the associated protein-tyrosine kinase both in vitro and in vivo (Kaplan, D R et al., 1987; Courtneidge, S A et al., 1987; Cohen et al, 1990). Recently a 650 fold purification of PI3-kinase from bovine brain was described which, among other proteins present in the purest preparation, contained an 85 kD protein which was shown to be an in vitro substrate for the PDGF and EGF receptors (Morgan, S J et al., 1990). Using sequence information from tryptic peptides derived from this protein, two homologous bovine p85 proteins, denoted p85α and p85β (Otsu, M et al., 1991) have recently been cloned. Two other groups have independently cloned murine and human p85α homologues using different strategies (Escobedo, J A et al., 1991b; Skolnik, E Y et al., 1991). Both of these p85 proteins can be demonstrated to bind directly to phosphorylated PDGF receptor in vitro (Otsu, M et al., 1991; Escobedo, J A et al., 1991b). These proteins may function as the receptor binding subunits of the PI3-kinase since neither of them can be shown to encode intrinsic PI3-kinase activity when expressed in a variety of cell systems (Otsu, M et al., 1991; Escobedo, J A et al., 1991b). However, immunoprecipitation of $^{125}$I-labelled bovine brain PI3-kinase with antibodies raised against p85 proteins precipitates an 85 kD protein together with a second protein of molecular weight 110 kD (Otsu, M et al., 1991).

PI3-kinase is one of a growing number of potential signalling proteins which associate with protein-tyrosine kinases activated either by ligand stimulation or as a consequence of cell transformation. A common feature of all these proteins (apart from Raf), is that they contain one or more SH2 domains (src homology) (Koch, C A et al., 1991). Both p85α and p85β proteins contain two SH2 domains. Experiments from a number of laboratories have suggested that these domains may function by binding to peptide sequences usually phosphorylated on tyrosine residues, and thus mediate the complex formation which follows activation of protein-tyrosine kinases (Anderson et al, 1990; Meyer & Hanafusa, 1990; Moran et al, 1990; Matsuda et al, 1991; Meyer et al, 1991; reviewed in Koch, C A et al., 1991). In support of this, several studies suggest that tyrosine phosphorylation of the PDGF receptor or polyoma mT is essential for its association with proteins such as the PI3-kinase (Kazlauskas, A et al., 1989; Talmage, D A et al., 1989) GAP (Kaplan et al, 1990; Kazlauskas, A et al., 1990) and PLCγ (Anderson et al, 1990; Margolis et al, 1990). The precise tyrosine residue required for binding of the PI3-kinase activity (and an 85 kD phosphoprotein) to the human PDGF receptor has been mapped to tyrosine 751 which lies within the kinase insert region of the protein-tyrosine kinase domain (Kazlauskas & Cooper, 1989, 1990; Kazlauskas et al, 1991). The binding sites for other proteins to this receptor (eg., PLCγ, GAP and src-family kinases) have yet to be mapped, but these proteins may associate via other phosphorylated tyrosine residues.

This invention has been facilitated by the finding that certain synthesized peptides from the human PDGF β-receptor, namely peptides derived from the sequence around tyrosine 751 of the PDGF receptor, can be used to bind and isolate bovine brain PI3-kinase, making it possible to purify further partially purified bovine brain PI3-kinase (as described by Morgan et al, 1990) to apparent homogeneity and to obtain reasonably pure p110 protein. As will be described hereinafter, the PI3- kinase requires a phosphopeptide column containing a YXXM motif for its isolation by such a technique, the tyrosine being phosphorylated. Only if a column of this type is used are both the 85 kD and 110 kD proteins secured whereas 85 kD subunit binds to all phosphopeptide affinity columns tested and only fails to bind to non-phosphorylated peptides. Moreover, the relatively small size of the phosphopeptides used for such columns gives good specificity and a high density of affinity groups per unit volume of column.

This purification has allowed amino acid sequence information to be provided, and cDNA cloning to be performed. Such cloning has revealed some interesting facts. Thus, p110 is a 1068 amino acid protein having an unexpectedly high (compared to SDS-PAGE Figures) calculated molecular weight of about 124 kD (124247). The protein is related to Vps34p, a Saccharomyces cerevisiae protein involved in the sorting of proteins to the vacuole. Surprisingly, p110 when expressed in COS-1 cells was inactive and activity was only seen when complexed with p85. However, when expressed in insect cells, p110 could be shown to possess intrinsic kinase activity. The novel p110 polypeptide can be associated with p85α into an active p85α/p110 complex which binds the activated colony stimulating factor-1 receptor. The invention is also based upon these discoveries and unpredictable findings.

Thus, in one aspect the present invention provides an isolated polypeptide of calculated molecular weight approximately 124 kD which possesses PI3-kinase activity when produced by recombinant production in insect cells, or a polypeptide derivable therefrom which has PI3-kinase activity and binds, when associated with a p85 mammalian PI3 kinase subunit, to a phosphopeptide which includes the YXXM motif, the tyrosine being phosphorylated. Such polypeptides are preferably those capable of association with p85 subunits of mammalian PI3-kinases to produce active p85/p110 complexes. Preferably, the polypeptides have either the amino acid sequence of FIG. 9 hereof or exhibit significant sequence homology therewith. Preferred are polypeptides having at least amino acids 272 to 1068 of the sequence of FIG. 9 hereof. As used herein, the term "PI3-kinase activity" means phosphoinositide-3 kinase activity.

The invention embraces polypeptides as defined and exhibiting sequence homology with any chosen mammalian species of PI3-kinase. A human sequence is given in FIG. 16 hereof. Amino acids 37(tyr)-834 (stop codon) (see FIG. 16) are >99% conserved with the bovine p110 cDNA sequence and correspond to amino acids 272–1069 (stop codon) of the sequence of FIG. 9. Upstream of amino acid 37 (human sequence) there is no sequence similarity between the p110 cDNA sequences from the two species.

The invention includes antibodies, monoclonal or otherwise, against the polypeptides of the invention.

In another aspect the invention includes a DNA sequence comprising either: (a) a sequence set out in FIG. 9 hereof; (b) any one of the subsequences A to N of FIG. 9 hereof; (c) the sequence represented by bases 816 to 3204 of FIG. 9 hereof; (d) a sequence set out in FIG. 16 hereof; or (e) a DNA sequence hybridizable to (a), (b), (c) or (d); which sequence (a), (b), (c), (d) or (e) encodes a polypeptide which has PI3-kinase activity if expressed in insect cells or can complex with a p85 mammalian PI3-kinase subunit to produce such activity. Subsequences A to N, referred to above, are themselves part of the present invention.

Hybridization conditions which may be used to find active sequences include, but are not limited to, 1 M NaCl/10×Denhardt's solution/50 mM Tri-HCl (pH 7.4)/10 mM EDTA/0.1% SDS/100 µg/ml denatured herring sperm DNA (Sigma) at 65° C. for 16 h, with the following washing conditions, i.e. 2×SSC/0.1% SDS, 42° C.→0.5 ×SSC/0.1% SDS, 50° C.→0.1 ×SSC/0.1% SDS, 65° C.→0.1 ×SSC/0.1% SDS, 68° C.

The invention further provides a DNA construct comprising a DNA sequence as defined above under the control of a control sequence and in proper reading frame in an expression vector.

The control sequence may include a regulatable promoter (e.g. Trp). Selected host cells which have been genetically altered to permit expression of the encoded polypeptide by the incorporation of such a construct are another aspect of the invention, and the invention also includes both a method of making such a polypeptide by cultivating such host cells and, of course, the resulting polypeptides.

In general, new polypeptides of the invention can be used to provide PI3-kinase activity, either directly or after complexing with a mammalian p85 subunit. Enzymatically active complexes involving the above-defined polypeptides are part of the invention.

The invention envisages a method of prophylaxis or therapy which involves the encouragement or discouragement of cell proliferation by the action of an agonist or antagonist, respectively, for the PI3-kinase activity of a polypeptide of the invention or complex including the same, wherein said cell proliferation is mediated through a cell surface receptor interactive with said activity. The present invention opens up for the first time, by providing pure sequenced active protein, the opportunity to screen (using standard techniques) for such agonists or antagonists.

Another aspect of the invention is a pharmaceutical or veterinary formulation comprising an agonist or antagonist as defined above formulated for pharmaceutical or veterinary use, respectively, optionally together with an acceptable diluent, carrier or excipient and/or in unit dosage form. Conventional pharmaceutical or veterinary practice may be employed to provide suitable formulations or compositions.

Thus, the formulations of this invention can be applied to parenteral administration, for example, intravenous, subcutaneous, intramuscular, intraorbital, ophthalmic, intraventricular, intracranial, intracapsular, intraspinal, intracisternal, intraperiotoneal, topical, intranasal, aerosol, scarification, and also oral, buccal, rectal or vaginal administration.

Parenteral formulations may be in the form of liquid solutions or suspensions; for oral administration, formulations may be in the form of tablets or capsules; and for intranasal formulations, in the form of powders, nasal drops, or aerosols.

Methods well known in the art for making formulations are to be found in, for example, "Remington's Pharmaceutical Sciences". Formulations for parenteral administration may, for example, contain as excipients sterile water or saline, polyalkylene glycols such as polyethylene glycol, oils of vegetable origin, or hydrogenated naphthalenes. Biocompatible, biodegradable lactide polymers, lactide/glycolide copolymers, or polyoxyethylene-polyoxypropylene copolymers may be used to control the release of the present factors. Other potentially useful parenteral delievery systems for the factors include ethylene-vinyl acetate copolymer particles, osmotic pumps, implantable infusion systems, and liposomes. Formulations for inhalation may contain as excipients, for example, lactose, or may be aqueous solutions containing, for example, lactose or may be aqueous solutions containing, for example, polyoxyethylene-9-lauryl ether, glycocholate and deoxycholate, or may be oily solutions for administration in the form of nasal drops, or as a gel to be applied intranasally. Formulations for parenteral administration may also include glycocholate for buccal administration, methoxysalicylate for rectal administration, or citric acid for vaginal administration.

The concentration of PI3-kinase agonist or antagonist in the formulations of the invention will vary depending upon a number of issues, including the dosage to be administered, and the route of administration.

In general terms, such agonists or antagonists may be provided in an aqueous physiological buffer solution containing about 0.1 to 10% w/v compound for parenteral administration. General dose ranges are from about 1 μg/kg to about 1 g/kg of body weight per day; a preferred dose range is from about 0.01 mg/kg to 100 mg/kg of body weight per day. The preferred dosage to be administered is likely to depend upon the type and extent of progression of the condition being addressed, the overall health of the patient, the make up of the formulation, and the route of administration.

The invention also includes the use of a polypeptide of the invention, or active complex containing the same, or an agonist or antagonist thereof in affecting the level of stimulation of platelets or neutrophils or in regulating blood glucose levels (the action of insulin may be mediated by PI3-kinase activity), and such use when employed for prophylactic or therapeutic purposes is envisaged.

The polypeptides of the invention (or complexes containing them) have a particular utility in the in vitro enzymatic production of 3-phosphorylated phosphoinositides eg PI(3)P, PI(3,4)P2, PI(3,4,5)P3). Such materials are of considerable biochemical interest, and are often very difficult to synthesize by conventional chemical techniques. This invention provides, for the first time, appreciable amounts of purified and reliable enzymatic activity for such in vitro synthesis.

In general, the first step in the purification and cloning upon which the invention is based involved partial purification of PI3-kinase from bovine brain as previously described (Morgan et al, 1990) and then further purification by affinity chromatography on an immobilised 17 amino acid phosphotyrosine peptide whose sequence is based on that surrounding tyrosine 751 of the human PDGF-β receptor. Following this final purification, p110 and p85 were eluted from the resin with SDS-containing buffers. The p85/p110 mixture was either digested directly with lysylendopeptidase, or p110 was further purified by SDS-agarose gel electrophoresis (see below) and digested following elution from the gel. Peptides were separated by reverse phase HPLC and sequenced using a modified Applied Biosystems 477A sequencer. Amino acid sequence analysis of 14 peptides (A to N, FIG. 9) generated 235 residues which could be assigned with certainty (see FIG. 9, attached).

It is important to note that the successful production of sequence information herein was dependent upon a novel SDS-agarose gel electrophoresis technique. Although, SDS-PAGE is widely used for high resolution protein separations, and is a method which resolves components primarily by their differences in molecular weight, as the polyacrylamide matrix is not readily disrupted, protein recovery following SDS-PAGE generally requires techniques involving electroelution from gel slices, electroblotting, or passive diffusion. Elution of proteins from polyacrylamide gels that have been previously stained using sensitive reagents (such as Coomassie Blue) is slow and recoveries are frequently low. Furthermore, these methods may concentrate impurities present in the polyacrylamide matrix and in the relatively large buffer volumes required for elution. Preparative SDS-PAGE systems using continuous flow collection have also been developed, but these frequently exhibit decreased resolution and low recoveries.

The novel method employed herein uses SDS-agarose gel electrophoresis (SDS-AGE) and allows a combination of the high resolving capacity of slab gel electrophoresis and the detection of proteins using sensitive stains with a rapid recovery technique that isolates proteins in high yield and in small volumes. The recovered protein is highly purified and in a form that can be either readily precipitated or digested directly in SDS containing buffers. Peptides produced by this method can be fractionated by HPLC and then analysed by automated amino acid sequencing. The recovery of long hydrophobic peptides is particularly efficient using these digestion conditions. The following protocol guides the skilled reader.

PROTOCOL

Materials

All chemicals should be of analytical or purer grades. Guanidinium hydrochloride was Aristar grade (BDH, UK). FMC Prosieve was purchased from Flowgen (UK) and ultrapure agarose was from BRL (USA). Other electrophoresis reagents were from Biorad (UK, Electrophoresis grade). Standard molecular weight proteins were from Bio-Rad (UK) and Amersham International (UK). Sequencing grade trypsin (porcine, EC 3.4.21.4) was from Boehringer Mannheim (UK) and lysylendopeptidase (Achromobacter lyticus, EC 3.4.21.50) was from Wako Chemicals GmbH (Germany). Glass capillaries were those supplied by Applied Biosystems Inc (USA) for use on the 430A HPLC system, but were frosted by abrasion with an aqueous carborundum suspension (C150 grade) and a steel rod. Frosted slab gel plates were obtained from Hoefer (UK).

Slab SDS-AGE

Slab Prosieve resolving gels of 0.75 or 1.5 mm thickness were poured essentially as described by the manufacturer using pairs of 16×18 cm glass plates, one of which was frosted in order to prevent the gel from slipping out of the electrophoresis assembly. It is important to ensure that the gel plates be thoroughly warmed to 60° C. prior to pouring the resolving gel. The inability to warm the gel plates prior to pouring an agarose stacking gel, the insertion of the comb into a rapidly cooling gel, and the removal of the comb from the fragile agarose stacking gel initially caused severe problems. In order to remove these difficulties a 5% T, 2.6% C polyacrylamide stacking gel was used in place of agarose in later preparations.

Samples were denatured at 100° C. in sample buffer (190 mM Tris/HCl, pH 6.8, 6% (w/v) SDS, 30% (v/v) glycerol, 10 mM DTT, 0.01% (w/v) bromophenol blue) and gels were run using Laemmli cathode buffer (0.192 M glycine, 0.025 M Tris, 0.1% (w/v) SDS) with a modified anode buffer (1 M Tris/HCl, pH 8.3) at 200 v (approximately 50 mA for 1.5 mm and 25 mA for 0.75 mm gels) for about 4 h using a SE400 gel apparatus (Hoefer, USA). Gels were stained using either Coomassie Blue G-250 (Bio-Rad, UK) with rapid destaining or 4 M ammonium acetate solution. In the latter case proteins were identified within a few minutes by optical contrast using incident light reflection observed against a dark background. Protein bands were immediately excised and gel slices stored at −20° C.

HPEC Electroelution

Gel slices were thawed and washed twice in 1 ml of 62.5 mM Tris/HCl, pH 6.8 for 5 min each at 20° C. Slices containing Coomassie Blue were prewashed with 1 ml of 50% (v/v) methanol, 5% (v/v) acetic acid for 5 min at 20° C.

The volume of the gel slice was estimated, then 10% SDS and 20% DTT were added to final concentrations of 2% and 0.2% (w/v) respectively. The gel slice was melted and homogenized by immersion in boiling water for 5 min with occasional mixing. The sample volume was then measured and made up to the required amount (see Table 1 below) with prewarmed 62.5 mM Tris/HCl, pH 6.8. The diluted sample was heated for a further 5 min and loaded into a prewarmed glass HPEC capillary. It was important not to exceed 90% of the capillary volume at this stage. The capillary was incubated at 4° C. for at least 10 min to allow the sample gel to solidify, before the slow addition of 0.8% agarose, 1 M Tris/HCl, pH 8.8 to overfill the capillary. After a further 10 min at 4° C., the ends of the gel were trimmed flush, sealed with Zytex discs, and applied to an Applied Biosystems 230A HPEC system. Electroelution was performed using an elution buffer pressure of 2.5 psi (generating a flow rate of approximately 1 $\mu$l/min), an upper reservoir buffer pressure of 3.5 psi and a lower reservoir buffer pressure of 0.9 psi. These settings were changed from the manufacturer's recommendations in order to stop the gel from collapsing upwards during the run. The current settings were as described in the text and 3 min fractions were collected while monitoring the eluate at 280 nm. The fraction collector rack was cooled to 4° C. and the gel compartment was cooled to 10° C.

TABLE 1

HPEC Elution Gel Parameters

| Capillary size (mm) | | Gel volume ($\mu$l)[a] | | | Current |
| --- | --- | --- | --- | --- | --- |
| Length | i.d.[a] | Total | Sample | Focussing | (mA) |
| 50 | 2.5 | 245 | 220 | 25 | 1,0–1.5 |
| 50 | 3.5 | 480 | 432 | 48 | 1.5 |
| 100 | 2.5 | 491 | 441 | 49 | 2.0–2.5 |
| 100 | 3.5 | 960 | 864 | 96 | 2.5 |

[a]These values are underestimated due to the variable increase in the internal diameter of the capillaries caused by the frosting procedure.

These values are underestimated due to the variable increase in the internal diameter of the capillaries caused by the frosting procedure.

Preparation of Proteins for Sequence Analysis

Fractions were assayed for protein content and purity either by monitoring radioactivity or by SDS-PAGE and silver staining. Samples required for trypsin or lysylendopeptidase digestion and subsequence sequence analysis were separated from Coomassie Blue by sequential precipitation on ice using 10% (w/v) TCA and then 20% TCA with centrifugation for 10 min at 4° C. Pellets were washed with 1 ml of acetone at –20° C. overnight and then washed again briefly in order to remove trace contamination by TCA and SDS before air drying and the addition of the required digestion buffer. Tryptic digestions were performed in 0.1 M Tris/HCl, pH 8.0 at 37° C. and lyslendopeptidase digestions in 20 mM Tris/HCl, pH 8.8 containing 0.1% (w/v) SDS at 30° C. Solid guanidinium hydrochloride was added to tryptic digests (6 M final concentration) and incubated for 1 h at 37° C. Products were applied directly to HPLC columns using a Hewlett-Packard 1090M system and the effluent was monitored with a 79880A diode array detector. Trypsin digests were fractionated using an Applied Biosystems RP-300 column (2.1×100 mm) while lysylendopeptidase products required an Applied Biosystems AX-300 (2.1–30 mm) and an OD-300 column (2.1×100 mm) connected in series essentially as described by Kawasaki and Suzuki (1990).

The following Examples are given to illustrate the present invention without limiting the same. The Examples refer to the accompanying drawings.

In the accompanying drawings:

FIGS. 1 to 9 are concerned with Example 1, sections A and B.

FIG. 1. Phosphorylation and purification of Y751 phosphopeptide.

Panel A. HPLC profile for separation of the phosphorylated from the non-phosphorylated Y751 peptide on a $C_{18}$ reverse phase column. The trace shows the spectra monitored at 214 nm during the course of the elution. The peaks corresponding to the phosphorylated and non-phosphorylated peptide are indicated by arrows. The small peaks observed are derived from the A431 membranes.

Panel B. Spectral analysis of the purified phosphorylated and non-phosphorylated Y751 peptides between 240 and 300 nm as measured by the diode-array detector. The absorption maximum for the peptide is observed to shift to a lower wavelength following tyrosine phosphorylation.

Panel C. Phosphoamino acid analysis of Y751 peptide phosphorylated by either purified EGF receptor (left panel) or A431 cell membranes (right panel). Following the phosphorylation reaction the phosphopeptide was purified by reverse phase HPLC. The peptide was subjected to acid hydrolysis and the phosphoamino acids separated by two-dimensional thin layer electrophoresis. Internal standards were stained with ninhydrin and the $^{32}$P-labelled phosphoamino acids were detected by autoradiography. The positions of inorganic phosphate ($P_i$), and phosphoserine (S), phosphothreonine (T) and phosphotyrosine (Y) standards are indicated.

FIG. 2. Purification of PI 3-kinase complex on the Y751 phosphopeptide affinity column.

Panel A. Peak 1 (P1) and peak 2 (P2) of PI 3- kinase fractions from the second MonoQ step were analysed on a 7.5% SDS-PAGE gel. Proteins in these two peak fractions were visualised by silver staining. The migration positions of molecular weight markers are indicated.

Panel B. Affinity purification of peak 1 (P1) and peak 2 (P2) PI 3-kinase using the Y751 phosphopeptide column. Silver stain of a 7.5% SDS-PAGE gel showing PI 3-kinase associated proteins from MonoQ P1 and P2 which bound to, and were eluted from, the Y751 phosphopeptide column with 0.1% SDS-containing phosphate buffer at 80° C. Lanes 1, 2 and 3 for both the P1 and P2 material indicates the proteins eluted by successive 50 $\mu$l elutions.

Figure 3:
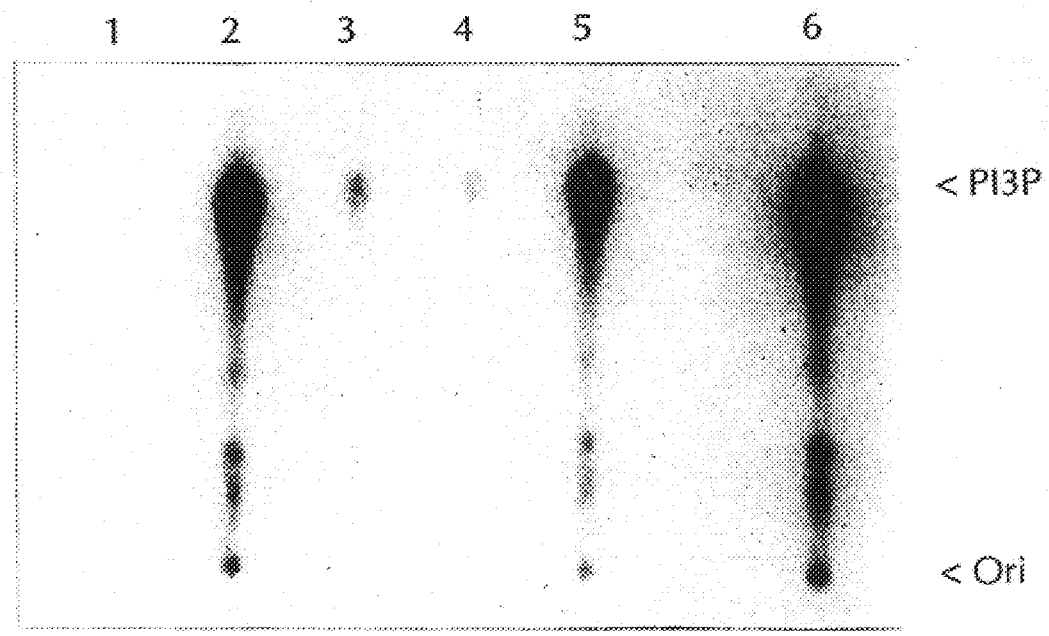

FIG. 3. Characterisation of the binding of PI 3-kinase activity to Y751 derived peptide columns.

One microgram of partially purified peak 1 bovine brain PI 3-kinase was applied to 10 $\mu$l of the Y751 derived peptide resins in 100 $\mu$l of binding buffer. Bound proteins were assayed for PI 3-kinase activity. Lane 1, PI 3-kinase activity bound to non-phosphorylated Y751 column. Lane 2, PI 3-kinase activity bound to phosphorylated Y751 column. Lane 3, PI 3-kinase activity removed from supernatant of column in lane 2 by fresh phosphorylated Y751 column. Lane 4, PI 3-kinase activity remaining associated with the column from lane 2 following removal of the bound material using 0.1% SDS at 80° C. Lane 5, PI 3-kinase activity bound to recycled phosphorylated Y751 column as used in lane 2 following addition of a fresh aliquot of bovine brain PI 3-kinase in binding buffer. Lane 6, Equivalent amount of peak 1 soluble bovine brain PI 3-kinase activity as applied to columns in lane 2 or lane 5.

Figure 4C:
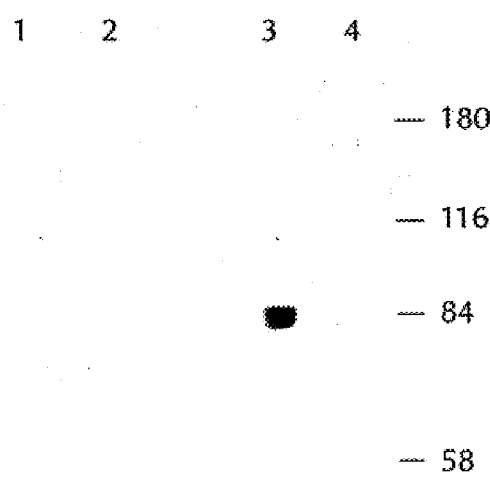
Figure 4D:
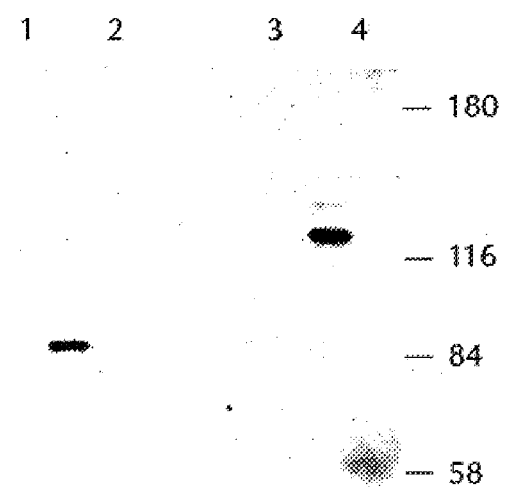

FIG. 4. Identify of p85 species in peak 1 and 2 of bovine brain PI 3-kinase preparation.

Protein samples were separated on 7.5% SDS-PAGE gels and transferred to nitrocellulose. The blots were then probed with antisera raised against the COOH-terminal peptide sequences of p85α or p85β.

Panel A. Western blot probed with anti-p85α COOH—terminal antisera.

Lane 1, peak 1 bovine brain PI 3-kinase; lane 2, peak 2 bovine brain PI 3-kinase; lane 3, Cos-1 cell lysate from pMT2 vector alone transfected cells; lane 4, Cos-1 cell lysate from pMT2p85α transfected cells; lane 5, Cos-1 cell lysate from pMT2p85β transfected cells; lane 6 Sf9 cell lysate containing p85α; lane 7, Sf9 cell lysate containing p85β Panel B. Western blot probed with anti-p85β COOH-terminal antisera.

Lanes are as described for panel A.

Panel C. Competition of peptides with antibodies in Western blots. Samples in lanes 1 and 2 were probed with p85a specific antiserum while samples in lanes 3 and 4 were probed with the p85β specific antiserum. Lanes 1 and 2. Sf9 cell lysate containing baculovirus expressed p85α. Lanes 3 and 4, Sf9 cell lysate containing baculovirus expressed p85β. In the odd numbered lanes the nitrocellulose was probed with specific antiserum alone. In the even numbered lanes the antiserum was competed with 100 μg/ml of p85α (lane 2) and p85β (lane 4) specific C-terminal peptides respectively.

Panel D. Anti p85α western blot of bound and soluble PI 3-kinase material after chromatography using the Y751 phosphopeptide column.

Peak 1 (P1) and peak 2 (P2) of bovine brain PI 3-kinase were immobilised on the Y751 phosphopeptide column. Material which did not bind was collected and then the resin was washed extensively. Bound proteins were eluted from the column with SDS-PAGE sample buffer. Bound and unbound proteins were separated by SDS-PAGE on a 7.5% gel and then transferred to nitrocellulose. The filter was then probed with anti-p85a COOH-terminal antisera and visualised with $^{125}$I Protein A-Sepharose. Lane 1, P1 bound material; Lane 2, peak 1 material which did not bind to column; Lane 3, peak 2 bound material; Lane 4, peak 2 material which did not bind to column.

Figure 5A:
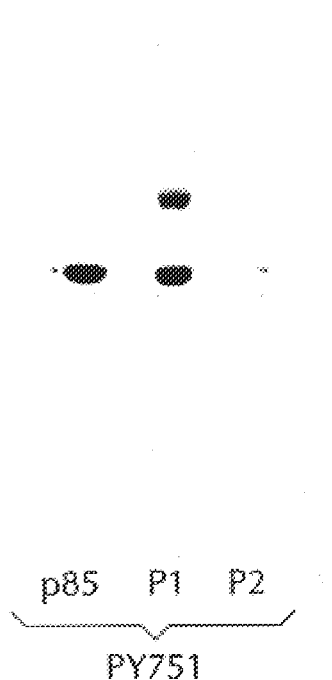
Figure 5B:
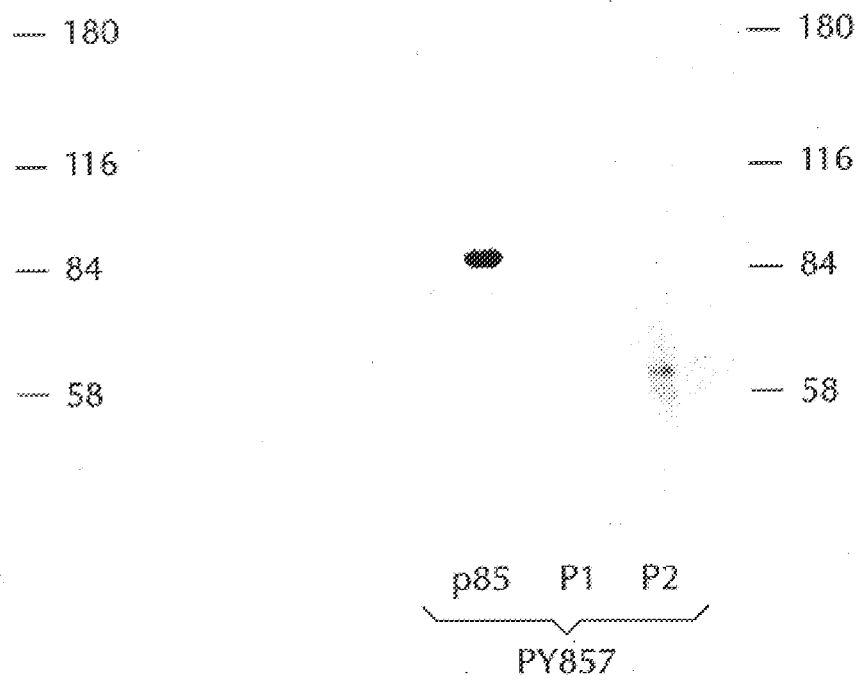

FIG. 5. Specificity of binding of PI 3-kinase complex to Y751 peptide column:-comparison with Y857 phosphopeptides.

Sf9 cell lysates containing p85α proteins or one microgram of partially purified bovine brain PI 3-kinase (P1 and P2 MonoQ) was allowed to bind to the columns for 4 h at 4° C. as described. The columns were then washed repeatedly with binding buffer, bound proteins were eluted with SDS-containing buffers and then analysed by electrophoresis on 7.5% SDS-PAGE gels. Bound proteins were visualised by silver staining. Panel A. Proteins bound to Y751 phosphopeptide column. Panel B. Proteins bound to Y857 phosphopeptide column. The migration position of molecular weight markers are indicated.

FIG. 6. Binding of recombinant baculovirus expressed p85 proteins to a panel of phosphopeptide columns.

P85 proteins in SF9 cell lysates were tested for their ability to bind to the various peptide column. After extensive washing, bound proteins were eluted from the columns, separated on 7.5% SDS-PAGE gels and the visualised by staining with Coomassie Blue. Panel A. Bound p85α. Panel B. Bound p85β. CON, 17 amino acid non-phosphorylated Y751 column; Y751, 17 amino acid phosphopeptide from the kinase insert region of the PDGF β-receptor; Y751.S, 11 amino acid version of Y751 phosphopeptide; Y857, 17 amino acid phosphopeptide derived from the sequence around the second major tyrosine phosphorylation site in the PDGF β-receptor; pGAT, poly Glu:Ala:Tyr phosphopeptide; Y416 and Y527, 13 and 16 amino acid phosphopeptides derived respectively from the two major tyrosine phosphorylation sites of pp60$^{c\text{-}src}$.

Figure 7A:
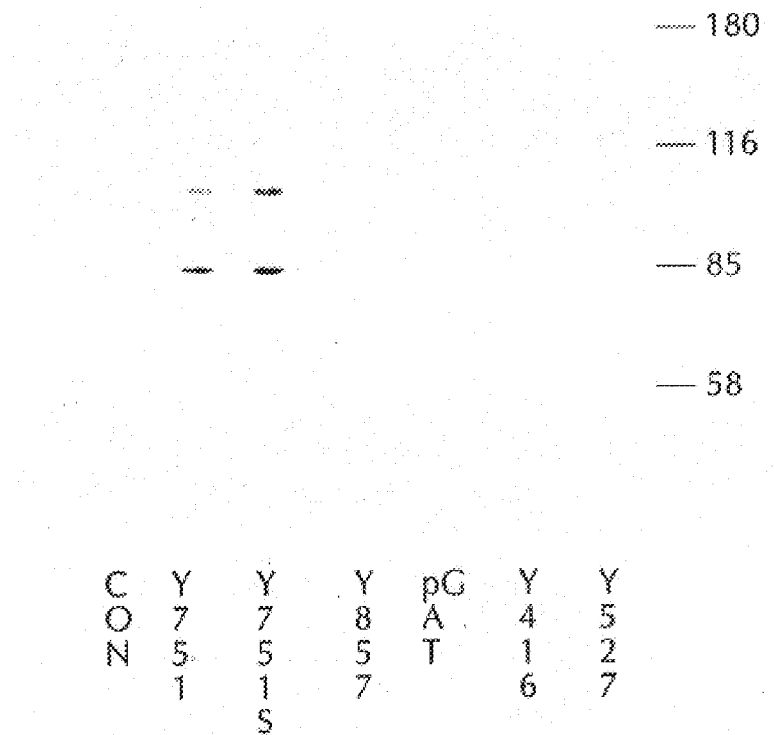
Figure 7B:
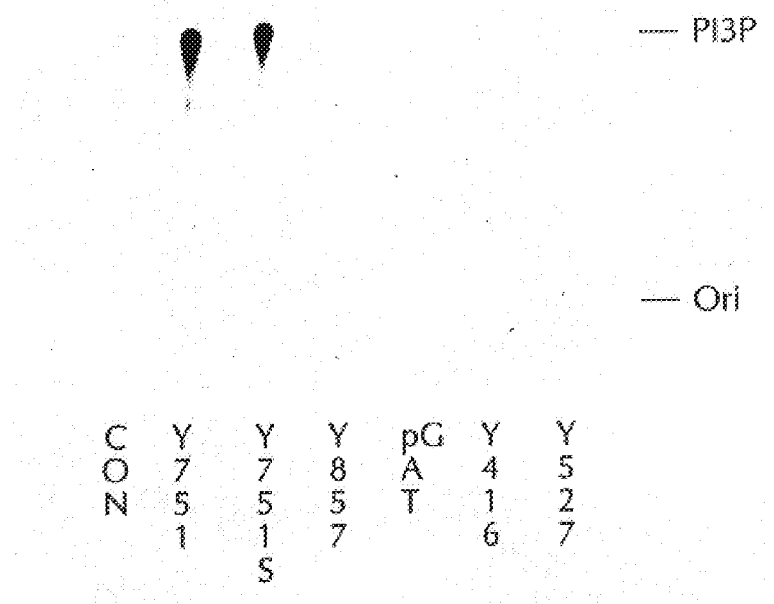

FIG. 7. The p85/100 complex and PI 3-kinase activity show specificity in the range of phosphopeptides to which they will bind.

One microgram of partially purified bovine brain PI 3-kinase (P1 MonoQ) was allowed to bind to peptide affinity columns for 4 h at 4° C. as described. The columns were then washed repeatedly with binding buffer. Bound proteins were then either eluted with SDS-containing buffers and then analysed by electrophoresis on 7.5% SDS-PAGE gels or assayed for PI 3-kinase activity bound to the column.

Panel A. Bound proteins were visualised by silver staining. The migration of molecular weight markers is indicated.

Panel B. PI 3-kinase activity bound to various phosphopeptide columns. The $^{32}$P-labelled lipid products were separated by TLC and the visualised by autoradiography. PI3P indicates the migration position of a P13P standard. Ori indicates the origin of the TLC plate.

Figures 8A, 8B:
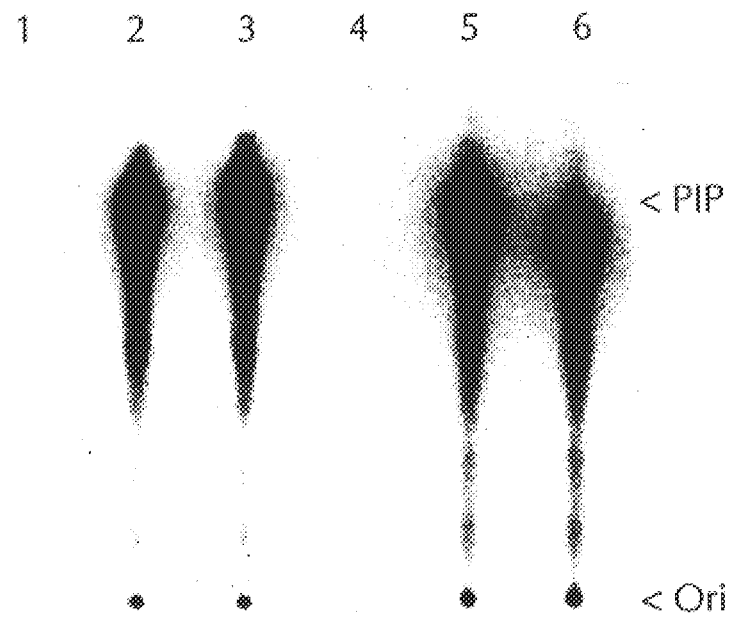

FIG. 8. Binding of PI 3-kinase activity of phosphopeptides containing the YXXM motif.

Panel A. One microgram of partially purified peak 1 bovine brain PI 3-kinase was bound to 10 μl of the indicated peptide columns. Following extensive washing the columns were assayed for bound PI 3-kinase activity. Lane 1, PI 3-kinase activity bound to non-phosphorylated Y751 column; Lane 2, PI 3-kinase activity bound to phosphorylated Y751 column; Lane 3, PI 3-kinase activity bound to phosphorylated Y751.S column; Lane 4 PI 3-kinase activity bound to phosphorylated Y857 column; Lane 5, PI 3-kinase activity bound to phosphorylated Y740 column; Lane 6, PI 3-kinase activity bound to phosphorylated Met Y1313 column. PIP indicates the migration position of a P14P standard. Ori indicates the origin of the TLC plate.

Panel B. Comparison of identified PI 3-kinase binding sites in the peptides tested. The proposed consensus sequence for binding is also shown for comparison (Cantley et al., 1991).

FIGS. 9 to 15 are concerned with Example 1, sections C and D, and FIGS. 16 to 25 relate to Example 2.

Figure 9I:
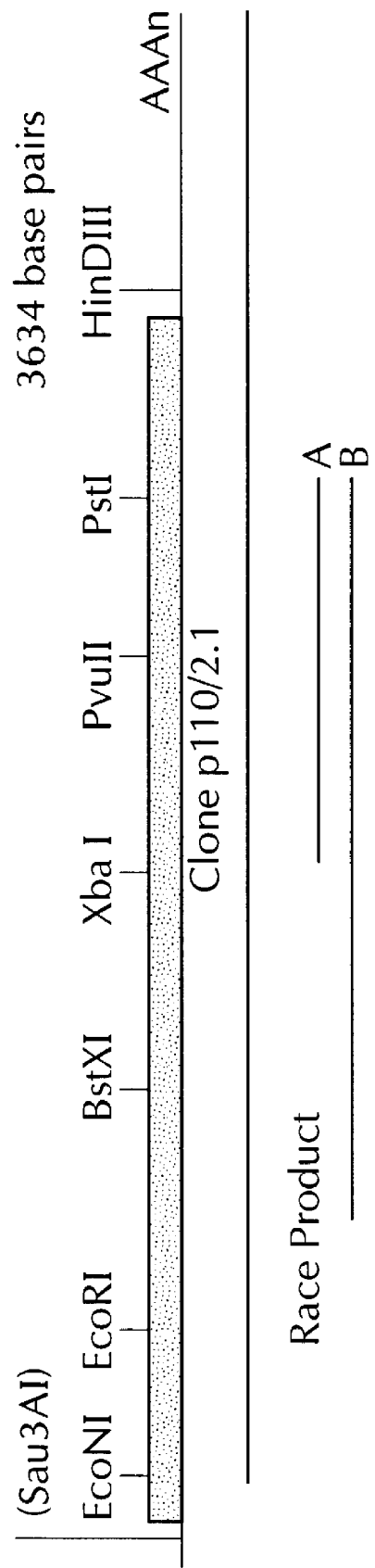

FIG. 9. Nucleotide Sequence and Deduced Amino Acid Sequence of p110.

(Top Panel) The nucleotide sequence of the coding region and the deduced amino acid sequence in one letter code are shown. Peptide sequences (lettered from A–N) obtained by protein sequencing are highlighted.

(Lower Panel) Schematic representation of the p110 cDNA. The bold line indicates coding sequence. (p2.1): extent of clone p2.1, (Race Product): region amplified by RACE PCR, (a): probe used in Southern blot analysis, (b): probe used in northern blot analysis, (S): Sau3AI site changed to BamHI site for expression in Sf9 cells.

Figure 10A:
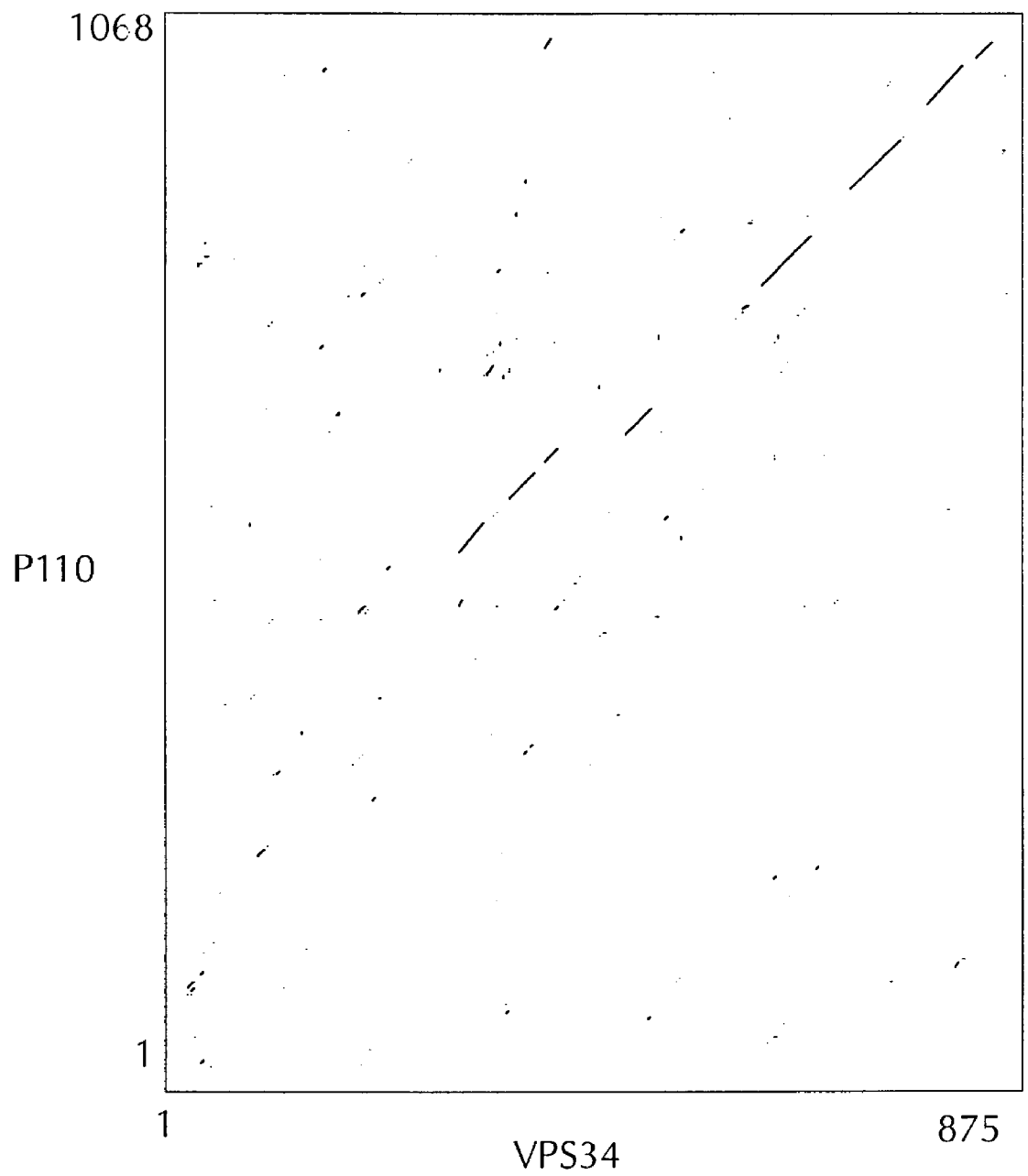
Figure 11A:
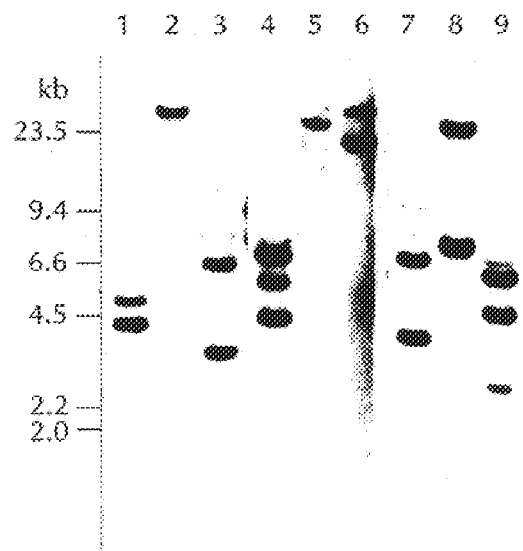
Figure 11B:
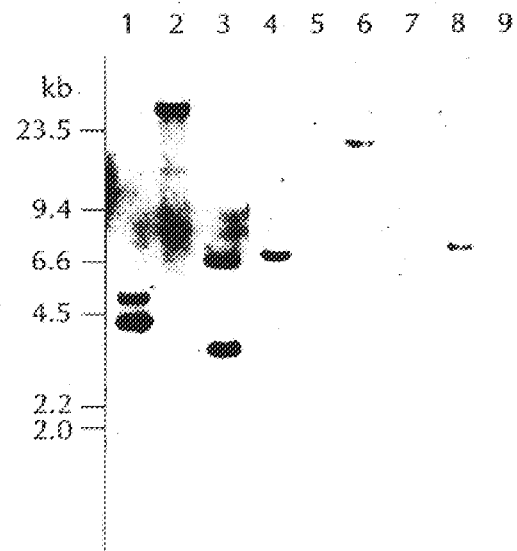

FIG. 10. Comparison of p110 and Vps34p Protein Sequences (A) Dot plot comparison of Vps34p (875 amino acids: horizontal axis) and p110 (1068 amino acids: vertical axis) using the Compare program (UWGCG package; Devereux et al., 1984).

(B) The optimal alignment of p110 (upper sequence) and Vps34p (lower sequence) over the region of homology, using the Gap program (UWGCG package: Devereux et al., 1984). Identical residues are indicated by (I), conserved residues are indicated by (:). Residues proposed to be involved in ATP binding are marked with (*).

FIG. 11. Genomic Southern Analysis of p110

High molecular weight DNAs (3 μg) of bovine (lanes 1, 2, 3), human (lanes 4, 5, 6) and rat (lanes 7, 8, 9) origin were digested with EcoRI (lanes 1, 4, 7), BamHI (lanes 2, 5, 8) of Hindlll (lanes 3, 6, 9), fractionated through a 0.5% agarose gel and transferred to a nitrocellulose membrane as described in Example 1. The filter was probed with a $^{32}$P-labelled XbaI-PstI fragment (probe a in FIG. 9, lower panel). The filter was washed in 0.5×SSC, 0.1% SDS at 50° C. and exposed overnight (Panel A). The filter was then washed in 0.1×SSC, 0.1% SDS at 68° C. and exposed for seven days (Panel B). The marker track shows the positions of lambda Hindlll markers.

FIG. 12. Analysis of Tissue Distribution of p110 Message (A) Northern Blot Analysis of p110 5 μg of poly(A)$^+$RNA isolated from total bovine brain (lane 1) or the SGBAF-1 cell line (lane 2) were fractionated on a 0.9% agarose gel and immobilised on membranes as described in Example 1. The filter was probed with a $^{32}$P labelled antisense RNA probe (probe b in FIG. 9, lower panel). After washing in 0.1×SSC, 0.1% SDS at 60° C., the filter was treated with 1 μg ml$^{-1}$ RNAase A and autoradiographed overnight.

(B) PCR Analysis to Detect p110 Transcripts Poly(A)$^+$ RNA was isolated from various sources and PCR performed as described in Example 1. Bands of 218 bp and 212 bp indicate the specific amplification of human and bovine transcripts, respectively. Lane 1; Human T-cell blasts, lane 2; Human peripheral blood acute lymphocytic leukaemia cells, lane 3; A431 cells (Human), lane 4; COS-1 cells (Simian), lane 5; bovine brain, lane 6; SGBAF-1 cells (Bovine), lane 7; ZNR cells (Porcine).

(C) PCR Analysis to Detect p85α Transcripts Poly (A)$^+$ RNA was isolated from various sources and PCR performed. Specific amplification of p85α message gives a bind of 190 bp. Lanes are the same as indicated for (B).

FIG. 13. Expression of p85α and p110 in Sf9 Cells Using Baculovirus Vectors (A) Sf9 cells were infected with a wild type baculovirus (lanes 1 and 2) or with baculoviruses expressing p85α (lane 3), p110 (lane 4) or p85α and p110 (lanes 5 and 6). Immunoprecipitates were prepared with either anti-p85α (lanes 1, 3, and 5) or anti-p110 antisera (lanes 2, 4 and 6), samples fractionated on a 7.5% SDS-PAGE gel and visualised by staining with Coomassie blue.

(B) PI3-kinase assays were performed on Immmunoprecipitates of p85α and p110 expressed in Sf9 cells. lanes 1–6 the same as Panel (A); lane 7: pI3-kinase activity from 1 μl of the partially purified bovine brain PI3-kinase preparation.

Figure 14A:
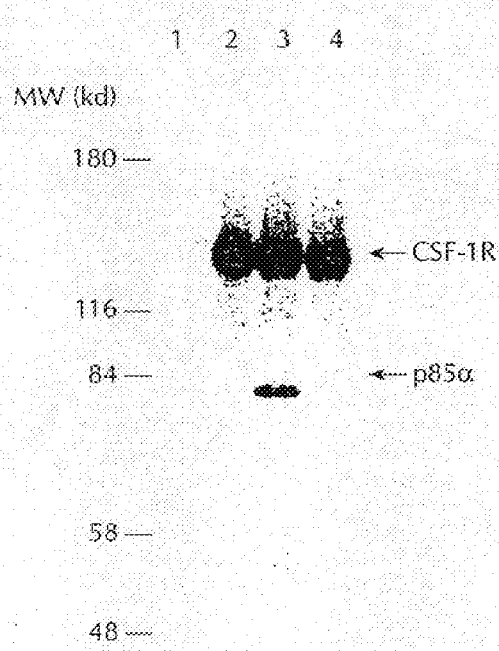
Figure 14B:
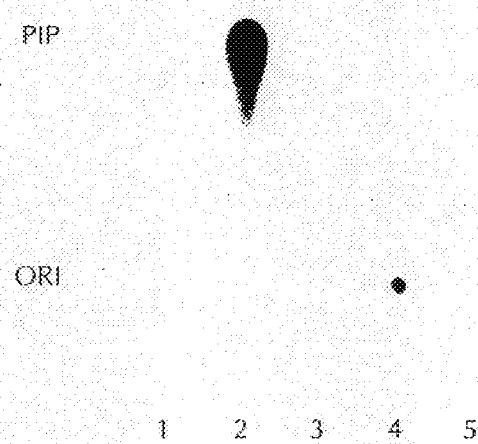

FIG. 14. In Vitro Association of PI3-Kinase Activity with the CSF-1 Receptor

An in vitro PI3-kinase assay was performed on anti-CSF-1 receptor immunocomplexes prepared from Sf9 cells infected with a baculovirus expressing the CSF-1 receptor and treated as follows; lane 1: anti-CSF-1 receptor immunoprecipitates, untreated; lane 2; anti-CSF receptor immunoprecipitate, pre-treated with ATP and incubated with a p85α/p110 containing Sf9 cell lysate; lane 3: anti-CSF-1 receptor immunoprecipitate, treated in the absence of ATP and incubated with a p85α/p110 containing Sf9 cell lysate; lane 4: anti-CSF-1 receptor immunoprecipitate, pre-treated with ATP and incubated with a p85α containing Sf9 cell lysate; lane 5; anti-CSF-1 receptor immunoprecipitate, pre-treated with ATP and incubated with a p110 containing Sf9 cell lysate.

FIG. 15. Expression of p85α and p110 in COS-1 Cells

COS-1 cells were transfected with 5 μg of the respective DNAs and harvested 48 h later. Transfected cells were labelled with 100 μCi ml $^{-1}$ of $^{35}$S-methionine for the last 4 h of this period. Immunoprecipitations were performed with either an p85α polyclonal antiserum or a p110 C-terminal peptide antiserum. After washing, the pellet was divided in two and half was then analysed on a 10% SDS-PAGE gel while the other half was subjected to P13-kinase assay.

(A) $^{35}$S-labelled proteins immunoprecipitated with anti-p85α antiserum.

(B) PI3-kinase activity immunoprecipitated with anti-p85α antiserum.

(C) $^{35}$S-labelled proteins immunoprecipitated with 110 C-terminal peptide antiserum.

(D) p13-kinase activity immunoprecipitated with 110 C-terminal peptide antiserum.

Lanes contain results from COS-1 cells transfected with the following DNAs; lane 1: vector DNA, lane 2: pMT2-p85α, lane 3: pSG5-p110, lane 4: pMT2-p85α and pSG5-110, lane 5 in panels B and D show the PI3-kinase activity immunoprecipitated with the two antisera from 1 μl of the partially purified bovine brain p13-kinase preparation. The exposure times for panels A and C, and B and D are identical.

FIG. 16. CDNA for human p110

The figure shows the sequence of human p110 CDNA, together with the corresponding amino acid sequence.

FIG. 17. A comparison of the human p110 sequence and bovine p110 sequence at the DNA level.

FIG. 18. A comparison of the human p110 sequence and bovine p110 sequence at the protein level.

FIG. 19. The protein sequence of human p110.

FIG. 20. The sequence of a cDNA related to p110, PITR-c.

FIG. 21. The sequence of a cDNA related to p110, PITR-f.

FIG. 22. The alignment of human p110, PITR-c, PITR-f and the yeast PI3-kinase VPS34.

Figure 23A:
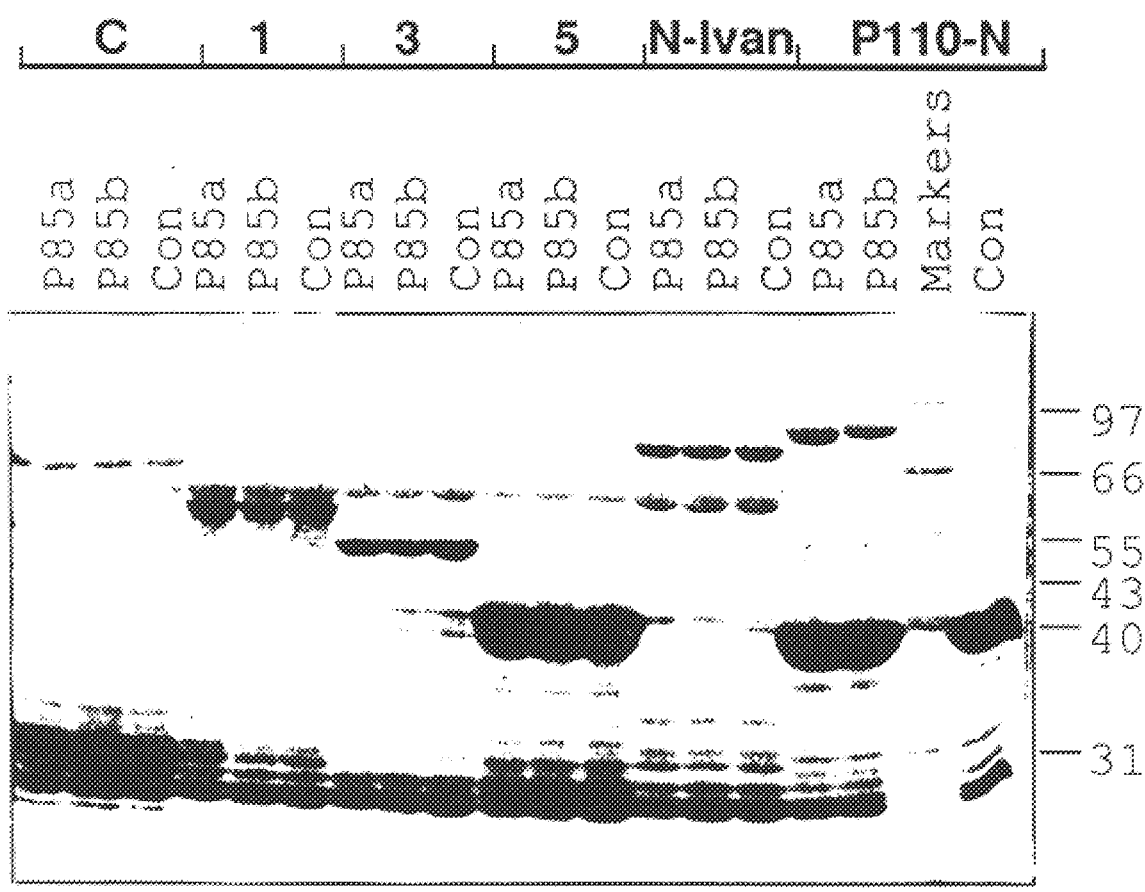

FIG. 23A. SDS PAGE analysis of proteins able to bind to various domains of human p110.

Figure 23B:
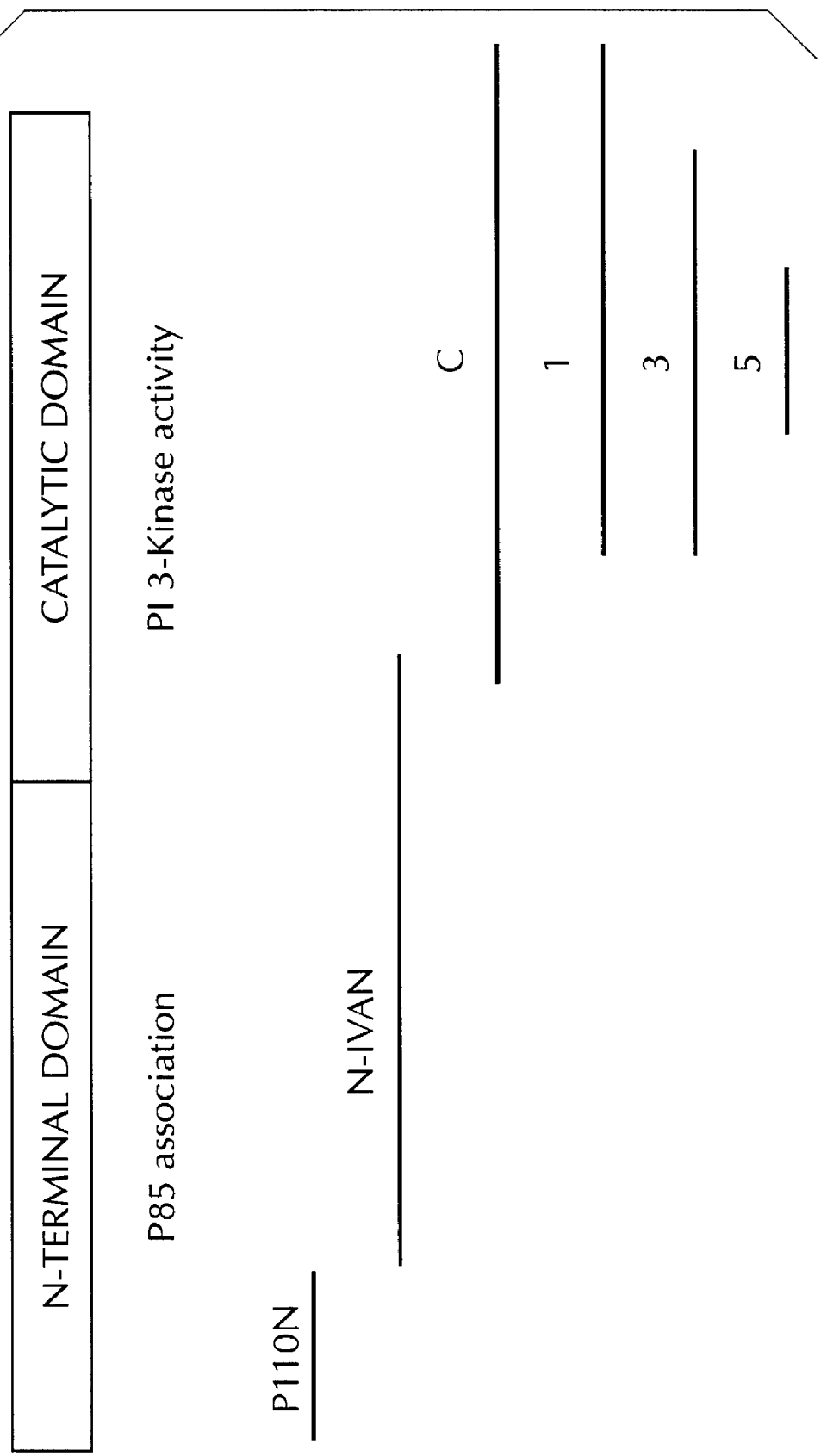

FIG. 23B. Schematic representation of the domains of p110 analysed for their ability to bind p85.

Figure 24:
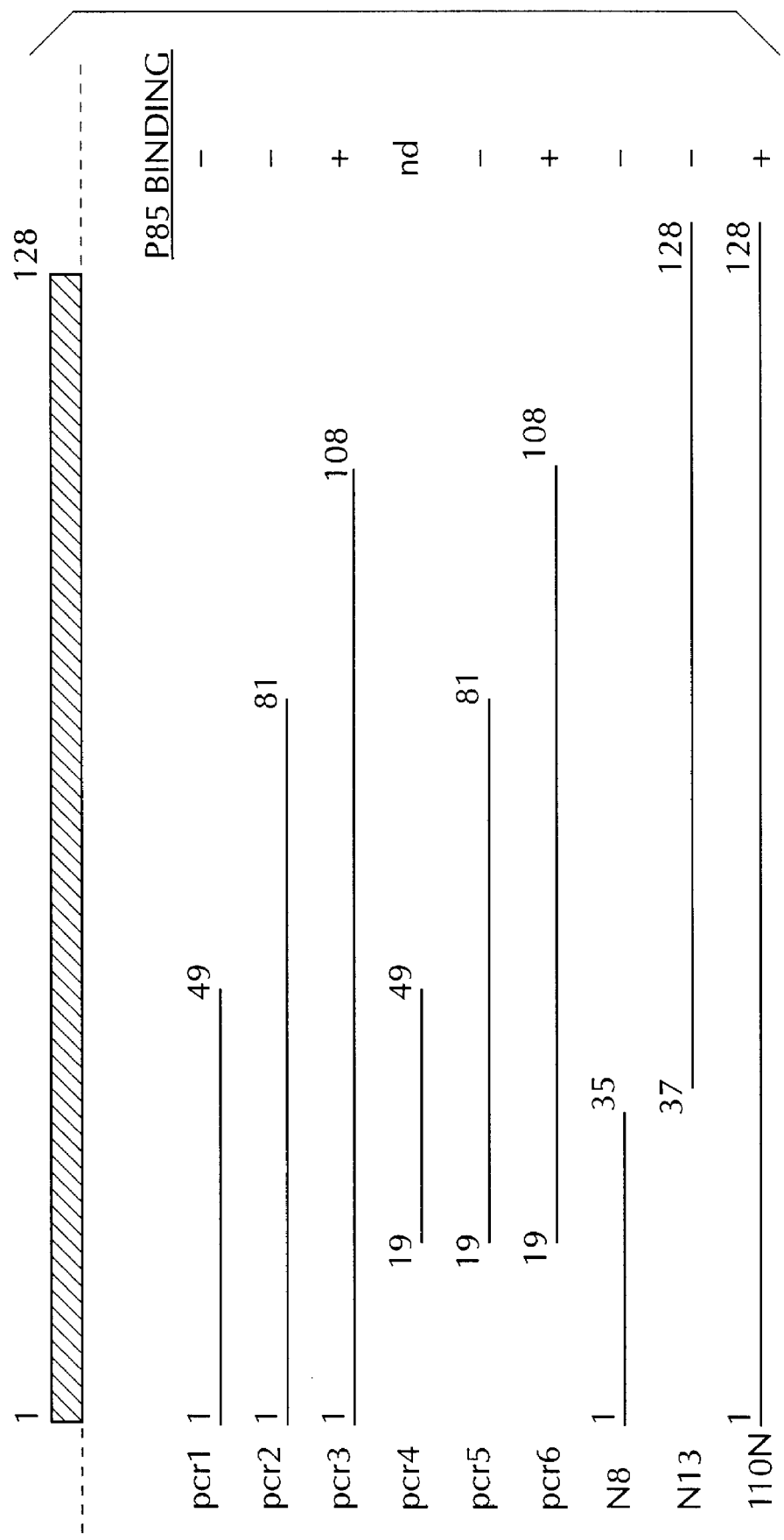

FIG. 24. Various deletion mutants and PCR fragments of p110 fragment p110-N.

Figure 25A:
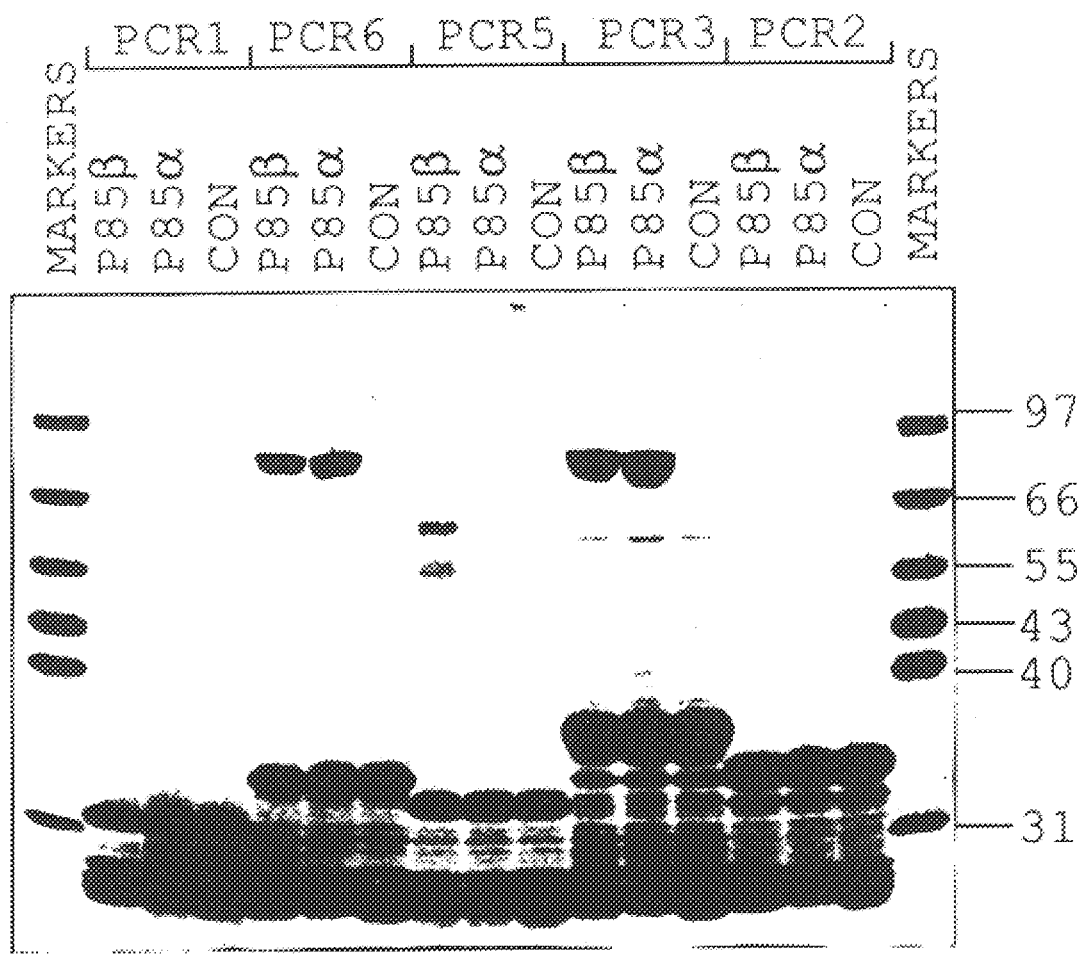
Figure 25B:
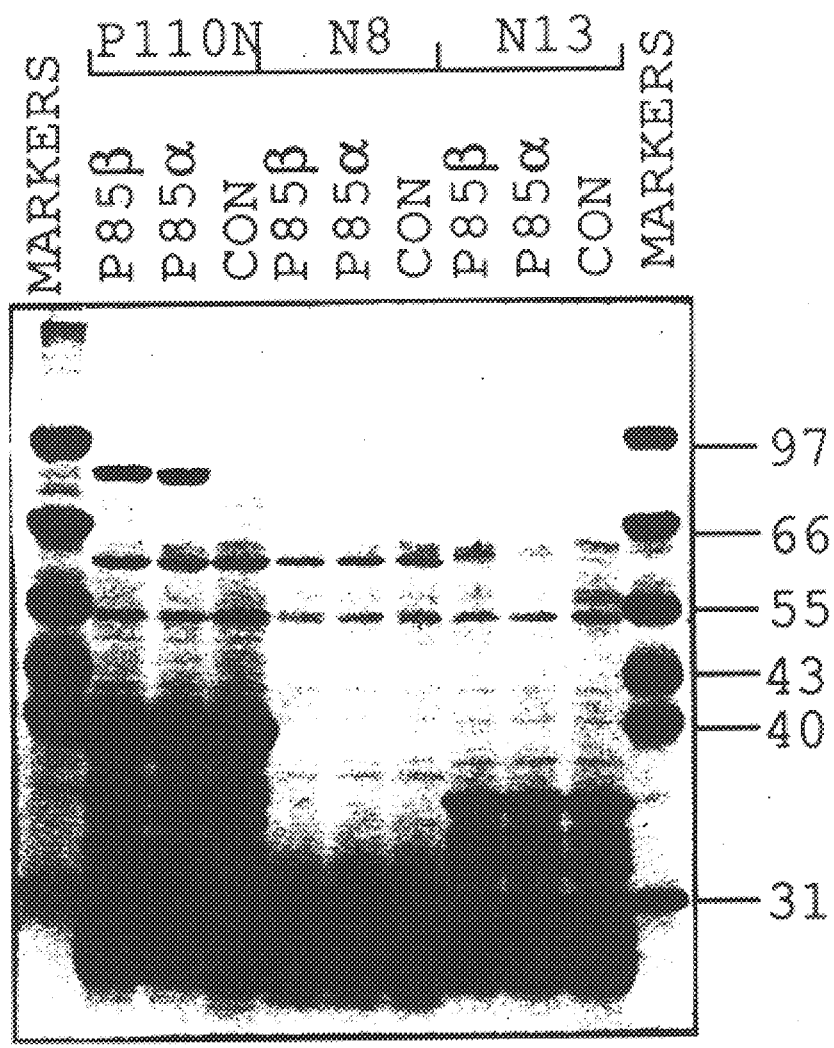

FIG. 25. The ability of the various deletion mutants and PCR fragments of p110-N to bind the p85 subunits.

EXAMPLE 1

PROTEIN PURIFICATION

A. Methods and Materials
Cells

A431 cells were maintained in Dulbecco's modified Eagle's medium containing 10% foetal calf serum. Maintenance of insect cell culture and infection of Spodoptera frugiperda (Sf9) cells were carried out as described in Summers and Smith (1987).
Preparation of A431 Membranes This preparation was modified from that described by Thom et al (1977). Harvesting solution (0.05 M boric acid (pH 7.2), 0.15 M NaCl), extraction solution (0.02 M boric acid (pH 10.2), 0.2 mM EDTA) and borate solution 0.5 M Boric acid (pH 10.2) were all prepared fresh. Cells were washed once with ice-cold harvesting solution and then scraped into fresh harvesting solution. Cells were pelleted by low speed centrifugation at 200 g, and then resuspended by pipetting in 2 pellet volumes of harvesting solution. This was added slowly, with stirring, to 100 pellet volumes of extraction solution. After 10 min, 8 pellet volumes of borate solution was added and stirring continued for a further 5 min. This solution was filtered through nylon gauze (Av. mesh size 900 μm), and spun at 500 g for 10 min at 2° C. to pellet any nuclei/whole cells. Finally, the supernatant was centrifuged at 12,000 g in a ultracentrifuge SW28 rotor at 4° C. for 30 min. The membrane pellet was resuspended in a minimum volume of 50 mM Hepes (pH 7.5) and stored at −70° C.

Synthesis of Peptides

Peptides described in Table 2 below were synthesized on an Applied Biosystems 430A peptide synthesizer using FMOC chemistry and an appropriate amino acid addition program according to ABI's recommendations. Peptides were then purified by preparative reverse-phase HPLC. Composition of the peptides was checked by analytical HPLC, amino acid analysis and protein sequencing on an 477A automated pulse-liquid sequencer.

TABLE 2

| Peptide | Sequence |
| --- | --- |
| Y740 | G E S D G G Y M D M S K (SEQ ID NO:1) |
| Y751 | D M S K D E S V D Y V P M L D M K (SEQ ID NO:2) |
| Y751.S | C D E S V D Y V P M L (SEQ ID NO:3) |
| Y857 | A R D I M R D S N Y I S K G S T F (SEQ ID NO:4) |
| Y1313 | E F C P D P L Y E V M L K (SEQ ID NO:5) |
| Y527 | R R F T S T E P Q Y Q P G E N L (SEQ ID NO:6) |
| Y416[a] | R R L I E D N E Y T A R G (SEQ ID NO:7) |

[a]This peptide was purchased from Sigma Chemical Co Ltd rather than synthesized.

Phosphorylation of Peptides

Peptides were lyophilised to dryness to remove any contaminating chemicals remaining from synthesis/purification and then dissolved in HPLC grade water at a concentration of ~4 mg/ml.

For small scale phosphorylation: 20 μg of peptide, 10 μl 5x kinase buffer (250 mM Hepes (pH 7.4), 750 mM NaCl, 0.1% Triton X-100, 10 nM MnCl$_2$, 60 mM MgCl$_2$, 50% glycerol, 500 mM sodium orthovanadate), 5 μl A431 membrane preparation and ATP/[γ-$^{32}$P]ATP (relative amounts depends on aim of phosphorylation). Water was added to adjust the volume to 50 μl.

For preparative phosphorylation, 2–3 mg of peptide was dissolved in 1.5 ml of water and added to 450 μl 5x kinase buffer. The pH was adjusted to 7.0. 250 μl of 0.1 M ATP and 500 μl of A431 plasma membranes (~2 mg/ml) was added and then the reaction was allowed to proceed for 18 h at room temperature with continual mixing.

Isolation of Phosphorylated Peptides by Reverse Phase HPLC

One millilitre of buffer A (Buffer A: 0.08% trifluoracetic acid, 1% acetonitrile in water; Buffer B: 0.08% trifluoracetic acid, 90% acetonitrile) was added to the kinase reaction and mixed. This solution was then spun for 20 min at 10,000 g to pellet the membranes. The supernatant containing the phosphopeptide was then loaded onto a Sep-Pak column (C$_{18}$) equilibrated with buffer A. The column was washed with 20 ml buffer A to elute ATP and then the peptide was eluted with 3×1 ml of 40% buffer B. The OD of the fractions was monitored at 268 nm and fractions containing peptide were pooled and then lyophilised to dryness (note that the phosphorylated Y751 peptide has essentially no absorption at 280 nm). The phosphopeptide was then separated from non-phosphorylated peptide using a 1090 HPLC system. For preparative separation a C$_{18}$ column (Aquapore OD-300, 250×7 mm) equilibrated with 100% buffer A (214 nm (sen. 50 mV)/280 nm (sen. 200 mV) was used with a 2 ml/min flow rate. The peptide was dissolved in 200 μl HPLC grate water and then loaded via a 500 μl loop. The column was then washed for 10 min with 100% buffer A before eluting the peptide and phosphopeptide with a 30 min linear gradient 0 to 45% buffer B followed by 5 min linear gradient to 100% buffer B. Peak fractions were collected manually. The pool fractions were diluted with water, lyophilised and then stored at −20° C.

Phosphoamino Acid Analysis of Phosphorylated Peptides

Peptides phosphorylated in the presence of [γ-$^{32}$P]ATP using either purified EGF receptor or A431 cell membranes were purified by C$_{18}$ Sep-Pak column and HPLC as described above. This material was then hydrolysed at 110° C. for 1 h in 1 ml of 6 M HCl. One millilitre of HPLC grade water was added and the sample was centrifuged at 10,000 g for 10 min to removed debris. The remaining supernatant was frozen and lyophilised to dryness. The pellet was resuspended in 2 ml of water, frozen and then lyophilised once more. This material was analysed by two dimensional thin-layer electrophoresis (essentially as described by Cooper et al, 1983).

Coupling of Peptides to Actigel Resin

Peptides were coupled to the matrix essentially as described by the manufacturers. Briefly, 500 μl (packed volume) of Actigel-ALD Superflow resin (Sterogene, Calif., USA) was washed five times with 100 mM phosphate buffer (pH 7.8) (coupling buffer). Phosphorylated or non-phosphorylated peptide (1 mg) was dissolved in 200 μl of coupling buffer and added to the resin. NaCNBH$_3$ (coupling solution) was added to a final concentration of 100 mM and this was then mixed at 4° C. for 6 h. The resin was washed with 10 column volumes of 500 mM NaCl and then incubated with 100 mM Tris-HCl (pH 8.0) for 1 h in the presence of coupling solution to block any unreacted sites on the resin. The resin was washed with 500 mM NaCl and finally with coupling buffer plus 500 μM vanadate and 0.02% NaN$_3$ and then stored at 4° C. Phosphopeptides bound to the Actigel matrix were stable for several months under these conditions.

Binding of Proteins to the Phosphopeptide Columns

Proteins were diluted in binding buffer (50 mM phosphate buffer (pH 7.2), 150 mM NaCl, 0.02% Triton X-100, 2 mM EDTA and 200 μM sodium orthovanadate), mixed with the appropriate peptide affinity resin and then allowed to bind for 2 h at 4° C. with rotation. The column material was washed repeatedly (>6x) with 50 column volumes of the same buffer and then with various elution buffers containing NaCl, urea or detergents. Bound proteins were either assayed for PI3-kinase activity or were removed from the column by boiling in SDS-PAGE sample buffer and then analysed by SDS-PAGE.

PI3-kinase Assay

PI3-kinase assays were carried out essentially as described in Whitman et al, (1987) in 50 μl containing 50 mM Tris-HCl (pH 7.5), 50 mM NaCl, 1 mM DTT, 0.5 mM EDTA, 5 mM MgCl$_2$, 100 μM ATP (plus 0.5 μCi [γ-$^{32}$P] ATP/assay), 1 mM PI plus soluble or column immobilised bovine brain PI3-kinase. Incubation was for 5 min at room temperature. The reaction was terminated by the addition of 100 μl of 0.1 N HCl and 200 μl chloroform:methanol (1:1). The mixture was vortexed and then centrifuged to separate the phases. The upper phase was discarded and the lower organic phase washed with 80 μl of methanol: 1 N HCl (1:1).

After centrifugation the upper phase was again discarded and the lower phase evaporated to dryness. Reaction products were spotted on thin layer Silica gel 60 plates (pretreated with 1% oxalic acid, 1 mM EDTA in water-:methanol (6:4)) and developed in chloroform:methanol:4 N ammonia (9:7:4).

Preparation of C-terminal Specific Antisera for p85α and p85β

C-terminal peptide antisera were prepared against the bovine C-terminal sequences determined by cDNA cloning (Otsu et al, 1991). The peptides TLAYPVYAQQRR (SEQ ID NO:8) for p85α and TLAHPVRAPGPGPPAAR (SEQ ID NO:9) for p85α were synthesized by FMOC chemistry and purified by HPLC. The peptides were coupled using gluteraldehyde to KLH and then injected into the lymph nodes of rabbits using methods described in Kypta et al, (1988). Positive antisera as determined by enzyme-linked immunoassay were affinity purified on specific peptide-Actigel affinity columns.

B. Procedure and Results of Purification

Preparation of Y751 Phosphopeptide Column

A 17 amino acid peptide which contains Y751 of the human PDGF-β receptor was chosen for synthesis in an attempt to inlcude all necessary sequence determinants following a survey of the known binding sites for the PI3-kinase (see Table 2 above; reviewed in Cantley et al, 1991). In addition to the peptide context of Y751 of the PDGF β-receptor, the sequences around Y315 of polyoma middle T (Talmage et al, 1989) and Y721 of the human CSF-1 receptor (Shurtleff et al, 1990) were also considered. Using the phosphorylation protocol described above, greater than 50% phosphorylation of the Y751 peptide was achieved using either purified human EGF receptor or A431 membranes as a source of protein-tyrosine kinase. The phosphorylated Y751 peptide could be clearly identified during reverse phase HPLC analysis, where it eluted approximately one minute earlier than the nonphosphorylated peptide, since it produced a strong 214 nm absorbance, but little or no 280 nm signal (FIG. 1, panel A). Analysis of the absorption properties showed that phosphorylation of the Y751 peptide led to a shift in the absorption maximum from 280 to 267 nm (FIG. 1, panel B). For large scale phosphorylations A431 membranes were the preferred source of protein-tyrosine kinase activity since they could be more easily generated. However, as the Y751 peptide contains two serines, as well as a single tyrosine residue, it was thought important to demonstrate that peptide was phosphorylated exclusively at the tyrosine residue. This was established by two separate methodologies; analysis of HPLC purified phosphopeptide by phosphoamino acid analysis or by protein microsequencing. Phosphoamino acid analysis of the Y751 peptide, phosphorylated by either purified EGF receptor or A431 membranes, demonstrated that phosphorylation of the Y751 peptide was occuring exclusively at the tyrosine residue (FIG. 1, panel C). Sequence analysis of the phosphorylated and non-phosphorylated peptides also confirmed that both these peptides were 17 amino acids in length and that their sequences were identical except at cycle 10 where as expected no phenylthiohydantoin-Tyr derivative was observed for the phosphorylated peptide due to its modification.

Extended Purification of Bovine Brain PI3-kinase Using a Y751 Phosphopeptide Affinity Column A 650-fold purification of PI3-kinase from bovine brain has recently been described (Morgan et al, 1990), and this same method was used except that the gradient for the second Mono Q column was extended to give two distinct peaks containing PI3-kinase activity (FIG. 2, panel A). Both of these peaks (referred to hereafter as peak 1 (P1) and peak 2 (P2)) contained no PI kinase activity other than PI3-kinase activity as determined by HPLC analysis of deacylated product lipids (data not shown). However, both of these fractions still contained greater than 20 peptides detectable after SDS-PAGE gel analysis by silver staining (see FIG. 2, panel A). The precise subunit composition of the active PI3-kinase complex was still a point of some contention, so an attempt was made to address this question by affinity purifying the PI3-kinase activity from these two Mono Q pools. The bovine brain PI3-kinase preparation was diluted 10-fold in binding buffer and allowed to bind batchwise to the Y751 phosphopeptide affinity resin for 4 h at 4° C. After washing the column extensively with binding buffer, those proteins which remained bound were eluted with SDS-containing buffers and examined by SDS-PAGE. Two major polypeptide species of approximate molecular weights 85 and 110 kD, which bound specifically to the phosphopeptide column, but not to an identical column prepared with unphosphorylated Y751 peptide, were identified in both Mono Q peaks and were observed to be quantitatively depleted from the bovine brain PI3-kinase preparation (FIG. 2, panel B). Assaying the bound material, the presence of these two proteins appeared to be sufficient to generate full PI3-kinase activity (FIG. 3, lane 2). With fresh preparations of bovine brain PI3-kinase this column routinely removed >90% of the PI3-kinase activity present in Mono Q peaks 1 or peak 2 (c.f., FIG. 3, lanes 2 and 3) following a single incubation. Neither the 85 and 110 kD proteins, nor PI3-kinase activity bound to a column with an equivalent concentration of non-phosphorylated Y751 peptide (FIG. 3, lane 1) or to a column prepared with phosphotyramine, a phosphotyrosine analogue (data not shown). It should also be noted that binding of the PI3-kinase complex to the phosphopeptide column did not result in any apparent increase in the total enzyme activity present (FIG. 3, c.f., lanes 2 and 6). In fact a slight decrease in activity was often observed, but this was judged to be due to the unstable nature of the highly purified enzyme which was found to be inhibited by traces of metal ions and reversibly inhibited by oxidation. It is estimated that this affinity purification step results in a 7–8,000-fold purification of PI3-kinase from bovine brain relative to the DEAE load (the overall purification achieved from tissue is in fact much greater).

Elution of p85, p110 and PI3-kinase Activity from the Phosphopeptide Column

Elution of the above PI3-kinase complex from the phosphopeptide column proved to be difficult to achieve due to the high affinity of the interaction. Kazlauskas and Cooper (1990) have previously noted that the binding of cellular p85 proteins to phosphorylated PDGF-receptor was stable to treatment with solutions containing ionic detergents, 2 M NaCl, 1 M urea or 0.2% SDS. The p85 subunits and PI3-kinase complex were also found to bind tightly to the Y751 phosphopeptide matrix, and were likewise not eluted under any of the above conditions. At 20° C. the 85 and 110 kD proteins remained bound in the presence of either 2 M NaCl plus 0.5% Triton X-100, 5 M NaCl, 6 M Urea, 50 mM phosphotyrosine or up to 1 mg/ml free Y751 phosphopeptide. Several alternative elution protocols were investigated without success. An elution medium supplied with the Actigel resin was able to remove both proteins but led to a complete loss of activity. Interestingly no suitable conditions could be established whereby the 110 kD, but not the 85 kD, subunit was released from the column suggesting that the interaction between the 110 and 85 kD subunits is of high affinity. Elution of bound proteins was routinely carried out by heating the resin to 80° C. for 3 min in the present of 5 mM phosphate buffer (pH 7.0), 0.1% SDS, 0.1 mM DTT, 10% glycerol. The phosphopeptide column could be simply regenerated following elution by extensive washing in binding buffer (FIG. 3, lanes 4 and 5) and could be successfully used at least ten times before any deterioration in binding was observed.

Analysis of the p85 and 110 kD Proteins Bound to the Phosphopeptide Column

The relationship of the 85 kD proteins observed to bind to the Y751 phosphopeptide column to the recently cloned p85α and p85β proteins was investigated using the polyclonal antisera generated against the predicted C-terminal 12 and 18 amino acids of p85α and p85β, respectively. Despite the high degree of overall sequence similarity between p85α and p85β, the amino acid sequence over this segment is significantly different and thus p85α or p85β specific antisera were expected to be produced. Furthermore the amino acid sequence corresponding to this peptide in p85α is completely conserved between human, bovine and murine cDNAs suggesting that antibodies generated against this sequence might be useful for studying the expression of different p85 proteins in species other than bovine (Escobedo et al, 1991b; Otsu et al, 1991; Skolnik et al, 1991). The corresponding region of p85β in species other than bovine is currently unknown.

The p85 antisera generated against these peptides could specifically immunoprecipitate the appropriate species of expressed recombinant p85 from either COS-1 or Sf9 cells but were not very efficient at immunoprecipitating PI3-kinase activity from either cell lines or from the partially purified bovine brain PI3-kinase preparation. However, these antisera were found to work well in Western blots. The data presented in FIG. 4 shows that these two antisera specifically recognized expressed p85 proteins present in either COS cells or in Sf9 cells. Longer exposures also revealed the endogenous COS p85 protein(s), but no such proteins were detected in Sf9 cells with these antisera. No cross reactivity was observed even at high concentrations of the recombinant proteins suggesting that they are specific for p85α (FIG. 4, panel A) and p85β (FIG. 4, panel B) respectively. The ability of these antisera to interact with the appropriate p85 species was demonstrated to be completely blocked in the presence of the appropriate peptide used ot raise the antisera (FIG. 4, panel C). The p85 species in the two peaks of bovine brain PI3-kinase activity which bound to the Y751 phosphopeptide column was found to react exclusively with the anti C-terminal antisera raised against the p85a specific sequence (FIG. 4, panel A). Following immobilisation of the bovine brain PI3-kinase material on the Y751 phosphopeptide column, all the p85α immunoreactive material was bound to the column with none detectable by either silver staining or Western blot analysis in the supernatant (FIG. 4, panel D).

For sequence analysis of the PI3-kinase complex, the 110 and 85 kD subunits were eluted from the column, following extensive stringent washing, by briefly boiling the resin in 5 mM phosphate buffer (pH 7.0), 0.1% SDS, 0.1 mM DTT, 10% glycerol. Preparation of both 85 and 110 kD proteins for digestion with lysylendopeptidase and subsequent sequence analysis were performed in accordance with the protocol given hereinbefore. Amino acid sequence analysis of a lysylendopeptidase C digest of the p85 protein bound to be Y751 phosphopeptide column confirmed that the p85 protein present in both peak 1 and peak 2 from the mono Q column were identical to the previously cloned p85α (Otsu et al, 1991). No peptides corresponding to p85β were found in either peak. Extensive sequencing of the 110 kD protein affinity purified from both mono Q peak 1 and peak 2 material enabled the isolation of a novel cDNA (see below).

Specificity of Binding of the Purified Bovine Brain PI3-kinase

In order to evaluate the specificity of the Y751 phospopeptide column for purifying the PI3-kinase, other phosphopeptide columns were prepared using peptides based on the amino acid sequences which surround known protein-tyrosine kinase phosphorylation sites. Tyrosine 857 is the other major autophosphorylation site in the human PDGF β-receptor and has been shown to be required for the binding of GAP, but not for association with the PI3-kinase (Kazlauskas & Cooper, 1989, 1990; Kazlauskas et al, 1991). For a direct comparison with the Y751 peptide a 17 amino acid peptide centred around tyrosine residue 857 was synthesized (see Table 2 above). A comparison the proteins from baculovirus expressing p85α Sf9 cell lysate or from bovine brain PI3-kinase fractions from mono Q peak 1 (P1) and peak 2 (P2) binding to either the Y751 (panel A) or Y587 (panel B) phosphopeptide columns is shown in FIG. 5. Whereas the baculovirus expressed p85α is observed to bind both columns to a similar extent, the 85 and 110 kD proteins from both peaks of activity are seen only to bind to the Y751 phosphopeptide column. Similarly, PI3-kinase activity is only found associated with the Y751 phosphopeptide column (FIG. 7, panel B).

To determine whether this binding specificity could be extended several other peptides were synthesized based on known tyrosine autophosphorylation sites (see Table 2 above). A shorter, 11 amino acid version of the Y751 peptide, termed Y751S, was also synthesized in an attempt to further refine the minimal SH2 recognition domain required. Two other peptides containing the YXXM motif were prepared, one based on the seqeunce around tyrosine 740 of the PDGF-β receptor, a second residue within the PDGF receptor kinase insert which may play a role in PI3-kinase binding (Escobedo et al, 1991a), and the second based around tyrosine Y1313 of Met, the hepatocyte growth factor receptor. To introduce a totally random sequence the synthetic peptide poly Glu:Ala:Tyr (6:3:1) was also phosphorylated and coupled to the Actigel matrix. Finally the peptides surrounding the two major phosphorylation sites from pp60$^{c-src}$, Y416 and Y527, were purchased and synthesized respectively. All peptides efficiently phosphorylated specifically on tyrosine residues using the EGF receptor and then were purified by HPLC as described above for the Y751 phosphopeptide.

Baculovirus expressed bovine p85α and p85β were chosen to test these columns (Otsu et al, 1991). Binding analysis was carried out under identical conditions to those previously established for the Y751 phosphopeptide column. Somewhat unexpectedly the baculovirus expressed p85 subunits bound to all phosphopeptide columns tested (see FIG. 7, panels A and B). They did not however bind to identical columns containing non-phosphorylated peptides (FIG. 6, panels A and B, lane 1 and data not shown). However when partially purified bovine brain PI3-kinase was applied to these columns it was found to bind exclusively to the phosphopeptide columns containing a YXXM motif (see FIG. 7 and FIG. 8, panel A).

That the Y751S phosphopeptide column appears to be as efficient at binding the active PI3-kinase complex as the longer Y751 phosphopeptide column suggests that the consensus sequence recently proposed by Cantley et al, (1991) does indeed contain all the sequence data necessary for correct recognition by the PI3-kinase SH2 domain (FIG. 8, panel B).

Cloning of p110

C. Experimental Procedures

Materials

Restriction enzymes and DNA modification enzymes were obtained from standard commercial sources and used according to the manufacturer's recommendations. Oligonucleotides were synthesized on an Applied Biosystems 380B DNA synthesizer and used directly in subsequent procedures.

Cells

The SGBAF-1 cell line was established by transfection of bovine adrenal cortex zona faciculata cells with pSV3neo as previously described for other cell types (Whitley et al, 1987). SGBAF-1 cells and COS-1 cells were maintained in Dulbecco's modified eagle medium (DMEM) containing a 10% foetal calf serum (FCS). Maintenance of Spodoptera frugiperda (Sf9) cells was carried out as described by Summers and Smith, 1987.

Protein Purification and Amino Acid Sequence Determination

The purification of the p85α and p110 proteins by chromatography on a peptide affinity column corresponding to amino acids 742–758 of the kinase insert region of the human PDGF-β receptor has been described above. The method used for the final purification of p110 for amino acid sequence analysis was in accordance with the Protocol given hereinbefore. This procedure was carried out on three separate PI3-kinase preparations. A fourth preparation was eluted from the matrix as before and boiled for 5 min. After cooling, the sample was diluted with 25 mM Tris-HCl, pH 8.8 and digested directly with lysylendopeptidase for 72 h at 30° C. Peptides were separated as above. Peptide sequences were determined using a modified Applied Biosystems 477A automated pulse-liquid sequencer.

mRNA Isolation and CDNA cloning

Total RNA was isolated from the SGBAF-1 by the method of Chirgwin et al. (1979) and poly(A)⁺ mRNA selected by chromatography on oligo-dT cellulose (Maniatis et al., 1982). An oligo-dT primed cDNA library of $5 \times 10^6$ primary recombinants was constructed in lambda Uni-Zap (Stratagene) from 5 µg of this mRNA using the Stratagene Uni-Zap cDNA cloning system. The construction of the total bovine brain cDNA library in lambda Uni-Zap has been described previously (Otsu et al, 1991).

Library Screening and Hybridizations

The unamplified SGBAF-1 cDNA library ($10^6$ recombinants) was plated on *E. coli* K12 PLK-F' (Stratagene) at a density of $10^5$ plaques per 15 cm dish and lifts taken in duplicate onto nitrocellulose membranes (Millipore). For screening, filters were prehybridized for at least 1 h at 42° C. in 6×SSPE, 0.5% SDS, 10×Denhardt's solution, 100 µg ml⁻¹ denatured sonicated herring sperm DNA (Sigma). Hybridization was carried out in the same solution containing 10 ng ml⁻¹ radiolabelled oligonucleotide. Oligonucleotides used were: Peptide N (MDWIFHT) (SEQ ID NO:11) 5'-AA(G/A)ATGGA(T/C)TGGAT(C/T/A)TT(T/C)CA(T/C)AC-3') (SEQ ID NO:12); Peptide J ( D D G Q L F H I D F G H F ) (SEQ ID NO:13) 5'-GATGATGGCCA(G/A)CTGTT(T/C)CA(T/C)AT(T/A)GA(T/C)TTTGGCCA (T/C)TT (SEQ ID NO:14). Oligonucleotides were labelled with ³²P at the 5' end in a 20 µl reaction containing 100 ng oligonucleotide, 1×kinase buffer (Promega), 0.1 mM spermidine, 5 mM dithiothreitol, 100 µCi [γ-³²P]ATP (5000 Ci mmol⁻¹, Amersham) and 2 µl (20 U) T4 polynucleotide kinase (Amersham). Filters were washed in 6×SSC, 0.1% SDS at room temperature and then subjected to autoradiography using Kodak XAR film.

Hybridizing clones were plaque-purified and rescued as plasmids according to the manufacturers instructions.

Characterization of CDNA Clones

Sequencing was carried out by the chain termination method using the Sequenase system (United States Biochemicals). Clones for sequencing were obtained by directed cloning of restriction fragments into M13 mp18 and mp19 vectors (Yanisch-Perron et al., 1985) and by making a series of exonuclease III mediated deletions (Henikoff, 1984; Pharmacia Exonuclease III deletion kit). DNA sequences were analysed on a MicroVAX computer using the Wisconsin (UWGCG: Devereux et al., 1984) sequence analysis package.

RACE PCR

RACE PCR was carried out essentially as published previously (Frohman et al., 1988; Harvey and Garlison, 1991). Briefly, first strand cDNA primed with random hexamers (Amersham) was synthesized from 1 µg of SGBAF-1 cell mRNA using the Stratagene first strand cDNA synthesis kit. First strand cDNA was isolated by isopropanol precipitation and tailed with oligo-dA using terminal deoxynucleotidyl transferase (BRL). PCR was performed using oligo 2224 (5'-AATTCACACACTGGCATGCCGAT) (SEQ ID NO:15) and adaptor-dT (5'-GACTCGAGTCGACATCGATTTTTTTTTTTTTTTT) (SEQ ID NO:16) as primers using a Perkin Elmer/Cetus Tap polymerase PCR kit (conditions: 94° C. 1 min, 35° C. 1 min, 72° C. 2 min, 30 cycles). Products were fractionated on a 1.5% low melting point agarose gel and visualized by staining with ethidium bromide. The gel was sliced into 6 bands (size range 150–2000 bp) and DNA isolated from each gel slice. A further round of PCR was performed on this DNA using oligonucleotide 2280 (5'-TTTAAGCTTAGGCATTCTAAAGTCACTATCATCCC) (SEQ ID NO:17) and adaptor (5'-GACTCGAGTCGACATCGA) (SEQ ID NO:18) as primers (conditions: 94° C. 1 min, 56° C. 1 min, 72° C. 2 min, 35 cycles). Products were fractionated on an agarose gel and visualised by staining with ethidium bromide. A band 250 bp shorter than the size of the DNA in the gel slice used for the PCR was expected. An intensely staining band of 350 bp obtained from the ~600 bp gel slice was excised, digested with Hindlll and Sall and ligated into Bluescript KS- digested with Hindlll and Xhol to give plasmid pBS/race. Two independent inserts were completely sequenced.

Southern Transfer Hybridizations

High molecular weight DNAs were isolated from cell lines by standard techniques (Maniatis et al, 1982). DNAs were digested with restriction endonucleases, fractionated through 0.5% agarose gels and transferred to nitrocellulose (BA85, Schleicher and Schuell) as described in Maniatis et al (1982). Prehybridization was carried out in 1 M NaCl, 10×Denhardt's solution, 50 mM Tris-HCl (pH 7.4), 10 mM EDTA, 0.1% SDS and 100 µg ml⁻¹ denatured sonicated herring sperm DNA at 65° C. Hybridization was carried out overnight in the same solution containing 20 ng ml⁻¹ radiolabelled probe fragment (0.88 kb Xbal-Psti fragment: Probe a, FIG. 9, lower panel) of specific activity >$10^8$ dpm µg⁻¹). Probe fragments were isolated from agarose gels be electroelution (Maniatis et al, 1982) and labelled by nick translation (Rigby et al, 1977) using [α-³²P] dATP(>3000 Ci mmol-1, Amersham). Membranes were washed extensively in 0.1×SSC, 0.1% SDS at 68oC or at 50° C. in 0.5 ×SSC, 0.1% SDS to detect related sequences, and subjected to autoradiography with Kodak XAR film.

Northern Transfer Hybridizations

Poly(A)⁺ RNA from total bovine brain or the SGBAF-1 cell line was modified with DMSO and glyoxal and fractionated on a 0.9% agarose gel run in 10 mM phosphate buffer (pH 7.5) (Maniatis et al, 1982). Nucleic acid was transferred to nylon membranes (Hybond-N, Amersham) and filters baked dry. Prehybridization was carried out at 60° C. in 50% formamide, 5×SSPE, 5×Denhardt's solution, 0.2% SDS, 200 μg ml$^{-1}$ denatured sonicated herring sperm DNA and 200 μg ml$^{-1}$ yeast RNA. Hybridization was carried out in the same solution containing 1×10$^7$ cpm ml$^{-1}$ antisense RNA probe. Probe was prepared by in vitro transcription of a 2 kb fragment (nucleotides 598–2608; Probe b, FIG. 9, lower panel) subcloned in pSPT19 (Boehringer), using SP6 RNA polymerase (Amersham) and [α$^{32}$-p] UTP (Amersham) according to the manufacturers conditions. Membranes were washed in 0.1×SSC, 0.1% SDS at 60° C. Filters were treated with 1 μg ml$^{-1}$ RNAase A (Sigma) in 2×SSC for 15 min at room temperature and the filter rinsed at 50° C. in 0.1×SSC. Filters were then subjected to autoradiography against Kodak XAR film at −70° C.

PCR Determination of p85α and p110 mRNA

For p85α 125 ng of poly (A)$^+$ RNA was reverse transcribed with 2.5 units rTth DNA polymerase (Perkin-Elmer-Cetus) at 70° C. for 10 min in a 10 μl reaction containing 10 mM Tris-HCl (pH 8.3), 90 mM KCl, 1 mM MnCl, 0.5 mM dNPT mixture and 1.2 μM antisense primer (5'-CAGGCCTGGCTTCCTGT) (SEQ ID NO:19). For DNA polymerization the reaction volume was adjusted to 50 μl by adding a single mix giving the following final concentrations: 5% (v/v) glycerol, 10 mM Tris-HCl (pH 8.3), 100 mM KCl, 0.75 mM EGTA, 0.05% (v/v) Tween 20, 2 mM MgCl$_2$, 0.24 μM sense primer (5'-AACCAGGCTCAACTGTT) (SEQ ID NO:20). PCR was then performed under the following reaction conditions: 92° C. 1 min, 58° C. 1 min, 72° C. 1 min for 25 cycles on a Perkin Elmer-Cetus DNA thermal cycler.

Conditions for p110 were similar except concentration of the antisense primer (5'-TGCTGTAAATTCTAATGCTG) (SEQ ID NO:21) was increased to 4.8 μM during the reverse transcription step. DNA polymerisation conditions were the same except the final MgCl$_2$ concentration was increased to 2.5 mM and both primers (sense primer=5'-GTATTTCATGAAACAAATGA) (SEQ ID NO:22) were present at a final concentration of 0.96 μM. Taq DNA polymerase (Promega) was also added at 0.03 U μl$^{-1}$. PCR was performed as follows: 92° C. 30 sec, 54° C. 5 sec, 72° C. 30 sec for 35 cycles. 20 μl of each reaction was run on a 3% agarose gel (Maniatis et al, 1982) and visualised by staining with ethidium bromide.

Antibodies and Immunoprecipitations

For the preparation of the anti C-terminal p110 antiserum, peptide CKMDWIFHTIKQHALN (SEQ ID NO:23) was synthesized by FMOC chemistry and purified by HPLC. It was then coupled to KLH using glutaraldehyde, and injected into the lymph nodes of rabbits using methods described in Kypta, R M et al., (1990), Cell 62, 481–492. Positive antisera as determined by enzyme-linked immunoassay were affinity purified on specific peptide-Actigel affinity columns. Anti-p85α (Otsu et al, 1991) and anti CSF-1 receptor (Ashmun et al., 1989) antisera are previously documented. Immunoprecipitations were carried out as described in Otsu et al., 1991.

PI3-kinase Assay

The assay for PI3-kinase activity was carried out as described by Whitman et al. (1985).

Expression of p110 in Sf9 Cells

To clone the p110 coding region into the baculovirus transfer vector p36C (Page, 1989) a Sau 3A1 site (GGATCA) present 10 nucleotides upstream from the initiation codon (see FIG. 9) was changed to a BamHl (GGATCC site by PCR mediated mutagenesis. Briefly, a sense oligonucleotide substituting C for A at position 6 of the Sau3Al site was used in a PCR reaction with an antisense primer comprising nucleotides (102–124) of the p110 sequence (see FIG. 9) using Vent polymerase (New England Biolabs). Template DNA was random-primed first strand cDNA prepared from SGBAF-1 cell mRNA as described above; PCR conditions: 94° C. 1 min, 50° C. 1 min, 72° C. 2 min, 35 cycles. The PCR product was digested with BamHl-EcoNl and a 118 bp fragment isolated from a low melting point agarose gel. This BamHl-EcoNl fragment was cloned into p110/2.2 digested with BamHl (present in vector sequences) and EcoNl (nucleotide=108) giving plasmid p110/(BamHl). The BamHl-EcoNl fragment of p110/(BamHl) was sequenced and found to agree with that previously determined. A 3.4 kb BamHl-Kpnl (Kpnl site present in the vector) fragment was isolated from p110/(BamHl) and ligated into p36C baculovirus transfer vector (Page, 1989) previously digested with the same enzymes. Recombinant viruses were obtained as described in Summers and Smith (1987). Sf9 cells were infected at a multiplicity of infection of 10 with recombinant viruses in IPL-41 media supplemented with 10% FCS. Cells were harvested and lysed 2 days post-infection in EB lysis buffer (20 mM Tris-HCl (pH 7.4), 50 mM NaCl, 50 mM NaF, 1% NP40, 1 mM EDTA, 500 μM sodium orthovanadate, 2 mM PMSF, 100 Kallikrein inhibitor units of Aprotinin ml$^{-1}$) (Kazlauskas and Cooper, 1989) and lysates were analysed by immunoappreciation.

Association of p110 and p85α with CSF-1 Receptor

This assay was performed essentially as described by Kazlauskas and Cooper (1990). Sf9 cells were infected as already described and lysed 48 h post-infection in EB lysis buffer. CSF-1 receptor was immunoprecipitated from Sf9 cells and collected on Protein A-Sepharose beads. The immunocomplex was then subjected to extensive washing (3 times with EB lysis buffer, twice with kinase buffer; 50 mM HEPES (pH 7.4), 150 mM NaCl, 0.02% Triton X-100, 12 mM MgCl$_2$, 2 mM MnCl$_2$, 10% glycerol, 500 μM sodium orthovanadate) and the receptor phosphorylated for 15 min at 20° C. with ATP. The precipitates were then washed again to remove free ATP and incubated for 2 h at 4° C. with cell lysates prepared from Sf9 cells infected with viruses expressing (i) p85α, (ii) p110 or (iii) co-infected with viruses expressing p85α and p110. The immune complexes were washed and assayed for associated PI3-kinase activity.

Expression of p85α and p110 in COS-1 Cells

For transient expression of p85α in COS-1 cells the coding region for p85α was cloned into the adenovirus late promoter based expression vector pMT2 (Kaufman et al, 1989) as previously described (Otsu et al, 1991). For expression of the p110 cDNA plasmid pSG5-p110 was constructed as follows. The 3.4 kb BamHl-Hindlll fragment from cDNA p2.1 was ligated into pSG5 (Stratagene) cut with BamHl and Bglll, the Hindlll and Bglll overhangs of p2.1 and pSG5 respectively, being filled in with Klenow polymerase. This gave construct pSG5.2. Plasmid pBS/race (above) was digested with EcoRl and Hindlll, the 350 bp band gel purified by electroelution (Maniatis et al, 1982) and further digested with Sau3Al and Bsml. This mixture was then added to the gel purified Bsml-BstMl fragment from p2.1 and ligated in a three fragment ligation to pSG5.2 digested with BamHl and BstXl. 5 μg of each DNA was transfected into 10 cm dishes of 80% confluent COS-1 cells using Lipofectin (BRL) under conditions suggested by the manufacturers. Lysates were analysed by immunoprecipitation with anti-p85α polyclonal antiserum or with anti-p110 C-terminal peptide antiserum. Immunocomplexes collected on Protein A-Sepharose beads were analysed either on 10% SDS-PAGE gels followed by autoradiography or subjected to in vitro PI3-kinase assays as described.

D. Results of Cloning

CDNA Cloning and Deduced Amino Acid Sequence of p110

Initially, an oligo(dT) primed bovine brain cDNA library (Otsu et al, 1991) was screened with oligonucleotide probes made against peptides J and N (see FIG. 9). No hybridizing clones were detected. Therefore, a new cDNA library of $5\times10^6$ primary recombinants was constructed from mRNA isolated from a pSV3neo transfected bovine adrenal cortex zona fasciculate cell line (SGBAF-1), which was known to contain PI3-kinase activity (Otsu et al, 1991). Screening of $1\times10^6$ primary recombinants from this library with the same oligonucleotides led to the detection of 66 clones positive with both probes. Twenty overlapping clones were characterized and found to possess inserts from 1–4 kb. The clone with the longest insert representing coding sequence (clone p110/2.1) was completely sequenced. This revealed a potential open reading frame (ORF) of 1053 amino acids with a predicted molecular weight of 123 kD. The ORF contained all the sequenced peptides, but was not preceded by in-frame stop codons. Since the predicted size of the p110 protein from SDS gels is 110 kD, it was possible that the protein could initiate from an internal methionine within this ORF. Expression studies carried out in COS-1 cells using methionines 16, 30, 123 and 130 as potential start codons (initiation at Met 123 would give rise to a protein of 110 kD) did not lead to the syntheses of a protein corresponding to p110 or any augmentation of PI3-kinase activity in these cells. This suggested p110/2.1 is missing 5' coding sequence and that either p110 protein runs anomalously on SDS-PAGE gels or that it is synthesized as part of a larger precursor molecule. Characterization of the remaining 46 positive clones initially isolated, showed that all had inserts shorter than that in clone p110/2.1. To further extend the p110/2.1 cDNA in the 5' direction a RACE (rapid amplification of cDNA ends) polymerase chain reaction (PCR) (Frohman et al, 1988; Harvey and Garlison, 1991) was used. Two independent products which extended the known nucleotide sequence were characterized (see FIG. 9, lower panel). The nucleotide and deduced amino acid sequences for the coding region of the composite cDNA are presented in FIG. 9. The putative initiation codon is preceded by an in-frame stop codon and occurs in a Kozak consensus sequence (Kozak, 1987) for the initiation of translation (data not shown). The deduced amino acid sequence encodes a protein of 1068 amino acids with a calculated relative molecular mass of 124,247.

Analysis of the p110 Nucleotide and Deduced Amino Acid Sequences

The coding region of the cDNA for p110 is extremely A+T rich (G+C content=39.3%) which is reflected in the failure to use codons TCG (Serine) and GTC (Valine). When the p110 amino acid sequence was compared with sequences in the Swissprot and NBRF protein databases, significant homology was found to only one protein, Vps34p (FIG. 10). This is a rare 100 kD protein from Saccharomyces cerevisiae involved in the sorting of proteins into the yeast vacuole and in the vacuole morphogenesis during budding (Herman and Emr, 1990). A search of the p110 sequence for amino acids conserved in the active sites of kinases, reveals $G_{842}$, $K_{863}$, $D_{916}$ $N_{921}$, and the DFG triplet at residues 933–935 (these residues are marked in FIG. 2B) which might be homologous to $G_{52}$, $K_{72}$, $D_{166}$, $N_{171}$ and the DFG triplet at residues 184–186 in cAMP-dependent protein kinase (Knighton et al, 1991a,b). Equivalent residues are present in Vps34p and are also marked in Figure X. The glycine rich P-loop (Saraste et al., 1990), found in many kinases (Hanks et al., 1988), does not appear to be present in either p110 or Vps34p.

Genomic Southern Blot Analysis of p110 Genes

Given the occurrence of at least two forms of p85 (Otsu et al, 1991), Southern blot analysis was used to analyse the number of p110 related genes which occur in genomic DNA isolated from bovine, human and rat sources. The analysis clearly provides evidence for a second, closely related, gene in rat and human genomic DNA (e.g. compare FIG. 11A lanes 4 and 9 with FIG. 11B lanes 4 and 9). For bovine DNA there appear to be no hybridization signals removed by washing at higher stringency (compare FIG. 11A lanes 1, 2 and 3 with FIG. 11B lanes 1, 2 and 3). However, it is possible that a related gene exists in bovine DNA, but, either it does not cross-hybridize under the conditions used, or it is too similar in sequence to be detected by differential washing.

Expression of p110 Cells and Tissues

Figure 12A:
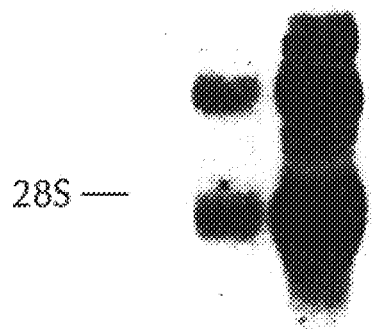
Figure 12B:
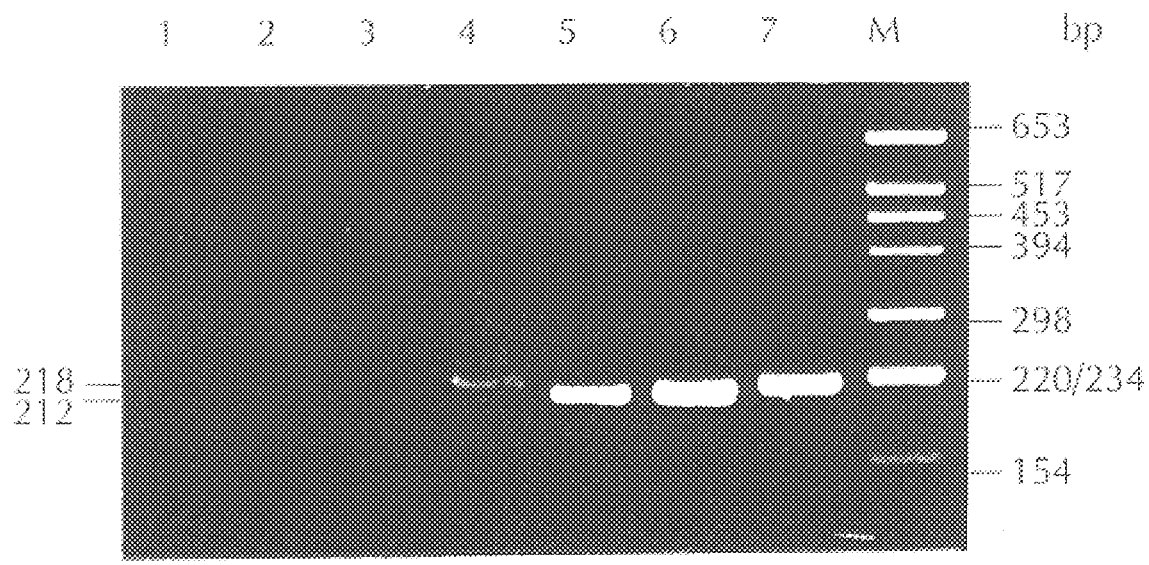
Figure 12C:
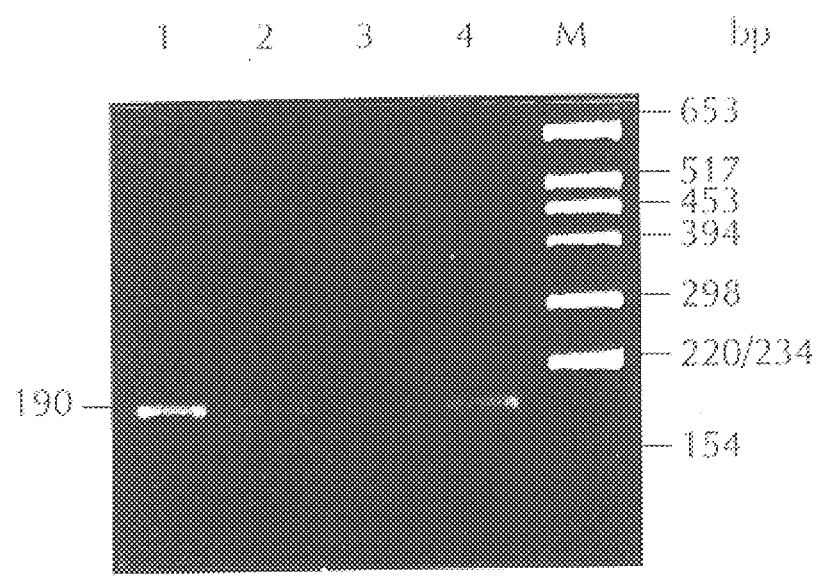
Figure 13A:
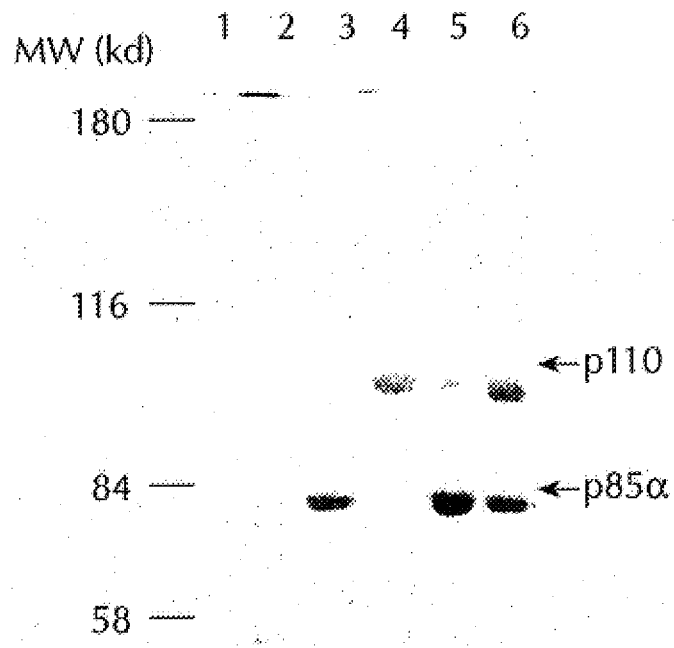
Figure 13B:
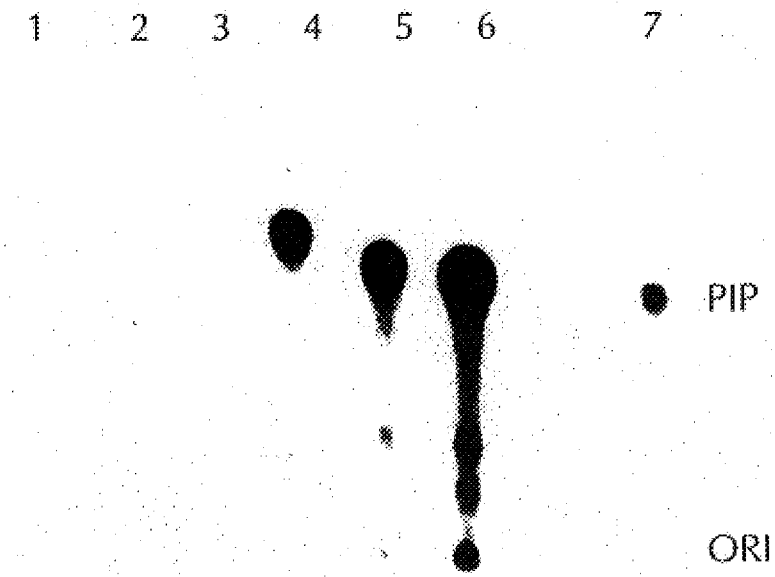

A northern blot analysis carried out on mRNA isolated from the SGBAF-1 cell line and total bovine brain is shown in FIG. 12A. Both mRNA samples contain major p110 specific transcripts of 4.8 kb and 9 kb, although there is substantially more p110 message present in mRNA isolated from SGBAF-1 cells (FIG. 12A, lane 2) than that isolated from total bovine brain (FIG. 12A, lane 1). A PCR based study was performed to examine the distribution and conservation of p110 mRNA in cell lines and tissue from several species. Amplification of a p110 specific fragment is seen for three human mRNAs (218 bp; FIG. 12B lanes 1, 2 and 3) and two bovine mRNAs (212 bp; FIG. 12B, lanes 5 and 6). Similar sized fragments are amplified from cell lines of simian and porcine origin (FIG. 12B, lanes 4 and 7, respectively), indicating the existence of a p110 homologue in these species. An additional band of 300 bp is amplified from bovine brain mRNA (FIG. 12B, lane 5) and its identity is currently being investigated. Since PI3-kinase activity may reside in a p85α/p110 complex (Carpenter et al, 1990; Otsu et al., 1991; Shibasaki et al., 1991), some of these cell lines were examined to see whether messages for p85α and p110 are co-expressed. Amplification of a p85α specific 190 bp fragment is seen for the three human omission (FIG. 12C, lanes 1, 2 and 3) cell lines and one simian (FIG. 12C, lane 4) cell line analysed. Thus, at least in these four cell lines, messages for p85α and p110 are co-expressed.

p110 CDNA Encodes a Protein of Apparent Molecular Weight 110 kD which Possesses PI3-kinase Activity To demonstrate that the p110 cDNA encodes the 110 kD subunit of PI3-kinase, it was expressed in the baculovirus expression system (Summers and Smith, 1987). Immunoprecipitation with an anti-p110 antiserum from Spodoptera frugiperda (Sf9) cells infected with the p36C-p110 virus revealed a novel protein of apparent molecular weight 110 kD (FIG. 13A, lane 4) which co-migrated with the p110 PI3-kinase subunit purified from bovine brain. No such protein was seen in anti-p110 immunoprecipitates prepared from cells infected with a control wild-type virus (FIG. 13A, lane 2). This baculovirus expressed p110 was used to examine whether p110, alone, possesses catalytic activity or whether a p85α/p110 complex is required. When assayed, p110-containing immunoprecipitates were found to possess significant levels of PI3-kinase activity (FIG. 13B, lane 4), the identity of the lipid product being confirmed as PI(3)P by HPLC analysis. No activity was detected in anti-p110 immunoprecipitates prepared from control infected cells (FIG. 13B, lane 2). These results clearly demonstrate that the p110 subunit of PI3-kinase is sufficient for catalytic activity.

p110 Expressed in Insect Cells Forms a Stable Complex with p85α

Since PI3-kinase purified from bovine brain is a complex of p85α and p110, the ability of p85α and p110 expressed in insect cells to reconstitute an active p85α/p110 complex was examined. Baculoviruses expressing either p85α (pAcC4-p85α; Otsu et al, 1991) or p110 (p36C-p110) were infected separately, or together, into Sf9 cells and expressed proteins analysed as described in experimental procedures. Immunoprecipitates of p85α alone (FIG. 13A, lane 3) were inactive in a PI3-kinase assay (FIG. 13B, lane 3) as previously demonstrated (Otsu et al, 1991). In double infection experiments, both p85α and p110 were detected in either anti-p85α (FIG. 13A, lane 5) or anti-p110 (FIG. 13A, lane 6) immunoprecipitates. As neither subunit-specific antiserum recognises the other subunit (see FIG. 15A, lane 3; FIG. 15C, lane 2), the simplest interpretation of this data is that, when expressed in Sf9 cells, p110 and p85α (FIG. 13B, lane 5) or the anti-p110 antisera (FIG. 13B, lane 6) were both active. Neither antiserum immunoprecipitated endogenous PI3-kinase activity from Sf9 cells infected with wild-type virus (FIG. 13B, lanes 1 and 2).

PI3-kinase Activity Expressed in Sf9 Cells Can Associate with the Activated CSF-1 Receptor PI3-kinase activity has been shown to associate with many activated PTK receptors, but particularly well studied have been those receptor PTKs possessing a kinase insert region, e.g., PDGF-β receptor (Coughlin, S R et al., (1989), Science 243, 1191–1193 and the CSF-1 receptor (Varticovski et al, 1989; Shurtleff et al, 1990). An in vitro association assay (Kazlauskas and Cooper, 1990) was used to study the association of PI3-kinase activity expressed in insect cells with the activated CSF-1 receptor. FIG. 14 shows that baculovirus expressed PI3-kinase activity can associate with the CSF-1 receptor, but only from an Sf9 cell lysate containing both p85α and p110 (FIG. 14, lane 2), and only when the receptor has been phosphorylated prior to incubation with Sf9 cell lysate (compare FIG. 14, lanes 2 (+ ATP) and 3 (− ATP)). No PI3-kinase activity associates with CSF-1 receptors incubated with Sf9 cells lysates containing p85α alone (FIG. 14, lane 4) or p110 alone (FIG. 14, lane 5). No activity is found associated with the CSF-1 receptor immunoprecipitated from Sf9 cells (FIG. 14, lane 1). Thus, PI3-kinase subunits expressed in insect cells can be used to reconstitute an active p85α/p110 complex that binds to a phosphorylated PTK receptor.

Expression of PI3-kinase in COS-1 Cells

The results shown above were all obtained from expression studies carried out in insect cells. In order to study p110 and its interaction with p85α in a mammalian cell system, transient co-expression studies in COS-1 cells were performed. The p110 cDNA was cloned into the SV40 based expression vector, pSG5 (giving plasmid pSF5-p110) and transfected into COS-1 cells, either alone or together with a p85α expression construct, pMT2-p85α (Otsu et al., 1991). To enable proteins to be more easily visualised transfected COS-1 cells were metabolically labelled with $^{35}$S-methionine for 3–4 h prior to lysis. Radiolabelling at this time results in preferential labelling of proteins synthesized from transfected constructs. Cell lysates were immunoprecipitated with either anti-p85α (FIG. 15, panels A and B) or anti-p110 antisera (FIG. 15, panels C and D). Immunoprecipitated proteins were either visualised by autoradiography following fractionation on SDS-PAGE gels (FIG. 15, panels A and C) or subjected to an in vitro PI3-kinase assay (FIG. 15, panels B and D).

Transfection of pMT2-p85α resulted in a significant elevation of p85α over the background level due to endogenous simian p85α—compare FIG. 15A, lanes 2 and 4 with FIG. 15A, lane 1. In p85α/p110 co-transfectants, the anti-p85α antiserum co-immunoprecipitates p85α and p110 (FIG. 15A, lane 4), demonstrating the existence of a p85α/p110 complex. When assays for PI3-kinase activity were performed on the anti-p85α immunoprecipitates, enhanced activity (10 fold over the background due to endogenous simian PI3-kinase) was only detected with immunoprecipitates which contained both p85α and p100 (compare FIG. 15B, lane 4 with FIG. 15B lanes 1, 2 and 3). These results demonstrate that in COS-1 cells, as in Sf9 cells, the p110 cDNA directs the synthesis of a protein of molecular weight 110 kD, which associates with p85α to give a p85α/p110 complex that possesses PI3-kinase activity.

However, when proteins were immunoprecipitated from the same lysates with the anti-p110 antiserum and PI3-kinase assays performed, the results were surprising. As expected the anti-p110 antiserum immunoprecipitated p110 from cells transfected with pSG5-p110 (FIG. 15C, lane 3). However, in addition, it would only immunoprecipitate free p110 from lysates prepared from cells co-transfected with p85α and p110 (FIG. 15C, lane 4) even though p85α/p110 complex was present in these lysates (FIG. 15A, lane 4). When assayed for PI3-kinase activity, no activity above that present in control immunoprecipitates (FIG. 15D, lanes 1 and 2), was present in p110 containing immunoprecipitates prepared from either p110 -transfected (FIG. 15D, lane 3) or, p85α and p110 co-transfected, cells (FIG. 15D, lane 4). Thus, the anti-p110 antiserum is capable of immunoprecipitating p110 from cell lysates of both infected Sf9 cells (FIG. 13A, lane 4) and transfected COS-1 cells (FIG. 15C, lane 3), but only the immunoprecipitates prepared from Sf9 cell lysates possess elevated levels of PI3-kinase activity (compare FIG. 13B, lane 4 and FIG. 15D, lane 3). Also, the anti-pilo antiserum immunoprecipitates the p85α/p110 complex when expressed in Sf9 cells, but not when expressed in COS-1 cells.

As indicated above, analysis of the cloned p110 cDNA shows it to encode a protein of 1068 amino acids with a calculated molecular weight of 124 kD. The reason for the difference in size between the calculated (124 kD) and observed molecular weight value 110 kD is unclear, but it is known that many proteins migrate anomalously on SDS-PAGE gels. Expression of the protein encoded by this ORF in Sf9 cells, COS-1 cells, reticulocyte lysate and *E. coli* all result in the production of a protein of apparent molecular weight 110 kD.

The deduced amino acid sequence of p110 contains all the peptide sequences determined by protein sequence analysis. Since the peptides were obtained from a lysylendopeptidase digestion, it is expected that they should all be preceded by a lysine residue. This is true in every case, except for peptide A which is preceded by an arginine residue (Arg 162). Nucleotide sequence data obtained from another cDNA clone covering this region confirms the presence of an arginine residue in this position. Thus, it seems likely that cleavage at this site by lysylendopeptidase results from a sequence polymorphism.

When a database search was performed on the p110 sequence no significant homology was detected with any proteins known to be involved in inositol lipid metabolism. However, as noted, p110 did show significant homology throughout its C-terminal half to the Saccharomyces cerevisiae protein Vps34p. The possibility that Vps34p is a yeast PI-kinase is currently being investigated. If p110 and Vps34p are homologous proteins then it is interesting to speculate that p110 might also be involved with protein targeting and/or vesicular transport. PI3-kinase activity has previously been implicated in vesicle mediated responses in higher eukaryotes. Hence, PI3-kinase activity is seen to increase following stimulation of platelets with thrombin (Kucera and Rittenhouse, 1990) and neutrophils with f-Met-Leu-Phe (Traynor-Kaplan et al, 1988). In both cases, ligand stimulation promotes the fusion of vesicular structures necessary for the biological response. A role for PI3-kinase in intracellular vesicles following the activation of PTKs has also been suggested (Cantley et al, 1991; Kelly et al, 1992).

Southern blotting data suggests there may be two genes for PI3-kinase in rats and humans. Evidence for the existence of a second gene in rat DNA is also provided by the results of Carpenter et al., (1990), who identified two forms of p110 in their purified PI3-kinase preparation. In situ hybridization confirms the presence of two closely related sequences in human DNA, although one could be a pseudogene. Two forms of p85 (p85α and p85β) have been characterized (Otsu et al, 1991), although only p85α is found associated with p110 in PI3-kinase from bovine brain. It is possible to speculate that p85β associates with a second form of p110.

Although, at present, the function of the 3-phosphorylated phosphoinositides produced by PI3-kinase is unclear, the availability of expression systems which allow their generation will aid in the determination of their function.

EXAMPLE 2

Using the bovine cDNA probe constituted by the XbaI-PstI fragment of the sequence of FIG. 9 (probe a, bottom panel) and genomic DNAs from several species, Southern blot analyses prove positive against the bovine probe in the following species:—bovine (calf thymus), human (HeLa cells), rat (liver), simian (COS cells), porcine (ZNR cells), chicken (from Promega), and Xenopus (liver).

The human cDNA was isolated from a cDNA library, made from mRNA isolated from the human cell line KGla using standard techniques. The probe was a partial cDNA from the second half of the bovine p110 cDNA. The probe was labelled with $^{32}$P and hybridised overnight to the library filters at 65° C. in 1 M NaPi, 7% SDS buffer. The filters were washed in 2×SSC at 50° C., and exposed to X-ray film at −70° C. The nucleotide sequence is shown in FIG. 16 together with the corresponding amino acid sequence. The human p110 sequence has 95% homology to the bovine p110 sequence at the DNA level and is 98% identical at the protein level (FIGS. 17 and 18). The protein sequence is shown in FIG. 19. Primers (357) AAG GAT CAG AAC AAT GCC T (SEQ ID NO:24) and (416) AGG CTT TCT TTA GCC ATC A (SEQ ID NO:25) were used to amplify, using RT-PCR (94° C. 30 sec 50° C. 30 sec, 72° C. 60 secs; for 35 cycles) the partial sequence of a highly related p110 gene (p110–11). P110–11 has 96% nucleotide homology to p110 (sequence not provided).

Two novel cDNAs related to p110 have been cloned. Degenerate primers were designed to conserved sequences between human p110 and the related yeast gene VPS34 (Sense (GDDLRQD) (SEQ ID NO:26) 5' GGN GAT/C GAT/C T/C TA/G CGN CAA/G GA-3' (SEQ ID NO:27) antisense (FHIDFGHF) (SEQ ID NO:28) 5'A/GAA A/GTG ICC A/GAA A/GTC A/G/TAT A/GTG A/GAA-3') (SEQ ID NO:29). These were used in RT-PCR reactions using mRNA from the human cell lines MOLT4 and U937 (94° C. 30 sec, 50° C. 30 sec, 72° C. 30 sec for 35 cycles). Two novel cDNA's, PITR-c and PITR-f, related to p110, were isolated. The PITR-c nucleotide sequence is shown in FIG. 20. This gene is highly related to the yeast gene VPS34, the VPS34 protein is involved in the protein sorting from the golgi to the vacuole and has an intrinsic PI3-kinase activity. The PITR-f nucleotide sequence is shown in FIG. 21 and is more similar to p110 than PITR-c and is likely also to possess PI3-kinase activity. The alignment of human p110, the human PI3-kinase related genes PITR-c and PITR-f and the yeast PI3-kinase VPS34 are shown in FIG. 22. The amino acids conserved in 3 or more of the proteins are shown in the upper case.

The interaction of the p85 and p110 subunits of PI3-kinase are thought to be required for the activity of the kinase in mammalian cells. Thus inhibiting the interaction between the subunits could provide a means of inhibiting the activity of this signal transduction pathway. In order to design reagents to p110 which will block the interaction, it is useful to define the region of p110 which binds to the p85 subunits. To do this a series of mutants were constructed which express various domains of the p110 protein (FIG. 23B). These fragments were expressed as GST fusion proteins in bacteria. The proteins were then bound to a glutathione sepharose column (Pharmicia) according to the manufacturer's instructions (Panayotou G et al (1992) EmboJ 11:4261–4272). The ability of these protein fragments to bind the p85 subunits was assessed by the ability of the column specifically to retain p85 subunits purified from baculovirus (Otsu et al(1991) Cell 65:91–104). As shown in FIG. 23A, only p110-N (αα1-128) was capable of binding the p85α and β subunits. To further characterise the binding domain, deletion mutants and PCR fragments were made from the p110-N fragment as shown in FIG. 24. The results in FIG. 25 demonstrate that a domain containing amino acids 19–110 of human p110 is sufficient to associate with the p85 subunits. Removal of a further 20 amino acids from either the amino or carboxy termini led to loss of binding activity. Now that this domain has been identified it allows the design of specific peptides, antibodies or small molecules which can inhibit the interaction between the subunits.

The invention includes a human PI3-kinase p110 subunit sequence comprising amino acids 19 to 110 of human p110, or an amino terminal truncated or carboxy terminal truncated derivative thereof having less than 20 amino acids deleted from the amino terminal or carboxy terminal end, respectively, but which is capable of binding to a PI3-kinase p85 subunit; and also included is a method of inhibiting p85 and p110 mammalian PI3-kinase subunit interaction, which comprises utilizing a molecule which blocks the binding domain located between amino acids 19 and 110 of human p110.

The invention further provides the use of a sequence or derivative as defined above in screening for a therapeutic or prophylactic agent which operates by inhibiting interaction between p85 and p110 mammalian PI3-kinase subunits.

References

Anderson, D et al., (1990), Science 250, 979–982.
Ashmum, R A et al., (1989), Blood 73, 827–837.
Auger, K R et al., (1989), J. Biol. Chem. 264, 20181–20184.
Auger, K R et al., (1991), Cancer Cells 3, 263–270.
Berridge, M J et al., (1989), Nature 341, 197–205.
Bjorge, J D et al., (1990), Proc. Natl. Acad. Sci. USA 87, 3816–3820.
Cantley, L C et al., (1991), Cell 64, 281–302.
Carpenter, C L et al., (1990), Biochemistry 29, 11147–11156.
Carpenter, C L et al., (1990), J. Biol. Chem. 265, 19704–19711.

Chan, T O et al., (1990), Mol. Cell. Biol. 10, 3280–3283.
Chirgwin, J M et al., (1979), Biochemistry 18, 294–299.
Cohen, B et al., (1990), Mol. Cell. Biol. 10, 2909–2915.
Cooper, J A et al., (1983), Methods Enzymol. 99, 387–402.
Coughlin, S R et al., (1989), Science 243, 1191–1194.
Courtneidge, S A et al., (1987), Cell 50, 1031–1037.
Devereux, J et al., (1984), Nucleic Acids Res. 12, 387–395.
Downes, C P et al., (1990), Eur. J. Biochem. 193, 1–18.
Downes, C P et al., (1991), Cellular Signalling 3, 501–513.
Enderman, G et al., (1987), Biochemistry 26, 6845–6852.
Escobedo, J A et al., (1988), Nature 335, 85–87.
Escobedo, J A et al., (1991a), Mol. Cell. Biol. 11, 1125–1132.
Escobedo, J A et al., (1991b), Cell 65, 75–82.
Frohman, M A et al., (1988), Proc. Nat. Acad. Sci. USA 85, 8998–9002.
Fukui, Y et al., (1989), Mol. Cell. Biol. 9, 1651–1658.
Graziani, A et al., (1991), J. Biol. Chem. 266, 22087–22090.
Hanks, S K et al., (1988), Science 241, 42–52.
Hanks, S K (1991), Current Opinion in Structural Biology 1, 369–383.
Harvey, R J et al., (1991), Nuc. Acids. Res. 19, 4002.
Henikoff, S (1984), Gene 28, 351–359.
Herman, P K et al., (1990), Mol. Cell. Biol. 10, 6742–6754.
Hu, P et al., (1992), Mol. Cell. Biol. 12, 981–990.
Kaplan, D R et al., (1986), Proc. Natl. Acad. Sci. USA 83, 3624–3628.
Kaplan, D R et al., (1987), Cell 50, 1021–1029.
Kaplan, D R et al., (1990), Cell 61, 125–133.
Kaufman, R J et al., (1989), Mol. Cell. Biol. 9, 946–958.
Kawasaki, H et al., (1990), Anal. Biochem. 186, 264–268.
Kazlauskas, A et al., (1989), Cell 58, 1121–1133.
Kazlauskas, A et al., (1990), EMB0 J. 9, 3279–3286.
Kazlauskas, A et al., (1990), Science 247, 1578–1581.
Kazlauskas, A et al., (1991), Cell Regulation 2, 413–425.
Kelly, K L et al., (1992), J. Biol. Chem. 267, 3423–3428.
Kemp, B E et al., (1990), TIBS 15, 342–346.
Knighton, D R et al., (1991a), Science 253, 407–414.
Knighton, D R et al., (1991b), Science 253, 414–420.
Koch, C A et al., (1991), Science 252, 668–674.
Kozak, M (1987), Nucl. Acids Res. 15, 8125–8148.
Kucera, G L et al., (1990), J. Biol. Chem. 265, 5345–5348.
Kypta, R M et al., (1988), EMBO J. 7, 3837–3844.
Kypta, R M et al., (1990), Cell 62, 481–492.
Lev, S et al., (1991), EMBO J. 10, 647–654.
Lips, D L (1989), J. Biol. Chem. 264, 8759–8763.
Majerus, P W et al., (1990), Cell 63, 459–465.
Maniatis, T et al., (1982) Molecular Cloning: a laboratory manual (Cold Spring Harbor Laboratory).
Margolis, B et al., (1990), EMBO J. 9, 4375–4380.
Matsuda, M et al., (1991), Mol. Cell. Biol. 11, 1607–1613.
Mayer, B J et al., (1990), Proc. Natl. Acad. Sci. USA 87, 2638–2642.
Mayer, B J et al., (1991), Proc. Natl. Acad. Sci. USA 88, 627–631.
Meisenhelder, J et al., (1989), Cell 57, 1109–1122.
McGlade, C J et al., (1992), Mol. Cell. Biol. 12, 991–997.
Moran, M F et al., (1990), Proc. Natl. Acad. Sci. USA 87, 8622–8626.
Morgan, S J et al., (1990), Eur. J. Biochem. 191, 761–767.
Morrison, D K et al., (1989), Cell 58, 649–657.
Otsu, M et al., (1991), Cell 65, 91–104.
Page, M J (1989), Nucl. Acids Res. 17, 454.
Pendergast, A M et al., (1991), Cell 66, 161–171.
Rhee, S G (1991), Trends Biochem. Sci. 16, 297–301.
Rigby, P W J et al.,(1977), I. J. Mol. Biol. 113, 237–251.
Robinson, J S et al., (1988), Mol. Cell. Biol. 8, 4936–4948.
Ruderman, N B et al., (1990), Proc. Natl. Acad. Sci. USA 87, 1411–1415.
Saraste, M et al., (1990), Trends Biochem. Sci. 15, 430–434.
Serunian, L A et al., (1989), J. Biol. Chem. 264, 17809–17815.
Shurtleff, S A et al., (1990), EMBO J. 9, 2415–2421.
Shibasaki, F et al., (1991), J. Biol. Chem. 266, 8108–8114.
Skolnik, E Y et al., (1991), Cell 65, 83–90.
Shurtleff, S A et al., (1990), EMBO J. 9, 2415–2421.
Stephens, L R et al., (1991), Nature 351, 33–39.
Summers, M D et al., (1987), A Manual of Methods for Baculovirus Insect Vectors and Insect Cell Culture Procedures; Texas Agri. Exp. Station Bull. No 1555.
Talmage, D A et al., (1989), Cell 59, 55–65.
Thom D, et al., (1977), Biochem. J. 168, 187–194.
Traynor-Kaplan, A E et al., (1988), Nature 334, 353–356.
Ullrich, A et al., (1990), Cell 61, 203–212.
Ulug, E T et al., (1990), J. Virol. 64, 3895–3904.
Varticovski, L et al., (1989), Nature 342, 699–702.
Varticovski, L et al., (1991), Mol. Cell. Biol. 11, 1107–1113.
Whitley, G S J et al., (1987), Mol. Cell. Endocrinol. 52, 279–284.
Whitman, M et al., (1985), Nature 315, 239–242.
Whitman, M et al., (1987), Biochem. J. 247, 165–174.
Whitman, M et al., (1988), Biochem. Biophys. Acta. 948, 327–344.
Whitman, M et al., (1988), Nature 332, 644–646.
Woodgett, J R (1989), Anal. Biochem. 180, 237–241.
Yanisch-Perron, C et al., (1985), Gene 33, 103–119.
Yu, J C et al., (1991), Mol. Cell. Biol. 11, 3780–3785.

We claim:

1. Isolated, human polypeptide which has PI3 kinase activity and a molecular weight of about 110 kilodaltons as determined by SDS-PAGE.

2. The isolated, human polypeptide of claim 1, having a molecular weight of about 124 kilodaltons based upon its amino acid sequence.

3. The isolated human polypeptide of claim 1, consisting of the amino acid sequence set forth in SEQ ID NO:32.

4. Method for screening a compound to determine if it is an antagonist of PI3 kinase, comprising combining said compound with the isolated human polypeptide of claim 1 in the presence of a cell which is stimulated to proliferate by PI3 kinase, and determining proliferation or lack thereof of said cell, wherein lack of proliferation is indicative of PI3 antagonist activity for said compound.

5. Method for determining PI3 kinase agonist activity of a compound, comprising combining said compound with the isolated human polypeptide of claim 1 in the presence of a cell which is stimulated to proliferate in the presence of a PI3 kinase, determining cell proliferation, and comparing said cell proliferation to a first measurement of cell proliferation in the presence of said isolated human polypeptide and the absence of said compound, wherein an increase in said proliferation in the presence of both said compound and said human polypeptide is indicative of PI3 kinase agonist activity for said compound.

6. Isolated polypeptide consisting of amino acids 19–10 of SEQ ID NO:32.

7. Isolated polypeptide selected from the group consisting of:

(a) amino acids 1–128 of SEQ ID NO: 32;

(b) amino acids 1–108 of SEQ ID NO: 32, and (c) amino acids 19–108 of SEQ ID NO: 32.

* * * * *

UNITED STATES PATENT AND TRADEMARK OFFICE
CERTIFICATE OF CORRECTION

PATENT NO. : 5,824,492
DATED : October 20, 1998
INVENTOR(S) : Hiles, et. al.

It is certified that error appears in the above-identified patent and that said Letters Patent is hereby corrected as shown below:

In column 17, line 45, change "ot" to - - to - -.
In column 18, line 17, change "comparison the" to - - comparison of the - -.
In column 19, line 36, change "fromthe" to - - from the - -.
In column 44, line 18, change "CDNA" to - - cDNA - -.
In column 27, line 56, change "conserved" to - - conserve - -.

Signed and Sealed this

Fifth Day of December, 2000

*Attest:*

*Attesting Officer*

Q. TODD DICKINSON
*Director of Patents and Trademarks*

SEQUENCE LISTING ( 1 ) GENERAL INFORMATION:

( i i i ) NUMBER OF SEQUENCES: 50

( 2 ) INFORMATION FOR SEQ ID NO: 1:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( x i ) SEQUENCE DESCRIPTION: SEQ ID NO: 1:

```
        Gly   Glu   Ser   Asp   Gly   Gly   Tyr   Met   Asp   Met   Ser   Lys
         1                 5                             10
```

( 2 ) INFORMATION FOR SEQ ID NO: 2:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( x i ) SEQUENCE DESCRIPTION: SEQ ID NO: 2:

```
    Asp   Met   Ser   Lys   Asp   Glu   Ser   Val   Asp   Tyr   Val   Pro   Met   Leu   Asp   Met
     1                 5                             10                                  15

Lys
```

( 2 ) INFORMATION FOR SEQ ID NO: 3:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( x i ) SEQUENCE DESCRIPTION: SEQ ID NO: 3:

```
    Cys   Asp   Glu   Ser   Val   Asp   Tyr   Val   Pro   Met   Leu
     1                 5                             10
```

( 2 ) INFORMATION FOR SEQ ID NO: 4:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( x i ) SEQUENCE DESCRIPTION: SEQ ID NO: 4:

```
    Ala   Arg   Asp   Ile   Met   Arg   Asp   Ser   Asn   Tyr   Ile   Ser   Lys   Gly   Ser   Thr
     1                 5                             10                                  15

Phe
```

( 2 ) INFORMATION FOR SEQ ID NO: 5:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( x i ) SEQUENCE DESCRIPTION: SEQ ID NO: 5:

```
    Glu   Phe   Cys   Pro   Asp   Pro   Leu   Tyr   Glu   Val   Met   Leu   Lys
     1                 5                             10
```

( 2 ) INFORMATION FOR SEQ ID NO: 6:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( x i ) SEQUENCE DESCRIPTION: SEQ ID NO: 6:

```
    Arg   Arg   Phe   Thr   Ser   Thr   Glu   Pro   Gln   Tyr   Gln   Pro   Gly   Glu   Asn   Leu
     1                 5                             10                                  15
```

( 2 ) INFORMATION FOR SEQ ID NO: 7:

( i ) SEQUENCE CHARACTERISTICS:
 ( A ) LENGTH: 13 amino acids
 ( B ) TYPE: amino acid
 ( C ) STRANDEDNESS: single
 ( D ) TOPOLOGY: linear ( x i ) SEQUENCE DESCRIPTION: SEQ ID NO: 7:

Arg Arg Leu Ile Glu Asp Asn Glu Tyr Thr Ala Arg Gly
1               5                   10

( 2 ) INFORMATION FOR SEQ ID NO: 8:

( i ) SEQUENCE CHARACTERISTICS:
  ( A ) LENGTH: 12 amino acids
  ( B ) TYPE: amino acid
  ( C ) STRANDEDNESS: single
  ( D ) TOPOLOGY: linear ( x i ) SEQUENCE DESCRIPTION: SEQ ID NO: 8:

Thr Leu Ala Tyr Pro Val Tyr Ala Gln Gln Arg Arg
1               5                   10

( 2 ) INFORMATION FOR SEQ ID NO: 9:

( i ) SEQUENCE CHARACTERISTICS:
  ( A ) LENGTH: 17 amino acids
  ( B ) TYPE: amino acid
  ( C ) STRANDEDNESS: single
  ( D ) TOPOLOGY: linear ( x i ) SEQUENCE DESCRIPTION: SEQ ID NO: 9:

Thr Leu Ala His Pro Val Arg Ala Pro Gly Pro Gly Pro Pro Ala Ala
1               5                   10                      15

Arg ( 2 ) INFORMATION FOR SEQ ID NO: 10:

( i ) SEQUENCE CHARACTERISTICS:
  ( A ) LENGTH: 4 amino acids
  ( B ) TYPE: amino acid
  ( C ) STRANDEDNESS: single
  ( D ) TOPOLOGY: linear ( x i ) SEQUENCE DESCRIPTION: SEQ ID NO: 10:

Tyr Xaa Xaa Met
1

( 2 ) INFORMATION FOR SEQ ID NO: 11:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( x i ) SEQUENCE DESCRIPTION: SEQ ID NO: 11:

Met Asp Trp Ile Phe His Thr
1               5

( 2 ) INFORMATION FOR SEQ ID NO: 12:

( i ) SEQUENCE CHARACTERISTICS:
  ( A ) LENGTH: 23 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 12:

AARATGGAYT GGATHTTYCA YAC 23

(2) INFORMATION FOR SEQ ID NO: 13:

(i) SEQUENCE CHARACTERISTICS:
        (A) LENGTH: 13 amino acids
        (B) TYPE: amino acid
        (C) STRANDEDNESS: single
        (D) TOPOLOGY: linear (xi) SEQUENCE DESCRIPTION: SEQ ID NO: 13:

Asp Asp Gly Gln Leu Phe His Ile Asp Phe Gly His Phe
1               5                   10

(2) INFORMATION FOR SEQ ID NO: 14:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 14:

GATGATGGCC ARCTGTTYCA YATWGAYTTT GGCCA 35

(2) INFORMATION FOR SEQ ID NO: 15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 15:

AATTCACACA CTGGCATGCC GAT 23

(2) INFORMATION FOR SEQ ID NO: 16:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 16:

GACTCGAGTC GACATCGATT TTTTTTTTT TTTTT 35

(2) INFORMATION FOR SEQ ID NO: 17:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 17:

TTTAAGCTTA GGCATTCTAA AGTCACTATC ATCCC 35

(2) INFORMATION FOR SEQ ID NO: 18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 18:

GACTCGAGTC GACATCGA 18

( 2 ) INFORMATION FOR SEQ ID NO: 19:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 19:

CAGGCCTGGC TTCCTGT                                    17

( 2 ) INFORMATION FOR SEQ ID NO: 20:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 20:

AACCAGGCTC AACTGTT                                    17

( 2 ) INFORMATION FOR SEQ ID NO: 21:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 21:

TGCTGTAAAT TCTAATGCTG                                 20

( 2 ) INFORMATION FOR SEQ ID NO: 22:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 22:

GTATTTCATG AAACAAATGA                                 20

( 2 ) INFORMATION FOR SEQ ID NO: 23:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( x i ) SEQUENCE DESCRIPTION: SEQ ID NO: 23:

Cys Lys Met Asp Trp Ile Phe His Thr Ile Lys Gln His Ala Leu Asn
    1                5                       10                    15

( 2 ) INFORMATION FOR SEQ ID NO: 24:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 24:

AAGGATCAGA ACAATGCCT                                  19

( 2 ) INFORMATION FOR SEQ ID NO: 25:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 25:

AGGCTTTCTT TAGCCATCA 19

( 2 ) INFORMATION FOR SEQ ID NO: 26:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO: 26:

Gly Asp Asp Leu Arg Gln Asp
1               5

( 2 ) INFORMATION FOR SEQ ID NO: 27:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 27:

GGNGAYGAYY TRCGNCARGA 20

( 2 ) INFORMATION FOR SEQ ID NO: 28:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO: 28:

Phe His Ile Asp Phe Gly His Phe
1               5

( 2 ) INFORMATION FOR SEQ ID NO: 29:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 29:

RAARTGCCRA ARTCDATRTG RAA 23

( 2 ) INFORMATION FOR SEQ ID NO: 30:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( x i ) SEQUENCE DESCRIPTION: SEQ ID NO: 30:

Glu Glu Glu Glu Glu Tyr Met Pro Met Xaa Xaa
1               5                          10

( 2 ) INFORMATION FOR SEQ ID NO: 31:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO: 31:

```
Asp  Asp  Asp  Asp  Asp  Val
 1                    5
```

( 2 ) INFORMATION FOR SEQ ID NO: 32:

( i ) SEQUENCE CHARACTERISTICS:
        ( A ) LENGTH: 3412 base pairs
        ( B ) TYPE: nucleic acid
        ( C ) STRANDEDNESS: single or double
        ( D ) TOPOLOGY: linear ( i x ) FEATURE:
        ( A ) NAME/KEY: CDS
        ( B ) LOCATION: 1..3204
        ( D ) OTHER INFORMATION: /standard_name= "CDS"

( x i ) SEQUENCE DESCRIPTION: SEQ ID NO: 32:

```
ATG  CCT  CCA  AGA  CCA  TCA  TCA  GGT  GAA  CTG  TGG  GGC  ATC  CAC  TTG  ATG         48
Met  Pro  Pro  Arg  Pro  Ser  Ser  Gly  Glu  Leu  Trp  Gly  Ile  His  Leu  Met
 1                    5                        10                       15

CCC  CCA  AGA  ATC  CTA  GTG  GAA  TGT  TTA  CTA  CCA  AAT  GGA  ATG  ATA  GTG         96
Pro  Pro  Arg  Ile  Leu  Val  Glu  Cys  Leu  Leu  Pro  Asn  Gly  Met  Ile  Val
               20                        25                       30

ACT  TTA  GAA  TGC  CTC  CGT  GAG  GCT  ACA  TTA  GTA  ACT  ATA  AAG  CAT  GAA        144
Thr  Leu  Glu  Cys  Leu  Arg  Glu  Ala  Thr  Leu  Val  Thr  Ile  Lys  His  Glu
          35                        40                       45

CTA  TTT  AAA  GAA  GCA  AGA  AAA  TAC  CCT  CTC  CAT  CAA  CTT  CTT  CAA  GAT        192
Leu  Phe  Lys  Glu  Ala  Arg  Lys  Tyr  Pro  Leu  His  Gln  Leu  Leu  Gln  Asp
     50                        55                       60

GAA  TCT  TCT  TAC  ATT  TTC  GTA  AGT  GTT  ACC  CAA  GAA  GCA  GAA  AGG  GAA        240
Glu  Ser  Ser  Tyr  Ile  Phe  Val  Ser  Val  Thr  Gln  Glu  Ala  Glu  Arg  Glu
65                       70                       75                        80

GAA  TTT  TTT  GAT  GAA  ACA  AGA  CGA  CTT  TGT  GAT  CTT  CGG  CTT  TTT  CAA        288
Glu  Phe  Phe  Asp  Glu  Thr  Arg  Arg  Leu  Cys  Asp  Leu  Arg  Leu  Phe  Gln
                         85                       90                        95

CCA  TTT  TTA  AAA  GTA  ATT  GAA  CCA  GTA  GGC  AAC  CGT  GAA  GAA  AAG  ATC        336
Pro  Phe  Leu  Lys  Val  Ile  Glu  Pro  Val  Gly  Asn  Arg  Glu  Glu  Lys  Ile
               100                       105                     110

CTC  AAT  CGA  GAA  ATT  GGT  TTT  GCT  ATC  GGC  ATG  CCA  GTG  TGC  GAA  TTT        384
Leu  Asn  Arg  Glu  Ile  Gly  Phe  Ala  Ile  Gly  Met  Pro  Val  Cys  Glu  Phe
          115                       120                      125

GAT  ATG  GTT  AAA  GAT  CCT  GAA  GTA  CAG  GAC  TTC  CGA  AGA  AAT  ATT  CTT        432
Asp  Met  Val  Lys  Asp  Pro  Glu  Val  Gln  Asp  Phe  Arg  Arg  Asn  Ile  Leu
     130                       135                      140

AAT  GTT  TGT  AAA  GAA  GCT  GTG  GAT  CTT  AGG  GAT  CTT  AAT  TCA  CCT  CAT        480
Asn  Val  Cys  Lys  Glu  Ala  Val  Asp  Leu  Arg  Asp  Leu  Asn  Ser  Pro  His
145                       150                      155                      160

AGT  AGA  GCA  ATG  TAT  GTC  TAT  CCG  CCA  CAT  GTA  GAA  TCT  TCA  CCA  GAG        528
Ser  Arg  Ala  Met  Tyr  Val  Tyr  Pro  Pro  His  Val  Glu  Ser  Ser  Pro  Glu
                    165                       170                     175

CTG  CCA  AAG  CAC  ATA  TAT  AAT  AAA  TTG  GAT  AGA  GGC  CAA  ATA  ATA  GTG        576
Leu  Pro  Lys  His  Ile  Tyr  Asn  Lys  Leu  Asp  Arg  Gly  Gln  Ile  Ile  Val
               180                       185                     190

GTG  ATT  TGG  GTA  ATA  GTT  TCT  CCA  AAT  AAT  GAC  AAG  CAG  AAG  TAT  ACT        624
```

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| Val   | Ile   | Trp   | Val   | Ile   | Val   | Ser   | Pro   | Asn   | Asn   | Asp   | Lys   | Gln   | Lys   | Tyr   | Thr   |      |
|       |       | 195   |       |       |       |       | 200   |       |       |       | 205   |       |       |       |       |      |
| CTG   | AAA   | ATC   | AAC   | CAT   | GAC   | TGT   | GTG   | CCA   | GAA   | CAA   | GTA   | ATT   | GCT   | GAA   | GCA   | 672  |
| Leu   | Lys   | Ile   | Asn   | His   | Asp   | Cys   | Val   | Pro   | Glu   | Gln   | Val   | Ile   | Ala   | Glu   | Ala   |      |
|       | 210   |       |       |       | 215   |       |       |       |       | 220   |       |       |       |       |       |      |
| ATC   | AGG   | AAA   | AAA   | ACT   | AGA   | AGT   | ATG   | TTG   | CTA   | TCA   | TCT   | GAA   | CAA   | TTA   | AAA   | 720  |
| Ile   | Arg   | Lys   | Lys   | Thr   | Arg   | Ser   | Met   | Leu   | Leu   | Ser   | Ser   | Glu   | Gln   | Leu   | Lys   |      |
| 225   |       |       |       | 230   |       |       |       |       | 235   |       |       |       |       |       | 240   |      |
| CTC   | TGT   | GTT   | TTA   | GAA   | TAT   | CAG   | GGC   | AAG   | TAC   | ATT   | TTA   | AAA   | GTG   | TGT   | GGA   | 768  |
| Leu   | Cys   | Val   | Leu   | Glu   | Tyr   | Gln   | Gly   | Lys   | Tyr   | Ile   | Leu   | Lys   | Val   | Cys   | Gly   |      |
|       |       |       |       | 245   |       |       |       |       | 250   |       |       |       |       | 255   |       |      |
| TGT   | GAT   | GAA   | TAC   | TTC   | CTA   | GAA   | AAA   | TAT   | CCT   | CTG   | AGT   | CAG   | TAT   | AAG   | TAT   | 816  |
| Cys   | Asp   | Glu   | Tyr   | Phe   | Leu   | Glu   | Lys   | Tyr   | Pro   | Leu   | Ser   | Gln   | Tyr   | Lys   | Tyr   |      |
|       |       |       | 260   |       |       |       | 265   |       |       |       |       |       | 270   |       |       |      |
| ATA   | AGA   | AGC   | TGT   | ATA   | ATG   | CTT   | GGG   | AGG   | ATG   | CCC   | AAT   | TTG   | AAG   | ATG   | ATG   | 864  |
| Ile   | Arg   | Ser   | Cys   | Ile   | Met   | Leu   | Gly   | Arg   | Met   | Pro   | Asn   | Leu   | Lys   | Met   | Met   |      |
|       |       | 275   |       |       |       |       | 280   |       |       |       | 285   |       |       |       |       |      |
| GCT   | AAA   | GAA   | AGC   | CTT   | TAT   | TCT   | CAA   | CTG   | CCA   | ATG   | GAC   | TGT   | TTT   | ACA   | ATG   | 912  |
| Ala   | Lys   | Glu   | Ser   | Leu   | Tyr   | Ser   | Gln   | Leu   | Pro   | Met   | Asp   | Cys   | Phe   | Thr   | Met   |      |
|       | 290   |       |       |       |       | 295   |       |       |       | 300   |       |       |       |       |       |      |
| CCA   | TCT   | TAT   | TCC   | AGA   | CGC   | ATT   | TCC   | ACA   | GCT   | ACA   | CCA   | TAT   | ATG   | AAT   | GGA   | 960  |
| Pro   | Ser   | Tyr   | Ser   | Arg   | Arg   | Ile   | Ser   | Thr   | Ala   | Thr   | Pro   | Tyr   | Met   | Asn   | Gly   |      |
| 305   |       |       |       |       | 310   |       |       |       |       | 315   |       |       |       |       | 320   |      |
| GAA   | ACA   | TCT   | ACA   | AAA   | TCC   | CTT   | TGG   | GTT   | ATA   | AAT   | AGA   | GCA   | CTC   | AGA   | ATA   | 1008 |
| Glu   | Thr   | Ser   | Thr   | Lys   | Ser   | Leu   | Trp   | Val   | Ile   | Asn   | Arg   | Ala   | Leu   | Arg   | Ile   |      |
|       |       |       |       | 325   |       |       |       |       | 330   |       |       |       |       | 335   |       |      |
| AAA   | ATT   | CTT   | TGT   | GCA   | ACC   | TAC   | GTG   | AAT   | CTA   | AAT   | ATT   | CGA   | GAC   | ATT   | GAC   | 1056 |
| Lys   | Ile   | Leu   | Cys   | Ala   | Thr   | Tyr   | Val   | Asn   | Leu   | Asn   | Ile   | Arg   | Asp   | Ile   | Asp   |      |
|       |       |       | 340   |       |       |       |       | 345   |       |       |       |       | 350   |       |       |      |
| AAG   | ATT   | TAT   | GTT   | CGA   | ACA   | GGT   | ATC   | TAC   | CAT   | GGA   | GGA   | GAA   | CCC   | TTA   | TGT   | 1104 |
| Lys   | Ile   | Tyr   | Val   | Arg   | Thr   | Gly   | Ile   | Tyr   | His   | Gly   | Gly   | Glu   | Pro   | Leu   | Cys   |      |
|       |       | 355   |       |       |       |       | 360   |       |       |       |       |       | 365   |       |       |      |
| GAC   | AAT   | GTG   | AAC   | ACT   | CAA   | AGA   | GTA   | CCT   | TGT   | TCC   | AAT   | CCC   | AGG   | TGG   | AAT   | 1152 |
| Asp   | Asn   | Val   | Asn   | Thr   | Gln   | Arg   | Val   | Pro   | Cys   | Ser   | Asn   | Pro   | Arg   | Trp   | Asn   |      |
|       | 370   |       |       |       |       | 375   |       |       |       |       | 380   |       |       |       |       |      |
| GAA   | TGG   | CTG   | AAT   | TAT   | GAT   | ATA   | TAC   | ATT   | CCT   | GAT   | CTT   | CCT   | CGT   | GCT   | GCT   | 1200 |
| Glu   | Trp   | Leu   | Asn   | Tyr   | Asp   | Ile   | Tyr   | Ile   | Pro   | Asp   | Leu   | Pro   | Arg   | Ala   | Ala   |      |
| 385   |       |       |       |       | 390   |       |       |       |       | 395   |       |       |       |       | 400   |      |
| CGA   | CTT   | TGC   | CTT   | TCC   | ATT   | TGC   | TCT   | GTT   | AAA   | GGC   | CGA   | AAG   | GGT   | GCT   | AAA   | 1248 |
| Arg   | Leu   | Cys   | Leu   | Ser   | Ile   | Cys   | Ser   | Val   | Lys   | Gly   | Arg   | Lys   | Gly   | Ala   | Lys   |      |
|       |       |       |       | 405   |       |       |       |       | 410   |       |       |       |       | 415   |       |      |
| GAG   | GAA   | CAC   | TGT   | CCA   | TTG   | GCA   | TGG   | GGA   | AAT   | ATA   | AAC   | TTG   | TTT   | GAT   | TAC   | 1296 |
| Glu   | Glu   | His   | Cys   | Pro   | Leu   | Ala   | Trp   | Gly   | Asn   | Ile   | Asn   | Leu   | Phe   | Asp   | Tyr   |      |
|       |       |       | 420   |       |       |       |       | 425   |       |       |       |       | 430   |       |       |      |
| ACA   | GAC   | ACT   | CTA   | GTA   | TCT   | GGA   | AAA   | ATG   | GCT   | TTG   | AAT   | CTT   | TGG   | CCA   | GTA   | 1344 |
| Thr   | Asp   | Thr   | Leu   | Val   | Ser   | Gly   | Lys   | Met   | Ala   | Leu   | Asn   | Leu   | Trp   | Pro   | Val   |      |
|       |       | 435   |       |       |       |       | 440   |       |       |       |       | 445   |       |       |       |      |
| CCT   | CAT   | GGA   | TTA   | GAA   | GAT   | TTG   | CTG   | AAC   | CCT   | ATT   | GGT   | GTT   | ACT   | GGA   | TCA   | 1392 |
| Pro   | His   | Gly   | Leu   | Glu   | Asp   | Leu   | Leu   | Asn   | Pro   | Ile   | Gly   | Val   | Thr   | Gly   | Ser   |      |
|       | 450   |       |       |       |       | 455   |       |       |       |       | 460   |       |       |       |       |      |
| AAT   | CCA   | AAT   | AAA   | GAA   | ACT   | CCA   | TGC   | TTA   | GAG   | TTG   | GAG   | TTT   | GAC   | TGG   | TTC   | 1440 |
| Asn   | Pro   | Asn   | Lys   | Glu   | Thr   | Pro   | Cys   | Leu   | Glu   | Leu   | Glu   | Phe   | Asp   | Trp   | Phe   |      |
| 465   |       |       |       |       | 470   |       |       |       |       | 475   |       |       |       |       | 480   |      |
| AGC   | AGT   | GTG   | GTA   | AAG   | TTC   | CCA   | GAT   | ATG   | TCA   | GTG   | ATT   | GAA   | GAG   | CAT   | GCC   | 1488 |
| Ser   | Ser   | Val   | Val   | Lys   | Phe   | Pro   | Asp   | Met   | Ser   | Val   | Ile   | Glu   | Glu   | His   | Ala   |      |
|       |       |       |       | 485   |       |       |       |       | 490   |       |       |       |       | 495   |       |      |
| AAT   | TGG   | TCT   | GTA   | TCC   | CGA   | GAA   | GCA   | GGA   | TTT   | AGC   | TAT   | TCC   | CAC   | GCA   | GGA   | 1536 |
| Asn   | Trp   | Ser   | Val   | Ser   | Arg   | Glu   | Ala   | Gly   | Phe   | Ser   | Tyr   | Ser   | His   | Ala   | Gly   |      |
|       |       |       | 500   |       |       |       |       | 505   |       |       |       |       | 510   |       |       |      |
| CTG   | AGT   | AAC   | AGA   | CTA   | GCT   | AGA   | GAC   | AAT   | GAA   | TTA   | AGG   | GAA   | AAT   | GAC   | AAA   | 1584 |

```
Leu Ser Asn Arg Leu Ala Arg Asp Asn Glu Leu Arg Glu Asn Asp Lys
        515                 520                 525

GAA CAG CTC AAA GCA ATT TCT ACA CGA GAT CCT CTC TCT GAA ATC ACT    1632
Glu Gln Leu Lys Ala Ile Ser Thr Arg Asp Pro Leu Ser Glu Ile Thr
530                 535                 540

GAG CAG GAG AAA GAT TTT CTA TGG AGT CAC AGA CAC TAT TGT GTA ACT    1680
Glu Gln Glu Lys Asp Phe Leu Trp Ser His Arg His Tyr Cys Val Thr
545                 550                 555                 560

ATC CCC GAA ATT CTA CCC AAA TTG CTT CTG TCT GTT AAA TGG AAT TCT    1728
Ile Pro Glu Ile Leu Pro Lys Leu Leu Leu Ser Val Lys Trp Asn Ser
                565                 570                 575

AGA GAT GAA GTA GCC CAG ATG TAT TGC TTG GTA AAA GAT TGG CCT CCA    1776
Arg Asp Glu Val Ala Gln Met Tyr Cys Leu Val Lys Asp Trp Pro Pro
580                 585                 590

ATC AAA CCT GAA CAG GCT ATG GAA CTT CTG GAC TGT AAT TAC CCA GAT    1824
Ile Lys Pro Glu Gln Ala Met Glu Leu Leu Asp Cys Asn Tyr Pro Asp
            595                 600                 605

CCT ATG GTT CGA GGT TTT GCT GTT CGG TGC TTG GAA AAA TAT TTA ACA    1872
Pro Met Val Arg Gly Phe Ala Val Arg Cys Leu Glu Lys Tyr Leu Thr
    610                 615                 620

GAT GAC AAA CTT TCT CAG TAT TTA ATT CAG CTA GTA CAG GTC CTA AAA    1920
Asp Asp Lys Leu Ser Gln Tyr Leu Ile Gln Leu Val Gln Val Leu Lys
625                 630                 635                 640

TAT GAA CAA TAT TTG GAT AAC TTG CTT GTG AGA TTT TTA CTG AAG AAA    1968
Tyr Glu Gln Tyr Leu Asp Asn Leu Leu Val Arg Phe Leu Leu Lys Lys
                645                 650                 655

GCA TTG ACT AAT CAA AGG ATT GGG CAC TTT TTC TTT TGG CAT TTA AAA    2016
Ala Leu Thr Asn Gln Arg Ile Gly His Phe Phe Phe Trp His Leu Lys
            660                 665                 670

TCT GAG ATG CAC AAT AAA ACA GTT AGC CAG AGG TTT GGC CTG CTT TTG    2064
Ser Glu Met His Asn Lys Thr Val Ser Gln Arg Phe Gly Leu Leu Leu
        675                 680                 685

GAG TCC TAT TGT CGT GCA TGT GGG ATG TAT TTG AAG CAC TTG AAT AGG    2112
Glu Ser Tyr Cys Arg Ala Cys Gly Met Tyr Leu Lys His Leu Asn Arg
    690                 695                 700

CAA GTC GAG GCA ATG GAA AAG CTC ATT AAC TTA ACT GAC ATT CTC AAA    2160
Gln Val Glu Ala Met Glu Lys Leu Ile Asn Leu Thr Asp Ile Leu Lys
705                 710                 715                 720

CAG GAG AGG AAG GAT GAA ACA CAA AAG GTA CAG ATG AAG TTT TTA GTT    2208
Gln Glu Arg Lys Asp Glu Thr Gln Lys Val Gln Met Lys Phe Leu Val
                725                 730                 735

GAG CAA ATG AGG CGA CCA GAT TTC ATG GAT GCC CTA CAG GGC TTG CTG    2256
Glu Gln Met Arg Arg Pro Asp Phe Met Asp Ala Leu Gln Gly Leu Leu
            740                 745                 750

TCT CCT CTA AAC CCT GCT CAT CAA CTA GGA AAC CTC AGG CTT AAA GAG    2304
Ser Pro Leu Asn Pro Ala His Gln Leu Gly Asn Leu Arg Leu Lys Glu
        755                 760                 765

TGT CGA ATT ATG TCT TCT GCA AAA AGG CCA CTG TGG TTG AAT TGG GAG    2352
Cys Arg Ile Met Ser Ser Ala Lys Arg Pro Leu Trp Leu Asn Trp Glu
    770                 775                 780

AAC CCA GAC ATC ATG TCA GAG TTA CTG TTT CAG AAC AAT GAG ATC ATC    2400
Asn Pro Asp Ile Met Ser Glu Leu Leu Phe Gln Asn Asn Glu Ile Ile
785                 790                 795                 800

TTT AAA AAT GGG GAT GAT TTA CGG CAA GAT ATG CTA ACA CTT CAA ATT    2448
Phe Lys Asn Gly Asp Asp Leu Arg Gln Asp Met Leu Thr Leu Gln Ile
                805                 810                 815

ATT CGT ATT ATG GAA AAT ATC TGG CAA AAT CAA GGT CTT GAT CTT CGA    2496
Ile Arg Ile Met Glu Asn Ile Trp Gln Asn Gln Gly Leu Asp Leu Arg
            820                 825                 830

ATG TTA CCT TAT GGT TGT CTG TCA ATC GGT GAC TGT GTG GGA CTT ATT    2544
```

|   |   |   |   |   |   |   |   |   |   |   |   |   |   |   |   |
|---|---|---|---|---|---|---|---|---|---|---|---|---|---|---|---|
| Met | Leu | Pro 835 | Tyr | Gly | Cys | Leu | Ser 840 | Ile | Gly | Asp | Cys 845 | Val | Gly | Leu | Ile |

| GAG | GTG | GTG | CGA | AAT | TCT | CAC | ACT | ATT | ATG | CAA | ATT | CAG | TGC | AAA | GGC | 2592 |
|---|---|---|---|---|---|---|---|---|---|---|---|---|---|---|---|---|
| Glu | Val | Val | Arg | Asn | Ser | His | Thr | Ile | Met | Gln | Ile | Gln | Cys | Lys | Gly | |
|  | 850 |  |  |  | 855 |  |  |  |  | 860 |  |  |  |  |  |  |

| GGC | TTG | AAA | GGT | GCA | CTG | CAG | TTC | AAC | AGC | CAC | ACA | CTA | CAT | CAG | TGG | 2640 |
|---|---|---|---|---|---|---|---|---|---|---|---|---|---|---|---|---|
| Gly | Leu | Lys | Gly | Ala | Leu | Gln | Phe | Asn | Ser | His | Thr | Leu | His | Gln | Trp | |
| 865 |  |  |  | 870 |  |  |  |  | 875 |  |  |  |  | 880 |  |  |

| CTC | AAA | GAC | AAG | AAC | AAA | GGA | GAA | ATA | TAT | GAT | GCA | GCC | ATT | GAC | CTG | 2688 |
|---|---|---|---|---|---|---|---|---|---|---|---|---|---|---|---|---|
| Leu | Lys | Asp | Lys | Asn | Lys | Gly | Glu | Ile | Tyr | Asp | Ala | Ala | Ile | Asp | Leu | |
|  |  |  |  | 885 |  |  |  |  | 890 |  |  |  | 895 |  |  |  |

| TTT | ACA | CGT | TCA | TGT | GCT | GGA | TAC | TGT | GTA | GCT | ACC | TTC | ATT | TTG | GGA | 2736 |
|---|---|---|---|---|---|---|---|---|---|---|---|---|---|---|---|---|
| Phe | Thr | Arg | Ser | Cys | Ala | Gly | Tyr | Cys | Val | Ala | Thr | Phe | Ile | Leu | Gly | |
|  |  |  | 900 |  |  |  |  | 905 |  |  |  |  | 910 |  |  |  |

| ATT | GGA | GAT | CGT | CAC | AAT | AGT | AAC | ATC | ATG | GTG | AAA | GAC | GAT | GGA | CAA | 2784 |
|---|---|---|---|---|---|---|---|---|---|---|---|---|---|---|---|---|
| Ile | Gly | Asp | Arg | His | Asn | Ser | Asn | Ile | Met | Val | Lys | Asp | Asp | Gly | Gln | |
|  |  |  | 915 |  |  |  |  | 920 |  |  |  |  | 925 |  |  |  |

| CTG | TTT | CAT | ATA | GAT | TTT | GGA | CAC | TTT | TTG | GAT | CAC | AAG | AAG | AAA | AAA | 2832 |
|---|---|---|---|---|---|---|---|---|---|---|---|---|---|---|---|---|
| Leu | Phe | His | Ile | Asp | Phe | Gly | His | Phe | Leu | Asp | His | Lys | Lys | Lys | Lys | |
|  | 930 |  |  |  |  | 935 |  |  |  |  | 940 |  |  |  |  |  |

| TTT | GGT | TAT | AAA | CGA | GAA | CGT | GTG | CCA | TTT | GTT | TTG | ACA | CAG | GAT | TTC | 2880 |
|---|---|---|---|---|---|---|---|---|---|---|---|---|---|---|---|---|
| Phe | Gly | Tyr | Lys | Arg | Glu | Arg | Val | Pro | Phe | Val | Leu | Thr | Gln | Asp | Phe | |
| 945 |  |  |  |  | 950 |  |  |  |  | 955 |  |  |  |  | 960 |  |

| TTA | ATA | GTG | ATT | AGT | AAA | GGA | GCC | CAA | GAA | TGC | ACA | AAG | ACA | AGA | GAA | 2928 |
|---|---|---|---|---|---|---|---|---|---|---|---|---|---|---|---|---|
| Leu | Ile | Val | Ile | Ser | Lys | Gly | Ala | Gln | Glu | Cys | Thr | Lys | Thr | Arg | Glu | |
|  |  |  |  | 965 |  |  |  |  | 970 |  |  |  |  | 975 |  |  |

| TTT | GAG | AGG | TTT | CAG | GAG | ATG | TGT | TAC | AAG | GCT | TAT | CTA | GCT | ATT | CGA | 2976 |
|---|---|---|---|---|---|---|---|---|---|---|---|---|---|---|---|---|
| Phe | Glu | Arg | Phe | Gln | Glu | Met | Cys | Tyr | Lys | Ala | Tyr | Leu | Ala | Ile | Arg | |
|  |  |  | 980 |  |  |  |  | 985 |  |  |  |  | 990 |  |  |  |

| CAG | CAT | GCC | AAT | CTC | TTC | ATA | AAT | CTT | TTC | TCA | ATG | ATG | CTT | GGC | TCT | 3024 |
|---|---|---|---|---|---|---|---|---|---|---|---|---|---|---|---|---|
| Gln | His | Ala | Asn | Leu | Phe | Ile | Asn | Leu | Phe | Ser | Met | Met | Leu | Gly | Ser | |
|  |  | 995 |  |  |  |  | 1000 |  |  |  |  | 1005 |  |  |  |  |

| GGA | ATG | CCA | GAA | CTA | CAA | TCT | TTT | GAT | GAC | ATT | GCA | TAC | ATT | CGA | AAG | 3072 |
|---|---|---|---|---|---|---|---|---|---|---|---|---|---|---|---|---|
| Gly | Met | Pro | Glu | Leu | Gln | Ser | Phe | Asp | Asp | Ile | Ala | Tyr | Ile | Arg | Lys | |
|  |  | 1010 |  |  |  |  | 1015 |  |  |  |  | 1020 |  |  |  |  |

| ACC | CTA | GCC | TTA | GAT | AAA | ACT | GAG | CAA | GAG | GCT | TTG | GAG | TAT | TTC | ATG | 3120 |
|---|---|---|---|---|---|---|---|---|---|---|---|---|---|---|---|---|
| Thr | Leu | Ala | Leu | Asp | Lys | Thr | Glu | Gln | Glu | Ala | Leu | Glu | Tyr | Phe | Met | |
| 1025 |  |  |  |  | 1030 |  |  |  |  | 1035 |  |  |  |  | 1040 |  |

| AAA | CAA | ATG | AAT | GAT | GCA | CAT | CAT | GGT | GGC | TGG | ACA | ACA | AAA | ATG | GAT | 3168 |
|---|---|---|---|---|---|---|---|---|---|---|---|---|---|---|---|---|
| Lys | Gln | Met | Asn | Asp | Ala | His | His | Gly | Gly | Trp | Thr | Thr | Lys | Met | Asp | |
|  |  |  |  | 1045 |  |  |  |  | 1050 |  |  |  |  | 1055 |  |  |

| TGG | ATC | TTC | CAC | ACA | ATT | AAA | CAG | CAT | GCA | TTG | AAC | TGAAAGATAA | 3214 |
|---|---|---|---|---|---|---|---|---|---|---|---|---|---|
| Trp | Ile | Phe | His | Thr | Ile | Lys | Gln | His | Ala | Leu | Asn | | |
|  |  |  | 1060 |  |  |  |  | 1065 |  |  |  | | |

| CTGAGAAAAT | GAAAGCTCAC | TCTGGACACT | ACACTGCACT | GTTAATAACT | CTCAGCAGGC | 3274 |
|---|---|---|---|---|---|---|
| AAAGACCGAT | TGCATAGGAA | TTGCACAATC | CATGAACAGC | ATTAGATTTA | CAGCAAGAAC | 3334 |
| AGAAATAAAA | TACTATATAA | TTTAAATAAT | GTAAACGCAA | ACAGGGTTTG | ATAGCACTTA | 3394 |
| AACTAGTTCA | TTTCAAAA | | | | | 3412 |

( 2 ) INFORMATION FOR SEQ ID NO: 33:

( i ) SEQUENCE CHARACTERISTICS:
        ( A ) LENGTH: 868 amino acids residues
        ( B ) TYPE: amino acid
        ( C ) STRANDEDNESS: single
        ( D ) TOPOLOGY: linear ( x i ) SEQUENCE DESCRIPTION: SEQ ID NO: 33:

| Asn | Ile | Thr | Phe | Cys | Val | Ser | Gln | Asp | Leu | Asp | Val | Pro | Leu | Lys | Val |
|---|---|---|---|---|---|---|---|---|---|---|---|---|---|---|---|
| 1 |  |  |  | 5 |  |  |  |  | 10 |  |  |  |  | 15 |  |

```
Lys Ile Lys Ser Leu Glu Gly His Lys Pro Leu Leu Lys Pro Ser Gln
             20                  25                  30

Lys Ile Leu Asn Pro Glu Leu Met Leu Ile Gly Ser Asn Val Phe Pro
             35                  40                  45

Ser Ser Asp Leu Ile Val Ser Leu Gln Val Phe Asp Lys Glu Arg Asn
     50                  55                  60

Arg Asn Leu Thr Leu Pro Ile Tyr Thr Pro Tyr Ile Pro Phe Arg Asn
65                       70                  75                  80

Ser Arg Thr Trp Asp Tyr Trp Leu Thr Leu Pro Ile Arg Ile Lys Gln
                 85                  90                  95

Leu Thr Phe Ser Ser His Leu Arg Ile Ile Leu Trp Glu Tyr Asn Gly
             100                 105                 110

Ser Lys Gln Ile Pro Phe Phe Asn Leu Glu Thr Ser Ile Phe Asn Leu
         115                 120                 125

Lys Asp Cys Thr Leu Lys Arg Gly Phe Glu Ser Leu Lys Phe Arg Tyr
     130                 135                 140

Asp Val Ile Asp His Cys Glu Val Val Thr Asp Asn Lys Asp Gln Glu
145                 150                 155                 160

Asn Leu Asn Lys Tyr Phe Gln Gly Glu Phe Thr Arg Leu Pro Trp Leu
                 165                 170                 175

Asp Glu Ile Thr Ile Ser Lys Leu Arg Lys Gln Arg Glu Asn Arg Thr
             180                 185                 190

Trp Pro Gln Gly Thr Phe Val Leu Asn Leu Glu Phe Pro Met Leu Glu
         195                 200                 205

Leu Pro Val Val Phe Ile Glu Arg Glu Ile Met Asn Thr Gln Met Asn
     210                 215                 220

Ile Pro Thr Leu Lys Asn Asn Pro Gly Leu Ser Thr Asp Leu Arg Glu
225                 230                 235                 240

Pro Asn Arg Asn Asp Pro Gln Ile Lys Ile Ser Leu Gly Asp Lys Tyr
                 245                 250                 255

His Ser Thr Leu Lys Phe Tyr Asp Pro Asp Gln Pro Asn Asn Asp Pro
             260                 265                 270

Ile Glu Glu Lys Tyr Arg Arg Leu Glu Arg Ala Ser Lys Asn Ala Asn
         275                 280                 285

Leu Asp Lys Gln Val Lys Pro Asp Ile Lys Lys Arg Asp Tyr Leu Asn
     290                 295                 300

Lys Ile Ile Asn Tyr Pro Pro Gly Thr Lys Leu Thr Ala His Glu Lys
305                 310                 315                 320

Gly Ser Ile Trp Lys Tyr Arg Tyr Tyr Leu Met Asn Asn Lys Lys Ala
                 325                 330                 335

Leu Thr Lys Leu Leu Gln Ser Thr Asn Leu Arg Glu Glu Ser Glu Arg
         340                 345                 350

Val Glu Val Leu Glu Leu Met Asp Ser Trp Ala Glu Ile Asp Ile Asp
     355                 360                 365

Asp Ala Leu Glu Leu Leu Gly Ser Thr Phe Lys Asn Leu Ser Val Arg
     370                 375                 380

Ser Tyr Ala Val Asn Arg Leu Lys Lys Ala Ser Asp Lys Glu Leu Glu
385                 390                 395                 400

Leu Tyr Leu Leu Gln Leu Val Glu Ala Val Cys Phe Glu Asn Leu Ser
                 405                 410                 415

Thr Phe Ser Asp Lys Ser Asn Ser Glu Phe Thr Ile Val Asp Ala Val
             420                 425                 430

Ser Ser Gln Lys Leu Ser Gly Asp Ser Met Leu Leu Ser Thr Ser His
```

-continued

```
                                435                             440                             445
        Ala   Asn   Gln   Lys   Leu   Leu   Lys   Ser   Ile   Ser   Ser   Ser   Glu   Ser   Thr   Ser
              450                             455                             460
        Gly   Thr   Glu   Ser   Leu   Pro   Ile   Val   Ile   Ser   Pro   Leu   Ala   Glu   Phe   Leu
        465                             470                             475                             480
        Ile   Arg   Arg   Ala   Leu   Val   Asn   Pro   Arg   Leu   Gly   Ser   Phe   Phe   Tyr   Trp
                                  485                             490                             495
        Tyr   Leu   Lys   Ser   Glu   Ser   Glu   Asp   Lys   Pro   Tyr   Leu   Asp   Gln   Ile   Leu
                          500                             505                             510
        Ser   Ser   Phe   Trp   Ser   Arg   Leu   Asp   Lys   Lys   Ser   Arg   Asn   Ile   Leu   Asn
                    515                             520                             525
        Asp   Gln   Val   Arg   Leu   Ile   Asn   Val   Leu   Arg   Glu   Cys   Cys   Glu   Thr   Ile
              530                             535                             540
        Lys   Arg   Leu   Lys   Asp   Thr   Thr   Ala   Lys   Lys   Met   Glu   Leu   Leu   Val   His
        545                             550                             555                             560
        Leu   Leu   Glu   Thr   Lys   Val   Arg   Pro   Leu   Val   Lys   Val   Arg   Pro   Ile   Ala
                                  565                             570                             575
        Leu   Pro   Leu   Asp   Pro   Asp   Val   Leu   Ile   Cys   Asp   Val   Cys   Pro   Glu   Thr
                            580                             585                             590
        Ser   Lys   Val   Phe   Lys   Ser   Ser   Leu   Ser   Pro   Leu   Lys   Ile   Thr   Phe   Lys
                    595                             600                             605
        Thr   Thr   Leu   Asn   Gln   Pro   Tyr   His   Leu   Met   Phe   Lys   Val   Gly   Asp   Asp
              610                             615                             620
        Leu   Arg   Gln   Asp   Gln   Leu   Val   Val   Gln   Ile   Ile   Ser   Leu   Met   Asn   Glu
        625                             630                             635                             640
        Leu   Leu   Lys   Asn   Glu   Asn   Val   Asp   Leu   Lys   Leu   Thr   Pro   Tyr   Lys   Ile
                                  645                             650                             655
        Leu   Ala   Thr   Gly   Pro   Gln   Glu   Gly   Ala   Ile   Glu   Phe   Ile   Pro   Asn   Asp
                            660                             665                             670
        Thr   Leu   Ala   Ser   Ile   Leu   Ser   Lys   Tyr   His   Gly   Ile   Leu   Gly   Tyr   Leu
                    675                             680                             685
        Lys   Leu   His   Tyr   Pro   Asp   Glu   Asn   Ala   Thr   Leu   Gly   Val   Gln   Gly   Trp
              690                             695                             700
        Val   Leu   Asp   Asn   Phe   Val   Lys   Ser   Cys   Ala   Gly   Tyr   Cys   Val   Ile   Thr
        705                             710                             715                             720
        Tyr   Ile   Leu   Gly   Val   Gly   Asp   Arg   His   Leu   Asp   Asn   Leu   Leu   Val   Thr
                                  725                             730                             735
        Pro   Asp   Gly   His   Phe   Phe   His   Ala   Asp   Phe   Gly   Tyr   Ile   Leu   Gly   Gln
                            740                             745                             750
        Asp   Pro   Lys   Pro   Phe   Pro   Pro   Leu   Met   Lys   Leu   Pro   Pro   Gln   Ile   Ile
                    755                             760                             765
        Glu   Ala   Phe   Gly   Gly   Ala   Glu   Ser   Ser   Asn   Tyr   Asp   Lys   Phe   Arg   Ser
              770                             775                             780
        Tyr   Cys   Phe   Val   Ala   Tyr   Ser   Ile   Leu   Arg   Arg   Asn   Ala   Gly   Leu   Ile
        785                             790                             795                             800
        Leu   Asn   Leu   Phe   Glu   Leu   Met   Lys   Thr   Ser   Asn   Ile   Pro   Asp   Ile   Arg
                                  805                             810                             815
        Ile   Asp   Pro   Asn   Gly   Ala   Ile   Leu   Arg   Val   Arg   Glu   Arg   Phe   Asn   Leu
                            820                             825                             830
        Asn   Met   Ser   Glu   Glu   Asp   Ala   Thr   Val   His   Phe   Gln   Asn   Leu   Ile   Asn
                    835                             840                             845
        Asp   Ser   Val   Asn   Ala   Leu   Leu   Pro   Ile   Val   Ile   Asp   His   Leu   His   Asn
              850                             855                             860
```

Leu Ala Gln Tyr
865

(2) INFORMATION FOR SEQ ID NO: 34:

(i) SEQUENCE CHARACTERISTICS:
        (A) LENGTH: 3240 base pairs
        (B) TYPE: nucleic acid
        (C) STRANDEDNESS: single
        (D) TOPOLOGY: linear (xi) SEQUENCE DESCRIPTION: SEQ ID NO: 34:

```
ATGCCTCCAA GACCATCATC AGGTGAACTG TGGGGCATCC ACTTGATGCC CCCAAGAATC      60
CTAGTGGAAT GTTTACTACC AAATGGAATG ATAGTGACTT TAGAATGCCT CCGTGAGGCT     120
ACATTAGTAA CTATAAAGCA TGAACTATTT AAAGAAGCAA GAAAATACCC TCTCCATCAA     180
CTTCTTCAAG ATGAATCTTC TTACATTTTC GTAAGTGTTA CCCAAGAAGC AGAAAGGGAA     240
GAATTTTTTG ATGAAACAAG ACGACTTTGT GATCTTCGGC TTTTTCAACC ATTTTTAAAA     300
GTAATTGAAC CAGTAGGCAA CCGTGAAGAA AAGATCCTCA ATCGAGAAAT TGGTTTTGCT     360
ATCGGCATGC CAGTGTGCGA ATTTGATATG GTTAAAGATC CTGAAGTACA GGACTTCCGA     420
AGAAATATTC TTAATGTTTG TAAAGAAGCT GTGGATCTTA GGGATCTTAA TTCACCTCAT     480
AGTAGAGCAA TGTATGTCTA TCCGCCACAT GTAGAATCTT CACCAGAGCT GCCAAAGCAC     540
ATATATAATA AATTGGATAG AGGCCAAATA ATAGTGGTGA TTTGGGTAAT AGTTTCTCCA     600
AATAATGACA AGCAGAAGTA TACTCTGAAA ATCAACCATG ACTGTGTGCC AGAACAAGTA     660
ATTGCTGAAG CAATCAGGAA AAAAACTAGA AGTATGTTGC TATCATCTGA ACAATTAAAA     720
CTCTGTGTTT TAGAATATCA GGGCAAGTAC ATTTTAAAAG TGTGTGGATG TGATGAATAC     780
TTCCTAGAAA AATATCCTCT GAGTCAGTAT AAGTATATAA GAAGCTGTAT AATGCTTGGG     840
AGGATGCCCA ATTTGAAGAT GATGGCTAAA GAAAGCCTTT ATTCTCAACT GCCAATGGAC     900
TGTTTTACAA TGCCATCTTA TTCCAGACGC ATTTCCACAG CTACACCATA TATGAATGGA     960
GAAACATCTA CAAAATCCCT TTGGGTTATA AATAGAGCAC TCAGAATAAA AATTCTTTGT    1020
GCAACCTATG TGAATGTAAA TATTCGAGAC ATTGACAAGA TTTATGTTCG AACAGGTATC    1080
TACCATGGAG GAGAACCCTT ATGTGACAAT GTGAACACTC AAAGAGTACC TTGTTCCAAT    1140
CCCAGGTGGA ATGAATGGCT GAATTATGAT ATATACATTC CTGATCTTCC TCGTGCTGCT    1200
CGACTTTGCC TTTCCATTTG CTCTGTTAAA GGCCGAAAGG GTGCTAAAGA GGAACACTGT    1260
CCATTGGCAT GGGGAAATAT AAACTTGTTT GATTACACAG ACACTCTAGT ATCTGGAAAA    1320
ATGGCTTTGA ATCTTTGGCC AGTACCTCAT GGATTAGAAG ATTTGCTGAA CCCTATTGGT    1380
GTTACTGGAT CAAATCCAAA TAAAGAAACT CCATGCTTAG AGTTGGAGTT TGACTGGTTC    1440
AGCAGTGTGG TAAAGTTCCC AGATATGTCA GTGATTGAAG AGCATGCCAA TTGGTCTGTA    1500
TCCCGAGAAG CAGGATTTAG CTATTCCCAC GCAGGACTGA GTAACAGACT AGCTAGAGAC    1560
AATGAATTAA GGGAAAATGA CAAAGAACAG CTCAAAGCAA TTTCTACACG AGATCCTCTC    1620
TCTGAAATCA CTGAGCAGGA GAAAGATTTT CTATGGAGTC ACAGACACTA TTGTGTAACT    1680
ATCCCCGAAA TTCTACCCAA ATTGCTTCTG TCTGTTAAAT GGAATTCTAG AGATGAAGTA    1740
GCCCAGATGT ATTGCTTGGT AAAAGATTGG CCTCCAATCA AACCTGAACA GGCTATGGAA    1800
CTTCTGGACT GTAATTACCC AGATCCTATG GTTCGAGGTT TGCTGTTCG GTGCTTGGAA    1860
AAATATTTAA CAGATGACAA ACTTTCTCAG TATTTAATTC AGCTAGTACA GGTCCTAAAA    1920
TATGAACAAT ATTTGGATAA CTTGCTTGTG AGATTTTTAC TGAAGAAAGC ATTGACTAAT    1980
```

| | | | | | | |
|---|---|---|---|---|---|---|
| CAAAGGATTG | GGCACTTTTT | CTTTTGGCAT | TTAAAATCTG | AGATGCACAA | TAAAACAGTT | 2040 |
| AGCCAGAGGT | TTGGCCTGCT | TTTGGAGTCC | TATTGTCGTG | CATGTGGGAT | GTATTTGAAG | 2100 |
| CACCTGAATA | GGCAAGTCGA | GGCAATGGAA | AAGCTCATTA | ACTTAACTGA | CATTCTCAAA | 2160 |
| CAGGAGAGGA | AGGATGAAAC | ACAAAAGGTA | CAGATGAAGT | TTTTAGTTGA | GCAAATGAGG | 2220 |
| CGACCAGATT | TCATGGATGC | CCTACAGGGC | TTGCTGTCTC | CTCTAAACCC | TGCTCATCAA | 2280 |
| CTAGGAAACC | TCAGGCTTAA | AGAGTGTCGA | ATTATGTCTT | CTGCAAAAAG | GCCACTGTGG | 2340 |
| TTGAATTGGG | AGAACCCAGA | CATCATGTCA | GAGTTACTGT | TCAGAACAA | TGAGATCATC | 2400 |
| TTTAAAAATG | GGGATGATTT | ACGGCAAGAT | ATGCTAACAC | TTCAAATTAT | TCGTATTATG | 2460 |
| GAAAATATCT | GGCAAAATCA | AGGTCTTGAT | CTTCGAATGT | TACCTTATGG | TTGTCTGTCA | 2520 |
| ATCGGTGACT | GTGTGGGACT | TATTGAGGTG | GTGCGAAATT | CTCACACTAT | TATGCAAATT | 2580 |
| CAGTGCAAAG | GCGGCTTGAA | AGGTGCACTG | CAGTTCAACA | GCCACACACT | ACATCAGTGG | 2640 |
| CTCAAAGACA | AGAACAAAGG | AGAAATATAT | GATGCAGCCA | TTGACCTGTT | TACACGTTCA | 2700 |
| TGTGCTGGAT | ACTGTGTAGC | TACCTTCATT | TTGGGAATTG | GAGATCGTCA | CAATAGTAAC | 2760 |
| ATCATGGTGA | AAGACGATGG | ACAACTGTTT | CATATAGATT | TTGGACACTT | TTTGGATCAC | 2820 |
| AAGAAGAAAA | AATTTGGTTA | TAAACGAGAA | CGTGTGCCAT | TTGTTTTGAC | ACAGGATTTC | 2880 |
| TTAATAGTGA | TTAGTAAAGG | AGCCCAAGAA | TGCACAAGA | CAAGAGAATT | TGAGAGGTTT | 2940 |
| CAGGAGATGT | GTTACAAGGC | TTATCTAGCT | ATTCGACAGC | ATGCCAATCT | CTTCATAAAT | 3000 |
| CTTTTCTCAA | TGATGCTTGG | CTCTGGAATG | CCAGAACTAC | AATCTTTTGA | TGACATTGCA | 3060 |
| TACATTCGAA | AGACCCTAGC | CTTAGATAAA | ACTGAGCAAG | AGGCTTTGGA | GTATTTCATG | 3120 |
| AAACAAATGA | ATGATGCACA | TCATGGTGGC | TGGACAACAA | AAATGGATTG | GATCTTCCAC | 3180 |
| ACAATTAAAC | AGCATGCATT | GAACTGAAAG | ATAACTGAGA | AAATGAAAGC | TCACTCTGGA | 3240 |

( 2 ) INFORMATION FOR SEQ ID NO: 35:

( i ) SEQUENCE CHARACTERISTICS:
    ( A ) LENGTH: 3207 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 35:

| | | | | | | |
|---|---|---|---|---|---|---|
| ATGCCTCCAA | GACCATCATC | AGGTGAACTG | TGGGGCATCC | ACTTGATGCC | CCCAAGAATC | 60 |
| CTAGTAGAAT | GTTTACTACC | AAATGGGATG | ATAGTGACTT | TAGAATGCCT | CCGTGAGGCT | 120 |
| ACGTTAATAA | CGATAAAGCA | TGAACTATTT | AAAGAAGCAA | GAAAATACCC | TCTCCATCAA | 180 |
| CTTCTTCAAG | ATGAATCTTC | TTACATTTTC | GTAAGTGTTA | CCCAAGAAGC | AGAAAGGGAA | 240 |
| GAATTTTTTG | ATGAAACAAG | ACGACTTTGT | GACCTTCGGC | TTTTTCAACC | CTTTTTAAAA | 300 |
| GTAATTGAAC | CAGTAGGCAA | CCGTGAAGAA | AAGATCCTCA | ATCGAGAAAT | TGGTTTTGCT | 360 |
| ATCGGCATGC | CAGTGTGTGA | ATTCGATATG | GTTAAAGATC | CAGAAGTACA | GGACTTCCGA | 420 |
| AGAAATATTC | TCAATGTTTG | TAAAGAAGCT | GTGGATCTTA | GGGATCTTAA | TTCACCTCAT | 480 |
| AGTAGAGCAA | TGTATGTTTA | TCCTCCAAAT | GTAGAATCTT | CACCAGAACT | GCCAAAGCAC | 540 |
| ATATATAATA | AATTGGATAA | AGGGCAAATA | ATAGTGGTGA | TTTGGGTAAT | AGTTTCTCCA | 600 |
| AATAATGACA | AACAGAAGTA | TACTCTGAAA | ATCAACCATG | ACTGTGTGCC | AGAACAAGTA | 660 |
| ATTGCTGAAG | CAATCAGGAA | AAAAACTCGA | AGTATGTTGC | TATCATCTGA | ACAACTAAAA | 720 |
| CTCTGTGTTT | TAGAATATCA | GGGCAAGTAT | ATTTTAAAAG | TGTGTGGATG | TGATGAATAC | 780 |
| TTCCTAGAAA | AATATCCTCT | GAGTCAGTAT | AAGTATATAA | GAAGCTGTAT | AATGCTTGGG | 840 |

| | | | | | | |
|---|---|---|---|---|---|---|
| AGGATGCCCA | ATTTGATGCT | GATGGCTAAA | GAAAGCCTCT | ATTCTCAACT | GCCAATGGAC | 900 |
| TGTTTTACAA | TGCCATCATA | TTCCAGACGC | ATCTCCACAG | CTACGCCATA | TATGAATGGA | 960 |
| GAAACATCTA | CAAAATCCCT | TGGGTTATA | AATAGTGCAC | TCAGAATAAA | AATTCTTTGT | 1020 |
| GCAACCTATG | TGAATGTAAA | TATTCGAGAC | ATTGACAAGA | TTTATGTTCG | AACAGGTATC | 1080 |
| TACCATGGAG | GAGAACCCTT | ATGTGATAAT | GTGAACACTC | AAAGAGTACC | TTGTTCCAAT | 1140 |
| CCCAGGTGGA | ATGAATGGCT | GAATTACGAT | ATATACATTC | CTGATCTTCC | TCGTGCTGCT | 1200 |
| CGACTTTGCC | TTTCCATTTG | TTCTGTTAAA | GGCCGAAAGG | GTGCTAAAGA | GGAACACTGT | 1260 |
| CCATTGGCCT | GGGGAAATAT | AAACTTGTTT | GATTACACAG | ATACTCTAGT | ATCTGGAAAA | 1320 |
| ATGGCTTTGA | ATCTTTGGCC | AGTACCTCAT | GGACTAGAAG | ATTTGCTGAA | CCCTATTGGT | 1380 |
| GTTACTGGAT | CAAATCCAAA | TAAAGAAACT | CCATGTTTAG | AGTTGGAGTT | TGACTGGTTC | 1440 |
| AGCAGTGTGG | TAAAGTTTCC | AGATATGTCA | GTGATTGAAG | AGCATGCCAA | TTGGTCTGTA | 1500 |
| TCCCGTGAAG | CAGGATTTAG | TTATTCCCAT | GCAGGACTGA | GTAACAGACT | AGCTAGAGAC | 1560 |
| AATGAATTAA | GAGAAAATGA | TAAAGAACAG | CTCCGAGCAA | TTTGTACACG | AGATCCTCTA | 1620 |
| TCTGAAATCA | CTGAGCAAGA | GAAAGATTTT | CTGTGGAGCC | ACAGACACTA | TTGTGTAACT | 1680 |
| ATCCCCGAAA | TTCTACCCAA | ATTGCTTCTG | TCTGTTAAAT | GGAACTCTAG | AGATGAAGTA | 1740 |
| GCTCAGATGT | ACTGCTTGGT | AAAAGATTGG | CCTCCAATCA | AGCCTGAACA | GGCTATGGAG | 1800 |
| CTTCTGGACT | GCAATTACCC | AGATCCTATG | GTTCGAGGTT | TTGCTGTTCG | GTGCTTAGAA | 1860 |
| AAATATTTAA | CAGATGACAA | ACTTTCTCAG | TACCTAATTC | AGCTAGTACA | GGTACTAAAA | 1920 |
| TATGAACAGT | ATTTGGATAA | CCTGCTTGTG | AGATTTTTAC | TCAAAAAGC | GTTAACTAAT | 1980 |
| CAAAGGATCG | GTCACTTTTT | CTTTTGGCAT | TTAAAATCTG | AGATGCACAA | TAAAACAGTT | 2040 |
| AGTCAGAGGT | TTGGCCTGCT | TTTGGAGTCC | TATTGCCGTG | CATGTGGGAT | GTATCTGAAG | 2100 |
| CACCTTAATA | GGCAAGTTGA | GGCTATGGAA | AAGCTCATTA | ACTTGACTGA | CATTCTCAAA | 2160 |
| CAAGAGAAGA | AGGATGAAAC | ACAAAAGGTA | CAGATGAAGT | TTTTAGTTGA | GCAAATGCGG | 2220 |
| CGACCAGATT | TCATGGATGC | TCTCCAGGGC | TTTCTGTCTC | CTCTAAACCC | TGCTCATCAG | 2280 |
| CTGGGAAATC | TCAGGCTTGA | AGAGTGTCGA | ATTATGTCTT | CTGCAAAAAG | GCCACTGTGG | 2340 |
| TTGAATTGGG | AGAACCCAGA | CATCATGTCA | GAATTACTCT | TTCAGAACAA | TGAGATCATC | 2400 |
| TTTAAAAATG | GGGATGATTT | ACGGCAAGAT | ATGCTAACCC | TTCAGATTAT | TCGCATTATG | 2460 |
| GAAAATATCT | GGCAAAATCA | AGGTCTTGAT | CTTCGAATGT | TACCTTATGG | ATGTCTGTCA | 2520 |
| ATCGGTGACT | GTGTGGGACT | TATCGAGGTG | GTGAGAAATT | CTCACACTAT | AATGCAGATT | 2580 |
| CAGTGTAAAG | GAGGCCTGAA | AGGTGCACTG | CAGTTTAACA | GCCACACACT | CCATCAGTGG | 2640 |
| CTCAAAGACA | AGAACAAGGG | GGAAATATAT | GATGCGGCCA | TCGATTTGTT | TACACGATCA | 2700 |
| TGTGCTGGAT | ATTGTGTTGC | CACCTTCATT | TTGGGAATTG | GAGATCGTCA | CAATAGTAAT | 2760 |
| ATCATGGTTA | AAGATGATGG | ACAACTGTTT | CATATAGATT | TTGGACACTT | TTTGGATCAC | 2820 |
| AAGAAGAAAA | AATTTGGTTA | TAAACGAGAG | CGCGTGCCGT | TTGTTTTGAC | ACAAGATTTC | 2880 |
| TTAATAGTGA | TTAGTAAAGG | AGCCCAAGAA | TGCACAAAGA | CAAGAGAATT | TGAGAGGTTT | 2940 |
| CAGGAGATGT | GTTACAAGGC | TTATCTAGCT | ATTCGGCAGC | ATGCCAATCT | CTTCATAAAT | 3000 |
| CTTTTCTCAA | TGATGCTTGG | CTCTGGAATG | CCAGAACTGC | AATCTTTTGA | TGATATTGCA | 3060 |
| TACATTCGAA | AGACCCTAGC | TTTAGATAAA | ACTGAGCAAG | AGGCTTTGGA | GTATTTCATG | 3120 |
| AAACAAATGA | ATGATGCACA | CCATGGTGGC | TGGACAACAA | AAATGGATTG | GATCTTCCAC | 3180 |
| ACAATTAAGC | AGCATGCTTT | GAACTGA | | | | 3207 |

( 2 ) INFORMATION FOR SEQ ID NO: 36:

( i ) SEQUENCE CHARACTERISTICS:
        ( A ) LENGTH: 1080 amino acids
        ( B ) TYPE: amino acid
        ( C ) STRANDEDNESS: single
        ( D ) TOPOLOGY: linear ( x i ) SEQUENCE DESCRIPTION: SEQ ID NO: 36:

```
Met Pro Pro Arg Pro Ser Ser Gly Glu Leu Trp Gly Ile His Leu Met
 1               5                  10                  15
Pro Pro Arg Ile Leu Val Glu Cys Leu Leu Pro Asn Gly Met Ile Val
            20                  25                  30
Thr Leu Glu Cys Leu Arg Glu Ala Thr Leu Val Thr Ile Lys His Glu
        35                  40                  45
Leu Phe Lys Glu Ala Arg Lys Tyr Pro Leu His Gln Leu Leu Gln Asp
    50                  55                  60
Glu Ser Ser Tyr Ile Phe Val Ser Val Thr Gln Glu Ala Glu Arg Glu
65                  70                  75                  80
Glu Phe Phe Asp Glu Thr Arg Arg Leu Cys Asp Leu Arg Leu Phe Gln
                85                  90                  95
Pro Phe Leu Lys Val Ile Glu Pro Val Gly Asn Arg Glu Glu Lys Ile
            100                 105                 110
Leu Asn Arg Glu Ile Gly Phe Ala Ile Gly Met Pro Val Cys Glu Phe
        115                 120                 125
Asp Met Val Lys Asp Pro Glu Val Gln Asp Phe Arg Arg Asn Ile Leu
    130                 135                 140
Asn Val Cys Lys Glu Ala Val Asp Leu Arg Asp Leu Asn Ser Pro His
145                 150                 155                 160
Ser Arg Ala Met Tyr Val Tyr Pro Pro His Val Glu Ser Ser Pro Glu
                165                 170                 175
Leu Pro Lys His Ile Tyr Asn Lys Leu Asp Arg Gly Gln Ile Ile Val
            180                 185                 190
Val Ile Trp Val Ile Val Ser Pro Asn Asn Asp Lys Gln Lys Tyr Thr
        195                 200                 205
Leu Lys Ile Asn His Asp Cys Val Pro Glu Gln Val Ile Ala Glu Ala
    210                 215                 220
Ile Arg Lys Lys Thr Arg Ser Met Leu Leu Ser Ser Glu Gln Leu Lys
225                 230                 235                 240
Leu Cys Val Leu Glu Tyr Gln Gly Lys Tyr Ile Leu Lys Val Cys Gly
                245                 250                 255
Cys Asp Glu Tyr Phe Leu Glu Lys Tyr Pro Leu Ser Gln Tyr Lys Tyr
            260                 265                 270
Ile Arg Ser Cys Ile Met Leu Gly Arg Met Pro Asn Leu Lys Met Met
        275                 280                 285
Ala Lys Glu Ser Leu Tyr Ser Gln Leu Pro Met Asp Cys Phe Thr Met
    290                 295                 300
Pro Ser Tyr Ser Arg Arg Ile Ser Thr Ala Thr Pro Tyr Met Asn Gly
305                 310                 315                 320
Glu Thr Ser Thr Lys Ser Leu Trp Val Ile Asn Arg Ala Leu Arg Ile
                325                 330                 335
Lys Ile Leu Cys Ala Thr Tyr Val Asn Leu Asn Ile Arg Asp Ile Asp
            340                 345                 350
Lys Ile Tyr Val Arg Thr Gly Ile Tyr His Gly Gly Glu Pro Leu Cys
        355                 360                 365
```

```
Asp  Asn  Val  Asn  Thr  Gln  Arg  Val  Pro  Cys  Ser  Asn  Pro  Arg  Trp  Asn
     370                      375                 380

Glu  Trp  Leu  Asn  Tyr  Asp  Ile  Tyr  Ile  Pro  Asp  Leu  Pro  Arg  Ala  Ala
385                      390                      395                      400

Arg  Leu  Cys  Leu  Ser  Ile  Cys  Ser  Val  Lys  Gly  Arg  Lys  Gly  Ala  Lys
                    405                      410                      415

Glu  Glu  His  Cys  Pro  Leu  Ala  Trp  Gly  Asn  Ile  Asn  Leu  Phe  Asp  Tyr
               420                      425                      430

Thr  Asp  Thr  Leu  Val  Ser  Gly  Lys  Met  Ala  Leu  Asn  Leu  Trp  Pro  Val
               435                      440                      445

Pro  His  Gly  Leu  Glu  Asp  Leu  Leu  Asn  Pro  Ile  Gly  Val  Thr  Gly  Ser
     450                      455                      460

Asn  Pro  Asn  Lys  Glu  Thr  Pro  Cys  Leu  Glu  Leu  Glu  Phe  Asp  Trp  Phe
465                      470                      475                      480

Ser  Ser  Val  Val  Lys  Phe  Pro  Asp  Met  Ser  Val  Ile  Glu  Glu  His  Ala
                    485                      490                      495

Asn  Trp  Ser  Val  Ser  Arg  Glu  Ala  Gly  Phe  Ser  Tyr  Ser  His  Ala  Gly
               500                      505                      510

Leu  Ser  Asn  Arg  Leu  Ala  Arg  Asp  Asn  Glu  Leu  Arg  Glu  Asn  Asp  Lys
               515                      520                      525

Glu  Gln  Leu  Lys  Ala  Ile  Ser  Thr  Arg  Asp  Pro  Leu  Ser  Glu  Ile  Thr
     530                      535                      540

Glu  Gln  Glu  Lys  Asp  Phe  Leu  Trp  Ser  His  Arg  His  Tyr  Cys  Val  Thr
545                      550                      555                      560

Ile  Pro  Glu  Ile  Leu  Pro  Lys  Leu  Leu  Leu  Ser  Val  Lys  Trp  Asn  Ser
                    565                      570                      575

Arg  Asp  Glu  Val  Ala  Gln  Met  Tyr  Cys  Leu  Val  Lys  Asp  Trp  Pro  Pro
               580                      585                      590

Ile  Lys  Pro  Glu  Gln  Ala  Met  Glu  Leu  Leu  Asp  Cys  Asn  Tyr  Pro  Asp
          595                      600                      605

Pro  Met  Val  Arg  Gly  Phe  Ala  Val  Arg  Cys  Leu  Glu  Lys  Tyr  Leu  Thr
     610                      615                      620

Asp  Asp  Lys  Leu  Ser  Gln  Tyr  Leu  Ile  Gln  Leu  Val  Gln  Val  Leu  Lys
625                      630                      635                      640

Tyr  Glu  Gln  Tyr  Leu  Asp  Asn  Leu  Leu  Val  Arg  Phe  Leu  Leu  Lys  Lys
                    645                      650                      655

Ala  Leu  Thr  Asn  Gln  Arg  Ile  Gly  His  Phe  Phe  Phe  Trp  His  Leu  Lys
               660                      665                      670

Ser  Glu  Met  His  Asn  Lys  Thr  Val  Ser  Gln  Arg  Phe  Gly  Leu  Leu  Leu
          675                      680                      685

Glu  Ser  Tyr  Cys  Arg  Ala  Cys  Gly  Met  Tyr  Leu  Lys  His  Leu  Asn  Arg
     690                      695                      700

Gln  Val  Glu  Ala  Met  Glu  Lys  Leu  Ile  Asn  Leu  Thr  Asp  Ile  Leu  Lys
705                      710                      715                      720

Gln  Glu  Arg  Lys  Asp  Glu  Thr  Gln  Lys  Val  Gln  Met  Lys  Phe  Leu  Val
                    725                      730                      735

Glu  Gln  Met  Arg  Arg  Pro  Asp  Phe  Met  Asp  Ala  Leu  Gln  Gly  Leu  Leu
               740                      745                      750

Ser  Pro  Leu  Asn  Pro  Ala  His  Gln  Leu  Gly  Asn  Leu  Arg  Leu  Lys  Glu
          755                      760                      765

Cys  Arg  Ile  Met  Ser  Ser  Ala  Lys  Arg  Pro  Leu  Trp  Leu  Asn  Trp  Glu
     770                      775                      780

Asn  Pro  Asp  Ile  Met  Ser  Glu  Leu  Leu  Phe  Gln  Asn  Asn  Glu  Ile  Ile
```

|     |     |     |     |     |     |     |     |     |     |     |     |     |     |     |     |
| --- | --- | --- | --- | --- | --- | --- | --- | --- | --- | --- | --- | --- | --- | --- | --- |
| 785 |     |     |     |     | 790 |     |     |     |     | 795 |     |     |     |     | 800 |
| Phe | Lys | Asn | Gly | Asp | Asp | Leu | Arg | Gln | Asp | Met | Leu | Thr | Leu | Gln | Ile |
|     |     |     |     | 805 |     |     |     |     | 810 |     |     |     |     | 815 |     |
| Ile | Arg | Ile | Met | Glu | Asn | Ile | Trp | Gln | Asn | Gly | Leu | Asp | Leu | Arg |     |
|     |     |     | 820 |     |     |     |     | 825 |     |     |     |     | 830 |     |     |
| Met | Leu | Pro | Tyr | Gly | Cys | Leu | Ser | Ile | Gly | Asp | Cys | Val | Gly | Leu | Ile |
|     |     |     | 835 |     |     |     | 840 |     |     |     |     | 845 |     |     |     |
| Glu | Val | Val | Arg | Asn | Ser | His | Thr | Ile | Met | Gln | Ile | Gln | Cys | Lys | Gly |
|     | 850 |     |     |     |     | 855 |     |     |     |     | 860 |     |     |     |     |
| Gly | Leu | Lys | Gly | Ala | Leu | Gln | Phe | Asn | Ser | His | Thr | Leu | His | Gln | Trp |
| 865 |     |     |     |     | 870 |     |     |     |     | 875 |     |     |     |     | 880 |
| Leu | Lys | Asp | Lys | Asn | Lys | Gly | Glu | Ile | Tyr | Asp | Ala | Ala | Ile | Asp | Leu |
|     |     |     |     | 885 |     |     |     |     | 890 |     |     |     |     | 895 |     |
| Phe | Thr | Arg | Ser | Cys | Ala | Gly | Tyr | Cys | Val | Ala | Thr | Phe | Ile | Leu | Gly |
|     |     |     | 900 |     |     |     |     | 905 |     |     |     |     | 910 |     |     |
| Ile | Gly | Asp | Arg | His | Asn | Ser | Asn | Ile | Met | Val | Lys | Asp | Asp | Gly | Gln |
|     |     |     | 915 |     |     |     |     | 920 |     |     |     |     | 925 |     |     |
| Leu | Phe | His | Ile | Asp | Phe | Gly | His | Phe | Leu | Asp | His | Lys | Lys | Lys | Lys |
|     | 930 |     |     |     |     | 935 |     |     |     |     | 940 |     |     |     |     |
| Phe | Gly | Tyr | Lys | Arg | Glu | Arg | Val | Pro | Phe | Val | Leu | Thr | Gln | Asp | Phe |
| 945 |     |     |     |     | 950 |     |     |     |     | 955 |     |     |     |     | 960 |
| Leu | Ile | Val | Ile | Ser | Lys | Gly | Ala | Gln | Glu | Cys | Thr | Lys | Thr | Arg | Glu |
|     |     |     |     | 965 |     |     |     |     | 970 |     |     |     |     | 975 |     |
| Phe | Glu | Arg | Phe | Gln | Glu | Met | Cys | Tyr | Lys | Ala | Tyr | Leu | Ala | Ile | Arg |
|     |     |     | 980 |     |     |     |     | 985 |     |     |     |     | 990 |     |     |
| Gln | His | Ala | Asn | Leu | Phe | Ile | Asn | Leu | Phe | Ser | Met | Met | Leu | Gly | Ser |
|     |     | 995 |     |     |     |     | 1000|     |     |     |     | 1005|     |     |     |
| Gly | Met | Pro | Glu | Leu | Gln | Ser | Phe | Asp | Asp | Ile | Ala | Tyr | Ile | Arg | Lys |
|     |     | 1010|     |     |     |     | 1015|     |     |     |     | 1020|     |     |     |
| Thr | Leu | Ala | Leu | Asp | Lys | Thr | Glu | Gln | Glu | Ala | Leu | Glu | Tyr | Phe | Met |
| 1025|     |     |     |     | 1030|     |     |     |     | 1035|     |     |     |     | 1040|
| Lys | Gln | Met | Asn | Asp | Ala | His | His | Gly | Gly | Trp | Thr | Thr | Lys | Met | Asp |
|     |     |     |     | 1045|     |     |     |     | 1050|     |     |     |     | 1055|     |
| Trp | Ile | Phe | His | Thr | Ile | Lys | Gln | His | Ala | Leu | Asn | Xaa | Lys | Ile | Thr |
|     |     |     | 1060|     |     |     |     | 1065|     |     |     |     | 1070|     |     |
| Glu | Lys | Met | Lys | Ala | His | Ser | Gly |     |     |     |     |     |     |     |     |
|     |     |     | 1075|     |     |     |     | 1080|     |     |     |     |     |     |     |

(2) INFORMATION FOR SEQ ID NO: 37:

(i) SEQUENCE CHARACTERISTICS:
        (A) LENGTH: 1069 amino acids
        (B) TYPE: amino acid
        (C) STRANDEDNESS: single
        (D) TOPOLOGY: linear (xi) SEQUENCE DESCRIPTION: SEQ ID NO: 37:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Pro | Pro | Arg | Pro | Ser | Ser | Gly | Glu | Leu | Trp | Gly | Ile | His | Leu | Met |
| 1   |     |     |     | 5   |     |     |     |     | 10  |     |     |     |     | 15  |     |
| Pro | Pro | Arg | Ile | Leu | Val | Glu | Cys | Leu | Leu | Pro | Asn | Gly | Met | Ile | Val |
|     |     |     | 20  |     |     |     |     | 25  |     |     |     |     | 30  |     |     |
| Thr | Leu | Glu | Cys | Leu | Arg | Glu | Ala | Thr | Leu | Ile | Thr | Ile | Lys | His | Glu |
|     |     | 35  |     |     |     |     | 40  |     |     |     |     | 45  |     |     |     |
| Leu | Phe | Lys | Glu | Ala | Arg | Lys | Tyr | Pro | Leu | His | Gln | Leu | Leu | Gln | Asp |
|     | 50  |     |     |     |     | 55  |     |     |     |     | 60  |     |     |     |     |
| Glu | Ser | Ser | Tyr | Ile | Phe | Val | Ser | Val | Thr | Gln | Glu | Ala | Glu | Arg | Glu |

|   |   |   |   |   |   |   |   |   |   |   |   |   |   |   |   |
|---|---|---|---|---|---|---|---|---|---|---|---|---|---|---|---|
| 65 |   |   |   |   | 70 |   |   |   |   | 75 |   |   |   |   | 80 |
| Glu | Phe | Phe | Asp | Glu 85 | Thr | Arg | Arg | Leu | Cys 90 | Asp | Leu | Arg | Leu | Phe 95 | Gln |
| Pro | Phe | Leu | Lys 100 | Val | Ile | Glu | Pro | Val 105 | Gly | Asn | Arg | Glu | Glu 110 | Lys | Ile |
| Leu | Asn | Arg 115 | Glu | Ile | Gly | Phe | Ala 120 | Ile | Gly | Met | Pro | Val 125 | Cys | Glu | Phe |
| Asp | Met 130 | Val | Lys | Asp | Pro | Glu 135 | Val | Gln | Asp | Phe | Arg 140 | Arg | Asn | Ile | Leu |
| Asn 145 | Val | Cys | Lys | Glu | Ala 150 | Val | Asp | Leu | Arg | Asp 155 | Leu | Asn | Ser | Pro | His 160 |
| Ser | Arg | Ala | Met | Tyr 165 | Val | Tyr | Pro | Asn | Val 170 | Glu | Ser | Ser | Pro | Glu 175 |   |
| Leu | Pro | Lys | His 180 | Ile | Tyr | Asn | Lys | Leu 185 | Asp | Lys | Gly | Gln | Ile 190 | Ile | Val |
| Val | Ile | Trp 195 | Val | Ile | Val | Ser | Pro 200 | Asn | Asn | Asp | Lys | Gln 205 | Lys | Tyr | Thr |
| Leu | Lys 210 | Ile | Asn | His | Asp | Cys 215 | Val | Pro | Glu | Gln | Val 220 | Ile | Ala | Glu | Ala |
| Ile 225 | Arg | Lys | Lys | Thr | Arg 230 | Ser | Met | Leu | Leu | Ser 235 | Ser | Glu | Gln | Leu | Lys 240 |
| Leu | Cys | Val | Leu | Glu 245 | Tyr | Gln | Gly | Lys | Tyr 250 | Ile | Leu | Lys | Val | Cys 255 | Gly |
| Cys | Asp | Glu | Tyr 260 | Phe | Leu | Glu | Lys | Tyr 265 | Pro | Leu | Ser | Gln | Tyr 270 | Lys | Tyr |
| Ile | Arg | Ser 275 | Cys | Ile | Met | Leu | Gly 280 | Arg | Met | Pro | Asn | Leu 285 | Met | Leu | Met |
| Ala | Lys 290 | Glu | Ser | Leu | Tyr | Ser 295 | Gln | Leu | Pro | Met | Asp 300 | Cys | Phe | Thr | Met |
| Pro 305 | Ser | Tyr | Ser | Arg | Arg 310 | Ile | Ser | Thr | Ala | Thr 315 | Pro | Tyr | Met | Asn | Gly 320 |
| Glu | Thr | Ser | Thr | Lys 325 | Ser | Leu | Trp | Val | Ile 330 | Asn | Ser | Ala | Leu | Arg 335 | Ile |
| Lys | Ile | Leu | Cys 340 | Ala | Thr | Tyr | Val | Asn 345 | Val | Asn | Ile | Arg | Asp 350 | Ile | Asp |
| Lys | Ile | Tyr 355 | Val | Arg | Thr | Gly | Ile 360 | Tyr | His | Gly | Gly | Glu 365 | Pro | Leu | Cys |
| Asp | Asn 370 | Val | Asn | Thr | Gln | Arg 375 | Val | Pro | Cys | Ser | Asn 380 | Pro | Arg | Trp | Asn |
| Glu 385 | Trp | Leu | Asn | Tyr | Asp 390 | Ile | Tyr | Ile | Pro | Asp 395 | Leu | Pro | Arg | Ala | Ala 400 |
| Arg | Leu | Cys | Leu | Ser 405 | Ile | Cys | Ser | Val | Lys 410 | Gly | Arg | Lys | Gly | Ala 415 | Lys |
| Glu | Glu | His | Cys 420 | Pro | Leu | Ala | Trp | Gly 425 | Asn | Ile | Asn | Leu | Phe 430 | Asp | Tyr |
| Thr | Asp | Thr 435 | Leu | Val | Ser | Gly | Lys 440 | Met | Ala | Leu | Asn | Leu 445 | Trp | Pro | Val |
| Pro | His 450 | Gly | Leu | Glu | Asp | Leu 455 | Leu | Asn | Pro | Ile | Gly 460 | Val | Thr | Gly | Ser |
| Asn 465 | Pro | Asn | Lys | Glu | Thr 470 | Pro | Cys | Leu | Glu | Leu 475 | Glu | Phe | Asp | Trp | Phe 480 |
| Ser | Ser | Val | Val | Lys 485 | Phe | Pro | Asp | Met | Ser 490 | Val | Ile | Glu | Glu | His 495 | Ala |

```
Asn  Trp  Ser  Val  Ser  Arg  Glu  Ala  Gly  Phe  Ser  Tyr  Ser  His  Ala  Gly
               500                 505                      510

Leu  Ser  Asn  Arg  Leu  Ala  Arg  Asp  Asn  Glu  Leu  Arg  Glu  Asn  Asp  Lys
               515                 520                      525

Glu  Gln  Leu  Arg  Ala  Ile  Cys  Thr  Arg  Asp  Pro  Leu  Ser  Glu  Ile  Thr
     530                      535                      540

Glu  Gln  Glu  Lys  Asp  Phe  Leu  Trp  Ser  His  Arg  His  Tyr  Cys  Val  Thr
545                      550                      555                      560

Ile  Pro  Glu  Ile  Leu  Pro  Lys  Leu  Leu  Ser  Val  Lys  Trp  Asn  Ser
               565                 570                      575

Arg  Asp  Glu  Val  Ala  Gln  Met  Tyr  Cys  Leu  Val  Lys  Asp  Trp  Pro  Pro
               580                 585                      590

Ile  Lys  Pro  Glu  Gln  Ala  Met  Glu  Leu  Leu  Asp  Cys  Asn  Tyr  Pro  Asp
          595                 600                           605

Pro  Met  Val  Arg  Gly  Phe  Ala  Val  Arg  Cys  Leu  Glu  Lys  Tyr  Leu  Thr
     610                      615                      620

Asp  Asp  Lys  Leu  Ser  Gln  Tyr  Leu  Ile  Gln  Leu  Val  Gln  Val  Leu  Lys
625                      630                      635                      640

Tyr  Glu  Gln  Tyr  Leu  Asp  Asn  Leu  Leu  Val  Arg  Phe  Leu  Leu  Lys  Lys
                    645                 650                           655

Ala  Leu  Thr  Asn  Gln  Arg  Ile  Gly  His  Phe  Phe  Phe  Trp  His  Leu  Lys
               660                      665                      670

Ser  Glu  Met  His  Asn  Lys  Thr  Val  Ser  Gln  Arg  Phe  Gly  Leu  Leu  Leu
          675                      680                      685

Glu  Ser  Tyr  Cys  Arg  Ala  Cys  Gly  Met  Tyr  Leu  Lys  His  Leu  Asn  Arg
     690                      695                      700

Gln  Val  Glu  Ala  Met  Glu  Lys  Leu  Ile  Asn  Leu  Thr  Asp  Ile  Leu  Lys
705                      710                      715                      720

Gln  Glu  Lys  Lys  Asp  Glu  Thr  Gln  Lys  Val  Gln  Met  Lys  Phe  Leu  Val
               725                      730                      735

Glu  Gln  Met  Arg  Arg  Pro  Asp  Phe  Met  Asp  Ala  Leu  Gln  Gly  Phe  Leu
          740                      745                      750

Ser  Pro  Leu  Asn  Pro  Ala  His  Gln  Leu  Gly  Asn  Leu  Arg  Leu  Glu  Glu
          755                      760                      765

Cys  Arg  Ile  Met  Ser  Ser  Ala  Lys  Arg  Pro  Leu  Trp  Leu  Asn  Trp  Glu
     770                      775                      780

Asn  Pro  Asp  Ile  Met  Ser  Glu  Leu  Leu  Phe  Gln  Asn  Asn  Glu  Ile  Ile
785                      790                      795                      800

Phe  Lys  Asn  Gly  Asp  Asp  Leu  Arg  Gln  Asp  Met  Leu  Thr  Leu  Gln  Ile
               805                      810                      815

Ile  Arg  Ile  Met  Glu  Asn  Ile  Trp  Gln  Asn  Gln  Gly  Leu  Asp  Leu  Arg
               820                      825                      830

Met  Leu  Pro  Tyr  Gly  Cys  Leu  Ser  Ile  Gly  Asp  Cys  Val  Gly  Leu  Ile
          835                      840                      845

Glu  Val  Val  Arg  Asn  Ser  His  Thr  Ile  Met  Gln  Ile  Gln  Cys  Lys  Gly
     850                      855                      860

Gly  Leu  Lys  Gly  Ala  Leu  Gln  Phe  Asn  Ser  His  Thr  Leu  His  Gln  Trp
865                      870                      875                      880

Leu  Lys  Asp  Lys  Asn  Lys  Gly  Glu  Ile  Tyr  Asp  Ala  Ala  Ile  Asp  Leu
                    885                      890                      895

Phe  Thr  Arg  Ser  Cys  Ala  Gly  Tyr  Cys  Val  Ala  Thr  Phe  Ile  Leu  Gly
               900                      905                      910

Ile  Gly  Asp  Arg  His  Asn  Ser  Asn  Ile  Met  Val  Lys  Asp  Gly  Gln
               915                      920                      925
```

```
Leu  Phe  His  Ile  Asp  Phe  Gly  His  Phe  Leu  Asp  His  Lys  Lys  Lys  Lys
     930                      935                 940

Phe  Gly  Tyr  Lys  Arg  Glu  Arg  Val  Pro  Phe  Val  Leu  Thr  Gln  Asp  Phe
945                      950                 955                           960

Leu  Ile  Val  Ile  Ser  Lys  Gly  Ala  Gln  Glu  Cys  Thr  Lys  Thr  Arg  Glu
               965                      970                      975

Phe  Glu  Arg  Phe  Gln  Glu  Met  Cys  Tyr  Lys  Ala  Tyr  Leu  Ala  Ile  Arg
               980                 985                           990

Gln  His  Ala  Asn  Leu  Phe  Ile  Asn  Leu  Phe  Ser  Met  Met  Leu  Gly  Ser
          995                      1000                 1005

Gly  Met  Pro  Glu  Leu  Gln  Ser  Phe  Asp  Asp  Ile  Ala  Tyr  Ile  Arg  Lys
          1010                1015                     1020

Thr  Leu  Ala  Leu  Asp  Lys  Thr  Glu  Gln  Glu  Ala  Leu  Glu  Tyr  Phe  Met
1025                1030                     1035                          1040

Lys  Gln  Met  Asn  Asp  Ala  His  His  Gly  Gly  Trp  Thr  Thr  Lys  Met  Asp
                    1045                     1050                1055

Trp  Ile  Phe  His  Thr  Ile  Lys  Gln  His  Ala  Leu  Asn  Xaa
               1060                1065
```

( 2 ) INFORMATION FOR SEQ ID NO: 38:

( i ) SEQUENCE CHARACTERISTICS:
        ( A ) LENGTH: 381 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..381

( x i ) SEQUENCE DESCRIPTION: SEQ ID NO: 38:

```
GGA  GAC  GAC  TTG  CGA  CAG  GAT  CAA  CTT  ATT  CTT  CAA  ATC  ATT  TCA  CTC       48
Gly  Asp  Asp  Leu  Arg  Gln  Asp  Gln  Leu  Ile  Leu  Gln  Ile  Ile  Ser  Leu
 1                       5                       10                      15

ATG  GAC  AAG  CTG  TTA  CGG  AAA  GAA  AAT  CTG  GAC  TTG  AAA  TTG  ACA  CCT       96
Met  Asp  Lys  Leu  Leu  Arg  Lys  Glu  Asn  Leu  Asp  Leu  Lys  Leu  Thr  Pro
                    20                      25                      30

TAT  AAG  GTG  TTA  GCC  ACC  AGT  ACA  AAA  CAT  GGC  TTC  ATG  CAG  TTT  ATC      144
Tyr  Lys  Val  Leu  Ala  Thr  Ser  Thr  Lys  His  Gly  Phe  Met  Gln  Phe  Ile
               35                      40                      45

CAG  TCA  GTT  CCT  GTG  GCT  GAA  GTT  CTT  GAT  ACA  GAG  GGA  AGC  ATT  CAG      192
Gln  Ser  Val  Pro  Val  Ala  Glu  Val  Leu  Asp  Thr  Glu  Gly  Ser  Ile  Gln
          50                      55                      60

AAC  TTT  TTT  AGA  AAA  TAT  GCA  CCA  AGT  GAG  AAT  GGG  CCA  AAT  GGG  ATT      240
Asn  Phe  Phe  Arg  Lys  Tyr  Ala  Pro  Ser  Glu  Asn  Gly  Pro  Asn  Gly  Ile
 65                      70                      75                      80

AGT  GCT  GAG  GTC  ATG  GAC  ACT  TAC  GTT  AAA  AGC  TGT  GCT  GGA  TAT  TGC      288
Ser  Ala  Glu  Val  Met  Asp  Thr  Tyr  Val  Lys  Ser  Cys  Ala  Gly  Tyr  Cys
                    85                      90                      95

GTG  ATC  ACC  TAT  ATA  CTT  GGA  GTT  GGA  GAC  AGG  CAC  CTG  GAT  AAC  CTT      336
Val  Ile  Thr  Tyr  Ile  Leu  Gly  Val  Gly  Asp  Arg  His  Leu  Asp  Asn  Leu
               100                     105                     110

TTG  CTA  ACC  AAA  ACA  GGC  AAA  CTC  TTC  CAC  ATC  GAT  TTC  GGC  CAC           381
Leu  Leu  Thr  Lys  Thr  Gly  Lys  Leu  Phe  His  Ile  Asp  Phe  Gly  His
          115                     120                     125
```

( 2 ) INFORMATION FOR SEQ ID NO: 39:

( i ) SEQUENCE CHARACTERISTICS:
        ( A ) LENGTH: 127 amino acids (B) TYPE: amino acid
(D) TOPOLOGY: linear (ii) MOLECULE TYPE: protein (xi) SEQUENCE DESCRIPTION: SEQ ID NO: 39:

| Gly | Asp | Asp | Leu | Arg | Gln | Asp | Gln | Leu | Ile | Leu | Gln | Ile | Ile | Ser | Leu |
|---|---|---|---|---|---|---|---|---|---|---|---|---|---|---|---|
| 1 | | | | 5 | | | | | 10 | | | | | 15 | |
| Met | Asp | Lys | Leu | Leu | Arg | Lys | Glu | Asn | Leu | Asp | Leu | Lys | Leu | Thr | Pro |
| | | | | 20 | | | | | 25 | | | | | 30 | |
| Tyr | Lys | Val | Leu | Ala | Thr | Ser | Thr | Lys | His | Gly | Phe | Met | Gln | Phe | Ile |
| | | | 35 | | | | | 40 | | | | | 45 | | |
| Gln | Ser | Val | Pro | Val | Ala | Glu | Val | Leu | Asp | Thr | Glu | Gly | Ser | Ile | Gln |
| | | 50 | | | | | 55 | | | | | 60 | | | |
| Asn | Phe | Phe | Arg | Lys | Tyr | Ala | Pro | Ser | Glu | Asn | Gly | Pro | Asn | Gly | Ile |
| 65 | | | | | 70 | | | | | 75 | | | | | 80 |
| Ser | Ala | Glu | Val | Met | Asp | Thr | Tyr | Val | Lys | Ser | Cys | Ala | Gly | Tyr | Cys |
| | | | | 85 | | | | | 90 | | | | | 95 | |
| Val | Ile | Thr | Tyr | Ile | Leu | Gly | Val | Gly | Asp | Arg | His | Leu | Asp | Asn | Leu |
| | | | | 100 | | | | | 105 | | | | | 110 | |
| Leu | Leu | Thr | Lys | Thr | Gly | Lys | Leu | Phe | His | Ile | Asp | Phe | Gly | His | |
| | | 115 | | | | | 120 | | | | | 125 | | | |

(2) INFORMATION FOR SEQ ID NO: 40:

(i) SEQUENCE CHARACTERISTICS:
(A) LENGTH: 393 base pairs
(B) TYPE: nucleic acid
(C) STRANDEDNESS: single
(D) TOPOLOGY: linear (ix) FEATURE:
(A) NAME/KEY: CDS
(B) LOCATION: 1..393

(xi) SEQUENCE DESCRIPTION: SEQ ID NO: 40:

| GGG | GAT | GAC | TTA | CGG | CAG | GAC | ATG | CTA | ACG | CTG | CAG | ATG | ATT | CGC | ATC | 48 |
|---|---|---|---|---|---|---|---|---|---|---|---|---|---|---|---|---|
| Gly | Asp | Asp | Leu | Arg | Gln | Asp | Met | Leu | Thr | Leu | Gln | Met | Ile | Arg | Ile | |
| 1 | | | | 5 | | | | | 10 | | | | | 15 | | |
| ATG | AGC | AAG | ATC | TGG | GTC | CAG | GAG | GGG | CTG | GAC | ATG | CGC | ATG | GTC | ATC | 96 |
| Met | Ser | Lys | Ile | Trp | Val | Gln | Glu | Gly | Leu | Asp | Met | Arg | Met | Val | Ile | |
| | | | 20 | | | | | 25 | | | | | 30 | | | |
| TTC | CGC | TGC | TTC | TCC | ACC | GGC | CGG | GGC | AGA | GGG | ATG | GTG | GAG | ATG | ATC | 144 |
| Phe | Arg | Cys | Phe | Ser | Thr | Gly | Arg | Gly | Arg | Gly | Met | Val | Glu | Met | Ile | |
| | | 35 | | | | | 40 | | | | | 45 | | | | |
| CCT | AAT | GCT | GAG | ACC | CTG | CGT | AAG | ATC | CAG | GTG | GAG | CAT | GGG | GTG | ACC | 192 |
| Pro | Asn | Ala | Glu | Thr | Leu | Arg | Lys | Ile | Gln | Val | Glu | His | Gly | Val | Thr | |
| | 50 | | | | | 55 | | | | | 60 | | | | | |
| GGC | TCG | TTC | AAG | GAC | CGG | CCC | CTG | GCA | GAC | CGG | CTG | CAG | AAA | CAC | AAC | 240 |
| Gly | Ser | Phe | Lys | Asp | Arg | Pro | Leu | Ala | Asp | Arg | Leu | Gln | Lys | His | Asn | |
| 65 | | | | | 70 | | | | | 75 | | | | | 80 | |
| CCT | GGG | GAG | GAC | GAG | TAT | GAG | AAG | GCT | GTG | GAG | AAC | TTT | ATC | TAC | TCC | 288 |
| Pro | Gly | Glu | Asp | Glu | Tyr | Glu | Lys | Ala | Val | Glu | Asn | Phe | Ile | Tyr | Ser | |
| | | | | 85 | | | | | 90 | | | | | 95 | | |
| TGC | GCT | GGC | TGC | TGC | GTG | GCC | ACG | TAC | GTC | TTG | GGC | ATC | TGT | GAC | CGA | 336 |
| Cys | Ala | Gly | Cys | Cys | Val | Ala | Thr | Tyr | Val | Leu | Gly | Ile | Cys | Asp | Arg | |
| | | | 100 | | | | | 105 | | | | | 110 | | | |
| CAT | AAT | GAC | AAC | ATC | ATG | CTG | AAG | ACC | ACT | GGT | CAC | ATG | TTC | CAC | ATC | 384 |
| His | Asn | Asp | Asn | Ile | Met | Leu | Lys | Thr | Thr | Gly | His | Met | Phe | His | Ile | |
| | | 115 | | | | | 120 | | | | | 125 | | | | |
| GAC | TTC | GGC | | | | | | | | | | | | | | 393 |
| Asp | Phe | Gly | | | | | | | | | | | | | | |

130

( 2 ) INFORMATION FOR SEQ ID NO: 41:

( i ) SEQUENCE CHARACTERISTICS:
        ( A ) LENGTH: 131 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 41:

```
Gly Asp Asp Leu Arg Gln Asp Met Leu Thr Leu Gln Met Ile Arg Ile
 1               5                  10                  15

Met Ser Lys Ile Trp Val Gln Glu Gly Leu Asp Met Arg Met Val Ile
             20                  25                  30

Phe Arg Cys Phe Ser Thr Gly Arg Gly Arg Gly Met Val Glu Met Ile
         35                  40                  45

Pro Asn Ala Glu Thr Leu Arg Lys Ile Gln Val Glu His Gly Val Thr
     50                  55                  60

Gly Ser Phe Lys Asp Arg Pro Leu Ala Asp Arg Leu Gln Lys His Asn
65                  70                  75                  80

Pro Gly Glu Asp Glu Tyr Glu Lys Ala Val Glu Asn Phe Ile Tyr Ser
                 85                  90                  95

Cys Ala Gly Cys Cys Val Ala Thr Tyr Val Leu Gly Ile Cys Asp Arg
                100                 105                 110

His Asn Asp Asn Ile Met Leu Lys Thr Thr Gly His Met Phe His Ile
            115                 120                 125

Asp Phe Gly
        130
```

( 2 ) INFORMATION FOR SEQ ID NO: 42:

( i ) SEQUENCE CHARACTERISTICS:
        ( A ) LENGTH: 66 amino acids
        ( B ) TYPE: amino acid
        ( C ) STRANDEDNESS: single
        ( D ) TOPOLOGY: linear ( x i ) SEQUENCE DESCRIPTION: SEQ ID NO: 42:

```
Gly Asp Asp Leu Arg Gln Asp Gln Leu Val Val Gln Ile Ile Ser Leu
 1               5                  10                  15

Met Asn Glu Leu Leu Lys Asn Glu Asn Val Asp Leu Lys Leu Thr Pro
             20                  25                  30

Tyr Lys Ile Leu Ala Thr Gly Pro Gln Glu Gly Ala Ile Glu Phe Ile
         35                  40                  45

Pro Asn Asp Thr Leu Ala Ser Ile Leu Ser Lys Tyr His Gly Ile Leu
     50                  55                  60

Gly Tyr
65
```

( 2 ) INFORMATION FOR SEQ ID NO: 43:

( i ) SEQUENCE CHARACTERISTICS:
        ( A ) LENGTH: 60 amino acids
        ( B ) TYPE: amino acid
        ( C ) STRANDEDNESS: single
        ( D ) TOPOLOGY: linear ( x i ) SEQUENCE DESCRIPTION: SEQ ID NO: 43:

```
Leu Lys Leu His Tyr Pro Asp Glu Asn Ala Thr Leu Gly Val Gln Gly
 1               5                  10                  15
```

```
              Trp  Val  Leu  Asp  Asn  Phe  Val  Lys  Ser  Cys  Ala  Gly  Tyr  Cys  Val  Ile
                             20                       25                       30

Thr  Tyr  Ile  Leu  Gly  Val  Gly  Asp  Arg  His  Leu  Asp  Asn  Leu  Leu  Val
                        35                       40                       45

Thr  Pro  Asp  Gly  His  Phe  Phe  His  Ala  Asp  Phe  Gly
                   50                       55                       60
```

( 2 ) INFORMATION FOR SEQ ID NO: 44:

( i ) SEQUENCE CHARACTERISTICS:
    ( A ) LENGTH: 66 amino acids
    ( B ) TYPE: amino acid
    ( C ) STRANDEDNESS: single
    ( D ) TOPOLOGY: linear ( x i ) SEQUENCE DESCRIPTION: SEQ ID NO: 44:

```
              Gly  Asp  Asp  Leu  Arg  Gln  Asp  Gln  Leu  Ile  Leu  Gln  Ile  Ile  Ser  Leu
              1                   5                       10                      15

Met  Asp  Lys  Leu  Leu  Arg  Lys  Glu  Asn  Leu  Asp  Leu  Lys  Leu  Thr  Pro
                             20                       25                       30

Tyr  Lys  Val  Leu  Ala  Thr  Ser  Thr  Lys  His  Gly  Phe  Met  Gln  Phe  Ile
                        35                       40                       45

Gln  Ser  Val  Pro  Val  Ala  Glu  Val  Leu  Asp  Thr  Glu  Gly  Ser  Ile  Gln
                   50                       55                       60

Asn  Phe
              65
```

( 2 ) INFORMATION FOR SEQ ID NO: 45:

( i ) SEQUENCE CHARACTERISTICS:
    ( A ) LENGTH: 60 amino acids
    ( B ) TYPE: amino acid
    ( C ) STRANDEDNESS: single
    ( D ) TOPOLOGY: linear ( x i ) SEQUENCE DESCRIPTION: SEQ ID NO: 45:

```
              Phe  Arg  Lys  Tyr  Ala  Pro  Ser  Glu  Asn  Gly  Pro  Asn  Gly  Ile  Ser  Ala
              1                   5                       10                      15

Glu  Val  Met  Asp  Thr  Tyr  Val  Lys  Ser  Cys  Ala  Gly  Tyr  Cys  Val  Ile
                             20                       25                       30

Thr  Tyr  Ile  Leu  Gly  Val  Gly  Asp  Arg  His  Leu  Asp  Asn  Leu  Leu  Leu
                        35                       40                       45

Thr  Lys  Thr  Gly  Lys  Leu  Phe  His  Ile  Asp  Phe  Gly
                   50                       55                       60
```

( 2 ) INFORMATION FOR SEQ ID NO: 46:

( i ) SEQUENCE CHARACTERISTICS:
    ( A ) LENGTH: 85 amino acids
    ( B ) TYPE: amino acid
    ( C ) STRANDEDNESS: single
    ( D ) TOPOLOGY: linear ( x i ) SEQUENCE DESCRIPTION: SEQ ID NO: 46:

```
              Gly  Asp  Asp  Leu  Arg  Gln  Asp  Met  Leu  Thr  Leu  Gln  Ile  Ile  Arg  Ile
              1                   5                       10                      15

Met  Glu  Asn  Ile  Trp  Gln  Asn  Gln  Gly  Leu  Asp  Leu  Arg  Met  Leu  Pro
                             20                       25                       30

Tyr  Gly  Cys  Leu  Ser  Ile  Gly  Asp  Cys  Val  Gly  Leu  Ile  Glu  Val  Val
                        35                       40                       45

Arg  Asn  Ser  His  Thr  Ile  Met  Gln  Ile  Gln  Cys  Lys  Gly  Gly  Leu  Lys
```

Gly Ala Leu Gln Phe Asn Ser His Thr Leu His Gln Trp Leu Lys Asp
65                  70                  75                  80

Lys Asn Lys Gly Glu
                85

( 2 ) INFORMATION FOR SEQ ID NO: 47:

( i ) SEQUENCE CHARACTERISTICS:
       ( A ) LENGTH: 47 amino acids
       ( B ) TYPE: amino acid
       ( C ) STRANDEDNESS: single
       ( D ) TOPOLOGY: linear ( x i ) SEQUENCE DESCRIPTION: SEQ ID NO: 47:

Ile Tyr Asp Ala Ala Ile Asp Leu Phe Thr Arg Ser Cys Ala Gly Tyr
1                5                   10                  15

Cys Val Ala Thr Phe Ile Leu Gly Ile Gly Asp Arg His Asn Ser Asn
                20                  25                  30

Ile Met Val Lys Asp Asp Gly Gln Leu Phe His Ile Asp Phe Gly
35                  40                  45

( 2 ) INFORMATION FOR SEQ ID NO: 48:

( i ) SEQUENCE CHARACTERISTICS:
       ( A ) LENGTH: 66 amino acids
       ( B ) TYPE: amino acid
       ( C ) STRANDEDNESS: single
       ( D ) TOPOLOGY: linear ( x i ) SEQUENCE DESCRIPTION: SEQ ID NO: 48:

Gly Asp Asp Leu Arg Gln Asp Met Leu Thr Leu Gln Met Ile Arg Ile
1                5                   10                  15

Met Ser Lys Ile Trp Val Gln Glu Gly Leu Asp Met Arg Met Val Ile
                20                  25                  30

Phe Arg Cys Phe Ser Thr Gly Arg Gly Arg Gly Met Val Glu Met Ile
                35                  40                  45

Pro Asn Ala Glu Thr Leu Arg Lys Ile Gln Val Glu His Gly Val Thr
50                  55                  60

Gly Ser
65

( 2 ) INFORMATION FOR SEQ ID NO: 49:

( i ) SEQUENCE CHARACTERISTICS:
       ( A ) LENGTH: 65 amino acids
       ( B ) TYPE: amino acid
       ( C ) STRANDEDNESS: single
       ( D ) TOPOLOGY: linear ( x i ) SEQUENCE DESCRIPTION: SEQ ID NO: 49:

Phe Lys Asp Arg Pro Leu Ala Asp Arg Leu Gln Lys His Asn Pro Gly
1                5                   10                  15

Glu Asp Glu Tyr Glu Lys Ala Val Glu Asn Phe Ile Tyr Ser Cys Ala
                20                  25                  30

Gly Cys Cys Val Ala Thr Tyr Val Leu Gly Ile Cys Asp Arg His Asn
                35                  40                  45

Asp Asn Ile Met Leu Lys Thr Thr Gly His Met Phe His Ile Asp Phe
50                  55                  60

Gly
65

( 2 ) INFORMATION FOR SEQ ID NO: 50:

( i ) SEQUENCE CHARACTERISTICS:
      ( A ) LENGTH: 62 amino acids
      ( B ) TYPE: amino acid
      ( C ) STRANDEDNESS: single
      ( D ) TOPOLOGY: linear ( x i ) SEQUENCE DESCRIPTION: SEQ ID NO: 50:

```
Gly Asp Asp Leu Arg Gln Asp Leu Leu Gln Ile Ile Met Glu Leu Asp
1               5                   10                  15

Leu Pro Tyr Leu Thr Gly Gly Ile Glu Ile Asn Gly Ile Gly Leu Asn
            20                  25                  30

Ile Asp Phe Val Ser Cys Ala Gly Tyr Cys Val Thr Tyr Ile Leu Gly
        35                  40                  45

Gly Asp Arg His Asp Asn Gly Leu Phe His Ile Asp Phe Gly
    50                  55                  60
```